US008143006B2

(12) United States Patent
Kutyavin

(10) Patent No.: US 8,143,006 B2
(45) Date of Patent: Mar. 27, 2012

(54) ACCELERATED CASCADE AMPLIFICATION (ACA) OF NUCLEIC ACIDS COMPRISING STRAND AND SEQUENCE SPECIFIC DNA NICKING

(76) Inventor: Igor Kutyavin, Woodinville, WA (US)

( * ) Notice: Subject to any disclaimer, the term of this patent is extended or adjusted under 35 U.S.C. 154(b) by 317 days.

(21) Appl. No.: 12/185,699

(22) Filed: Aug. 4, 2008

(65) Prior Publication Data

US 2009/0047678 A1 Feb. 19, 2009

Related U.S. Application Data

(60) Provisional application No. 60/953,931, filed on Aug. 3, 2007.

(51) Int. Cl.
C12Q 1/68 (2006.01)
C12P 19/34 (2006.01)

(52) U.S. Cl. ..................................... 435/6.12; 435/91.2

(58) Field of Classification Search ............. 435/6, 91.2, 435/6.12
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,835,263 A | 5/1989 | Nguyen et al. | |
| 5,270,184 A | 12/1993 | Walker et al. | |
| 5,648,211 A | 7/1997 | Fraiser et al. | |
| 5,659,022 A | 8/1997 | Kutyavin et al. | |
| 5,712,124 A | 1/1998 | Walker | |
| 5,801,155 A | 9/1998 | Kutyavin et al. | |
| 5,824,517 A | 10/1998 | Cleuziat et al. | |
| 5,854,033 A | 12/1998 | Lizardi | |
| 6,063,603 A | 5/2000 | Davey et al. | |
| 6,124,120 A | 9/2000 | Lizardi | |
| 6,143,495 A | 11/2000 | Lizardi et al. | |
| 6,210,884 B1 | 4/2001 | Lizardi | |
| 6,251,639 B1 | 6/2001 | Kurn | |
| 6,287,824 B1 | 9/2001 | Lizardi | |
| 6,410,278 B1 | 6/2002 | Notomi et al. | |
| 6,692,918 B2 | 2/2004 | Kurn | |
| 6,858,413 B2 | 2/2005 | Kurn | |
| 6,864,071 B2 * | 3/2005 | Carrino et al. ............... | 435/91.2 |
| 7,056,671 B2 | 6/2006 | Enoki | |
| 7,198,894 B2 | 4/2007 | Barany et al. | |
| 2003/0073081 A1 | 4/2003 | Mukai et al. | |
| 2003/0138800 A1 | 7/2003 | Van Ness et al. | |
| 2004/0101893 A1 | 5/2004 | Kutyavin et al. | |
| 2005/0064463 A1 | 3/2005 | Hedgpeth | |
| 2005/0118578 A1 | 6/2005 | Mineno | |
| 2005/0136417 A1 | 6/2005 | Cole et al. | |
| 2007/0099216 A1 * | 5/2007 | Nakashima et al. ............... | 435/6 |

FOREIGN PATENT DOCUMENTS

| | | |
|---|---|---|
| EP | 1312682 | 5/2003 |
| EP | 1167524 | 5/2007 |
| WO | WO 99/09211 | 2/1999 |
| WO | WO 99/49081 | 9/1999 |
| WO | 03/008623 | 1/2003 |
| WO | 2005/056790 | 6/2005 |
| WO | WO 2006/125267 | 11/2006 |
| WO | WO 2007/043751 | 4/2007 |
| WO | WO 2007/127992 | 11/2007 |
| WO | WO 2007/127999 | 11/2007 |
| WO | WO 2008/086381 | 7/2008 |

OTHER PUBLICATIONS

Lowe et al. Nucleic acid reserach, 1990,vol. 18(7), p. 1757-1761.*
Bustin, "Absolute quantification of mRNA using real-time reverse transcription polymerase chain reaction assays," Journal of Molecular Endocrinology, 2000, pp. 169-193, vol. 25.
Huang et al., "Mutational Analysis of Endonuclease V from Thermotoga maritima," Biochemistry, 2002, pp. 8342-8350, vol. 41.
Nadeau et al., "Real-Time, Sequence-Specific Detection of Nucleic Acids during Strand Displacement Amplification," Analytical Biochemistry, 1999, pp. 177-187, vol. 276.
Walker, "Empirical aspects of strand displacement amplification," Genome Research, 1993, pp. 1-6, vol. 3.
Walker et al., "Isothermal in vitro amplification of DNA by a restriction enzyme/DNA polymerase system," The Proceedings of the National Academy of Sciences, 1992, pp. 392-396, vol. 89.
Walker et al., "Multiplex strand displacement amplification (SDA) and detection of DNA sequences from Mycobacterium tuberculosis and other mycobacteria," Nucleic Acids Research, 1994, pp. 2670-2677, vol. 22.
Westin et al., "Anchored multiplex amplification on a microelectronic chip array," Nature Biotechnology, 2000, pp. 199-204, vol. 18.
Afonina et al., "Efficient priming of PCR with short oligonucleotides conjugated to a minor groove binder," Nucleic Acids Research, 1997, pp. 2657-2660, vol. 25.

(Continued)

Primary Examiner — Kenneth R. Horlick
Assistant Examiner — Joyce Tung
(74) Attorney, Agent, or Firm — Barry L. Davison; Davis Wright Tremaine LLP

(57) ABSTRACT

Particular aspects provide nucleic acid amplification and detection methods comprising: providing a reaction mixture containing a target nucleic acid with an amplifiable target sequence, forward and reverse external nick-directing primers (ND-primers), at least one internal ND-primer, a strand-displacing DNA polymerase, a nick-directing endonuclease for strand-specific cleavage of ND-primer-extension products, and deoxynucleoside 5'-triphosphates; and incubating the reaction mixture with reagents, and under conditions suitable to provide for amplification of the amplifiable target sequence, wherein the amplification comprises primer extension, by least one internal ND-primer, of an external ND-primer extension product comprising the amplifiable target sequence or a portion thereof but lacking the respective external ND-primer sequence or a portion thereof. Preferably, amplification comprises using a plurality of internal ND-primers, extension of one internal ND-primer extension product by a different internal ND-primer, and amplification is isothermal and synergistic with respect to the number of primers employed. Amplification and detection kits are provided.

34 Claims, 9 Drawing Sheets

OTHER PUBLICATIONS

Afonina et al., "Minor Groove Binder-Conjugated DNA Probes for Quantitative DNA Detection by Hybridization-Triggered Fluorescence," BioTechniques, 2002, pp. 940-949, vol. 32.

An et al., "Characterization of a Thermostable UvrD Helicase and Its Participation in Helicase-dependant Amplification," The Journal of Biological Chemistry, 2005, pp. 28952-28958, vol. 280.

Asseline et al., "Nucleic acid-binding molecules with high affinity and base sequence specificity: Intercalating agents covalently linked to oligonucleotides," The Proceedings of the National Academy of Sciences, 1984, pp. 3297-3301, vol. 81.

Barany, "Genetic disease detection and DNA amplification using cloned thermostable ligase," The Proceedings of the National Academy of Sciences, 1991, pp. 189-193, vol. 88.

Blanco et al., "Highly Efficient DNA Synthesis by the Phage φ29 DNA Polymerase," The Journal of Biological Chemistry, 1989, pp. 8935-8940, vol. 264.

Gates et al., "Endonuclease V of *Escherichia coli*," The Journal of Biological Chemistry, 1977, pp. 1647-1653, vol. 252.

Kutyavin et al., "A novel endonuclease IV post-PCR genotyping system," Nucleic Acids Research, 2006, p. e128, vol. 34 (9 pages).

Notomi et al., "Loop-mediated isothermal amplification of DNA," Nucleic Acids Research, 2000, p. e63, vol. 28 (7 pages).

Oehlenschläger et al., "Detection of HIV-1 RNA by nucleic acid sequence-based amplification combined with fluorescence correlation spectroscopy," The Proceedings of the National Academy of Sciences, 1996, pp. 12811-12816, vol. 93.

Saba, "An Isothermal Nucleic Acid Amplification (Nick Displacement Amplification," The General Science Journal, 2004, retrieved from http://www.wbabin.net/saba/saba13.htm on Nov. 6, 2008 (49 pages).

Turner et al., "Harnessing asymmetrical substrate recognition by thermostable EndoV to achieve balanced linear amplification in multiplexed SNP typing," Biochemistry and Cell Biology, 2006, pp. 232-242, vol. 84.

Van Ness et al., "Isothermal reactions for the amplification of oligonucleotides," The Proceedings of the National Academy of Sciences, 2003, pp. 4504-4509, vol. 100.

Vincent et al., "Helicase-dependant isothermal DNA amplification," EMBO Reports, 2004, pp. 795-800, vol. 5.

Walker et al., "DNA detection by strand displacement amplification and fluorescence polarization with signal enhancement using DNA binding protein," Nucleic Acids Research, 1996, pp. 348-353, vol. 24.

Wu et al.,"the Ligation Amplification Reaction (LAR)—Amplification of Specific DNA Sequences Using Sequential Rounds of Template-Dependant Ligation," Genomics, 1989, pp. 560-569, vol. 4.

Yao et al., "Cleavage of Insertion/Deletion Mismatches, Flap and Pseudo-Y DNA Structures by Deoxyinosine 3'-Endonuclease from *Escherichia coli*," The Journal of Biological Chemistry, 1996, pp. 30672-30676, vol. 271.

Yao et al., "Further Characterization of *Escherichia coli* Endonuclease V," The Journal of Biological Chemistry, 1997, pp. 30774-30779, vol. 272.

Yao et al., "Interaction of Deoxyinosine 3'-Endonuclease from *Escherichia coli* with DNA Containing Deoxyinosine," The Journal of Biological Chemistry, 1995, pp. 28609-28616, vol. 270.

Yao et al., "Purification and Characterization of a Novel Deoxyinosine-specific Enzyme, Deoxyinosine 3'-Endonuclease, from *Escherichia coli*," The Journal of Biological Chemistry, 1994, pp. 16260-16268, vol. 269.

Yao et al., "Strand-specific Cleavage of Mismatch-containing DNA by Deoxyinosine 3'-Endonuclease from *Escherichia coli*," The Journal of Biological Chemistry, 1994, pp. 31390-31396, vol. 269.

\* cited by examiner

SEQUENCE LISTING

```
<160> NUMBER OF SEQ ID NOS: 23

<210> SEQ ID NO 1
<211> LENGTH: 23
<212> TYPE: DNA
<213> ORGANISM: Artificial sequence
<220> FEATURE:
<223> OTHER INFORMATION: oligo 1
<220> FEATURE:
<221> NAME/KEY: modified_base
<222> LOCATION: (12)..(12)
<223> OTHER INFORMATION: inosine at this position
<220> FEATURE:
<221> NAME/KEY: misc_feature
<222> LOCATION: (12)..(12)
<223> OTHER INFORMATION: n is a, c, g, or t

<400> SEQUENCE: 1
atcgagccct gncaaatgag gcc                                              23

<210> SEQ ID NO 2
<211> LENGTH: 23
<212> TYPE: DNA
<213> ORGANISM: Artificial sequence
<220> FEATURE:
<223> OTHER INFORMATION: oligo 2

<400> SEQUENCE: 2
ggcctcattt gtcagggctc gat                                              23

<210> SEQ ID NO 3
<211> LENGTH: 11
<212> TYPE: DNA
<213> ORGANISM: Artificial sequence
<220> FEATURE:
<223> OTHER INFORMATION: oligo 3

<400> SEQUENCE: 3
atcgagccct g                                                           11

<210> SEQ ID NO 4
<211> LENGTH: 10
<212> TYPE: DNA
<213> ORGANISM: Artificial sequence
<220> FEATURE:
<223> OTHER INFORMATION: oligo 4

<400> SEQUENCE: 4
aaatgaggcc                                                             10

<210> SEQ ID NO 5
<211> LENGTH: 23
<212> TYPE: DNA
<213> ORGANISM: Artificial sequence
<220> FEATURE:
<223> OTHER INFORMATION: oligo 5

<400> SEQUENCE: 5
atcgagccct gacaaatgag gcc                                              23
```

```
<210> SEQ ID NO 6
<211> LENGTH: 13
<212> TYPE: DNA
<213> ORGANISM: Artificial sequence
<220> FEATURE:
<223> OTHER INFORMATION: oligo 6
<220> FEATURE:
<221> NAME/KEY: modified_base
<222> LOCATION: (12)..(12)
<223> OTHER INFORMATION: inosine at this position
<220> FEATURE:
<221> NAME/KEY: misc_feature
<222> LOCATION: (12)..(12)
<223> OTHER INFORMATION: n is a, c, g, or t

<400> SEQUENCE: 6
atcgagccct gnc                                                        13

<210> SEQ ID NO 7
<211> LENGTH: 23
<212> TYPE: DNA
<213> ORGANISM: Artificial
<220> FEATURE:
<223> OTHER INFORMATION: oligo 7

<400> SEQUENCE: 7
ggcctcattt gccagggctc gat                                             23

<210> SEQ ID NO 8
<211> LENGTH: 264
<212> TYPE: DNA
<213> ORGANISM: Artificial Sequence
<220> FEATURE:
<223> OTHER INFORMATION: M13mp18 target sequence

<400> SEQUENCE: 8
tcttaatcta agctatcgct atgttttcaa ggattctaag ggaaaattaa ttaatagcga     60
cgatttacag aagcaaggtt attcactcac atatattgat ttatgtactg tttccattaa    120
aaaaggtaat tcaaatgaaa ttgttaaatg taattaattt tgttttcttg atgtttgttt    180
catcatcttc ttttgctcag gtaattgaaa tgaataattc gcctctgcgc gattttgtaa    240
cttggtattc aaagcaatca ggcg                                           264

<210> SEQ ID NO 9
<211> LENGTH: 26
<212> TYPE: DNA
<213> ORGANISM: Artificial sequence
<220> FEATURE:
<223> OTHER INFORMATION: primer 1
<220> FEATURE:
<221> NAME/KEY: modified_base
<222> LOCATION: (25)..(25)
<223> OTHER INFORMATION: inosine at this position
<220> FEATURE:
<221> NAME/KEY: misc_feature
<222> LOCATION: (25)..(25)
<223> OTHER INFORMATION: n is a, c, g, or t

<400> SEQUENCE: 9
ctcacatata ttgatttatg tactnt                                          26

<210> SEQ ID NO 10
<211> LENGTH: 23
<212> TYPE: DNA
<213> ORGANISM: Artificial sequence
<220> FEATURE:
<223> OTHER INFORMATION: probe cleavage enhancer
```

-continued

```
<400> SEQUENCE: 10
atttcatttg aattaccttt ttt                                            23

<210> SEQ ID NO 11
<211> LENGTH: 18
<212> TYPE: DNA
<213> ORGANISM: Artificial sequence
<220> FEATURE:
<223> OTHER INFORMATION: Endo IV probe

<400> SEQUENCE: 11
aaattaatta catttaac                                                  18

<210> SEQ ID NO 12
<211> LENGTH: 22
<212> TYPE: DNA
<213> ORGANISM: Artificial sequence
<220> FEATURE:
<223> OTHER INFORMATION: primer 2
<220> FEATURE:
<221> NAME/KEY: modified_base
<222> LOCATION: (21)..(21)
<223> OTHER INFORMATION: inosine at this position
<220> FEATURE:
<221> NAME/KEY: misc_feature
<222> LOCATION: (21)..(21)
<223> OTHER INFORMATION: n is a, c, g, or t

<400> SEQUENCE: 12
gatgatgaaa caaacatcaa na                                             22

<210> SEQ ID NO 13
<211> LENGTH: 19
<212> TYPE: DNA
<213> ORGANISM: Artificial sequence
<220> FEATURE:
<223> OTHER INFORMATION: primer 3
<220> FEATURE:
<221> NAME/KEY: modified_base
<222> LOCATION: (18)..(18)
<223> OTHER INFORMATION: inosine at this position
<220> FEATURE:
<221> NAME/KEY: misc_feature
<222> LOCATION: (18)..(18)
<223> OTHER INFORMATION: n is a, c, g, or t

<400> SEQUENCE: 13
cgatttacag aagcaagnt                                                 19

<210> SEQ ID NO 14
<211> LENGTH: 21
<212> TYPE: DNA
<213> ORGANISM: Artificial sequence
<220> FEATURE:
<223> OTHER INFORMATION: primer 4
<220> FEATURE:
<221> NAME/KEY: modified_base
<222> LOCATION: (20)..(20)
<223> OTHER INFORMATION: inosine at this position
<220> FEATURE:
<221> NAME/KEY: misc_feature
<222> LOCATION: (20)..(20)
<223> OTHER INFORMATION: n is a, c, g, or t

<400> SEQUENCE: 14
ttcaattacc tgagcaaaan a                                              21

<210> SEQ ID NO 15
<211> LENGTH: 27
<212> TYPE: DNA
```

```
<213> ORGANISM: Artificial sequence
<220> FEATURE:
<223> OTHER INFORMATION: primer 5
<220> FEATURE:
<221> NAME/KEY: modified_base
<222> LOCATION: (26)..(26)
<223> OTHER INFORMATION: inosine at this position
<220> FEATURE:
<221> NAME/KEY: misc_feature
<222> LOCATION: (26)..(26)
<223> OTHER INFORMATION: n is a, c, g, or t

<400> SEQUENCE: 15
gattctaagg gaaaattaat taatanc                                           27

<210> SEQ ID NO 16
<211> LENGTH: 12
<212> TYPE: DNA
<213> ORGANISM: Artificial sequence
<220> FEATURE:
<223> OTHER INFORMATION: primer 6
<220> FEATURE:
<221> NAME/KEY: modified_base
<222> LOCATION: (11)..(11)
<223> OTHER INFORMATION: inosine at this position
<220> FEATURE:
<221> NAME/KEY: misc_feature
<222> LOCATION: (11)..(11)
<223> OTHER INFORMATION: n is a, c, g, or t

<400> SEQUENCE: 16
gcgcagaggc na                                                           12

<210> SEQ ID NO 17
<211> LENGTH: 23
<212> TYPE: DNA
<213> ORGANISM: Artificial sequence
<220> FEATURE:
<223> OTHER INFORMATION: primer 7
<220> FEATURE:
<221> NAME/KEY: modified_base
<222> LOCATION: (22)..(22)
<223> OTHER INFORMATION: inosine at this position
<220> FEATURE:
<221> NAME/KEY: misc_feature
<222> LOCATION: (22)..(22)
<223> OTHER INFORMATION: n is a, c, g, or t

<400> SEQUENCE: 17
cttaatctaa gctatcgcta tnt                                               23

<210> SEQ ID NO 18
<211> LENGTH: 21
<212> TYPE: DNA
<213> ORGANISM: Artificial sequence
<220> FEATURE:
<223> OTHER INFORMATION: primer 8
<220> FEATURE:
<221> NAME/KEY: modified_base
<222> LOCATION: (20)..(20)
<223> OTHER INFORMATION: inosine at this position
<220> FEATURE:
<221> NAME/KEY: misc_feature
<222> LOCATION: (20)..(20)
<223> OTHER INFORMATION: n is a, c, g, or t

<400> SEQUENCE: 18
gattgctttg aagtaccaan t                                                 21

<210> SEQ ID NO 19
<211> LENGTH: 225
<212> TYPE: PRT
```

<213> ORGANISM: Thermatoga maritima

<400> SEQUENCE: 19

Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Tyr
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
        115                 120                 125

Phe Ile Glu Ile Pro Thr Ile Gly Val Ala Lys Ser Arg Leu Tyr Gly
    130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
        195                 200                 205

Pro Thr Arg Leu Ala His Ile Tyr Thr Gln Arg Leu Lys Lys Gly Leu
    210                 215                 220

Phe
225

<210> SEQ ID NO 20
<211> LENGTH: 225
<212> TYPE: PRT
<213> ORGANISM: Thermatoga maritima

<400> SEQUENCE: 20

Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Ala
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
        115                 120                 125

```
Phe Ile Glu Ile Pro Thr Ile Gly Val Ala Lys Ser Arg Leu Tyr Gly
        130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                    165                 170                 175

Ala Pro Ile Phe Val Ser Pro Gly His Leu Met Asp Val Glu Ser Ser
                180                 185                 190

Lys Arg Leu Ile Lys Ala Phe Thr Leu Pro Gly Arg Arg Ile Pro Glu
            195                 200                 205

Pro Thr Arg Leu Ala His Ile Tyr Thr Gln Arg Leu Lys Lys Gly Leu
        210                 215                 220

Phe
225

<210> SEQ ID NO 21
<211> LENGTH: 225
<212> TYPE: PRT
<213> ORGANISM: Thermotoga maritima

<400> SEQUENCE: 21

Met Asp Tyr Arg Gln Leu His Arg Trp Asp Leu Pro Pro Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
50                  55                  60

Lys Ile Leu Glu Val Val Ser Glu Arg Gly Glu Ile Thr Phe Pro Tyr
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala Ala Pro Arg Lys Leu Gly Ile Ala Ser His Met Gly Leu
        115                 120                 125

Phe Ile Glu Ile Pro Thr Ile Gly Val Ala Lys Ser Arg Leu Tyr Gly
        130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                    165                 170                 175

Ala Pro Ile Phe Val Ser Pro Gly His Leu Met Asp Val Glu Ser Ser
                180                 185                 190

Lys Arg Leu Ile Lys Ala Phe Thr Leu Pro Gly Arg Arg Ile Pro Glu
            195                 200                 205

Pro Thr Arg Leu Ala His Ile Tyr Thr Gln Arg Leu Lys Lys Gly Leu
        210                 215                 220

Phe
225

<210> SEQ ID NO 22
<211> LENGTH: 225
<212> TYPE: PRT
<213> ORGANISM: Thermotoga maritima
```

```
<400> SEQUENCE: 22

Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Tyr
65                  70                  75                  80

Ile Pro Gly Leu Leu Ala Phe Ala Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
            115                 120                 125

Phe Ile Glu Ile Pro Thr Ile Gly Val Ala Lys Ser Arg Leu Tyr Gly
        130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
        195                 200                 205

Pro Thr Arg Leu Ala His Ile Tyr Thr Gln Arg Leu Lys Lys Gly Leu
    210                 215                 220

Phe
225

<210> SEQ ID NO 23
<211> LENGTH: 225
<212> TYPE: PRT
<213> ORGANISM: Thermotoga maritima

<400> SEQUENCE: 23

Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Tyr
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
            115                 120                 125
```

-continued

```
Phe Ile Glu Ile Pro Thr Ile Gly Val Ala Ala Ser Arg Leu Tyr Gly
    130             135             140

Thr Phe Lys Met Pro Glu Asp Lys Arg Cys Ser Trp Ser Tyr Leu Tyr
145             150             155             160

Asp Gly Glu Glu Ile Ile Gly Cys Val Ile Arg Thr Lys Glu Gly Ser
                165             170             175

Ala Pro Ile Phe Val Ser Pro Gly His Leu Met Asp Val Glu Ser Ser
            180             185             190

Lys Arg Leu Ile Lys Ala Phe Thr Leu Pro Gly Arg Arg Ile Pro Glu
        195             200             205

Pro Thr Arg Leu Ala His Ile Tyr Thr Gln Arg Leu Lys Lys Gly Leu
    210             215             220

Phe
225
```

ACCELERATED CASCADE AMPLIFICATION (ACA) OF NUCLEIC ACIDS COMPRISING STRAND AND SEQUENCE SPECIFIC DNA NICKING

CROSS-REFERENCE TO RELATED APPLICATIONS

This application claims the benefit of priority to U.S. Provisional Patent Application Ser. No. 60/953,931, filed 3 Aug. 2007 and entitled "ISOTHERMAL STRAND-DISPLACEMENT AMPLIFICATION OF NUCLEIC ACIDS USING STRAND AND SEQUENCE SPECIFIC DNA NICKING," which is incorporated herein by reference in its entirety.

FIELD OF THE INVENTION

Aspects of the present invention relate generally to methods for amplification and detection nucleic acids (e.g., DNA an RNA), and more particularly to a novel amplification and detection methods comprising use of a reaction mixture having forward and reverse external nick-directing primers (ND-primers), at least one internal ND-primer, a strand-displacing DNA polymerase, a nick-directing endonuclease for strand-specific cleavage of ND-primer-extension products, and deoxynucleoside 5'-triphosphates, and incubating the reaction mixture with reagents, and under conditions suitable to provide for amplification of the amplifiable target sequence, wherein the amplification comprises primer extension, by least one internal ND-primer, of an external ND-primer extension product comprising the amplifiable target sequence or a portion thereof but lacking the respective external ND-primer sequence or a portion thereof. Particular aspects relate to amplification methods comprising use of a plurality of internal ND-primers, extension of one internal ND-primer extension product by a different internal ND-primer, wherein amplification is isothermal and synergistic with respect to the number of primers employed. Further aspects relate to isothermal strand-displacement amplification of nucleic acids referred to herein as Accelerated Cascade Amplification (ACA), and to nucleic acid amplification and detection kits.

Sequence Listing

A Sequence Listing in paper (.pdf) form and electronic (.txt) comprising SEQ ID NOS:1-23 is included as part of this application and is incorporated by reference herein in its entirety.

BACKGROUND

Early recognition of pathogens and genetic diseases, and susceptibility and/or predisposition thereto is vitally important in healthcare and, at least in part, depends on the ability to detect nucleic acids with accuracy and sensitivity. Not surprisingly, DNA and RNA detection methods are now routinely used for forensic, paternity, military, environmental and other testing applications. Optimally, the tests must be able to generate a detectable signal from samples that contain but a few copies of a nucleic acid of interest. Accordingly, nucleic acid amplification and detection technologies are of particular interest and importance.

PCR and LCR. PCR. The polymerase chain reaction (PCR) is by far the most widely used approach for increasing the concentration of a segment of target sequence in a mixture of DNA without cloning or purification (see, e.g., U.S. Pat. Nos. 4,683,195 and 4,683,202 to Mullis K. B., 1987). Briefly, PCR employs two oligonucleotide primers which are (i) complementary to opposite strands of a double-stranded target sequence and (ii) designed to bind (hybridize) to the respective target sequence such that extension of one primer with a DNA polymerase generates a template strand for the other primer. The DNA strands in PCR are separated by denaturation, in the presence of primers, at elevated temperatures (e.g., denaturation stage at >90° C.), followed by primer hybridization at an annealing temperature (e.g., annealing stage at ~55-65° C.) and primer extension. Because the thermostable DNA polymerases typically used in PCR exhibit maximum activity at temperatures of about 72-75° C., the primer extension may comprise a third "extension" stage at an optimal extension temperature to maximize the yield of PCR. In principle, when a quantitative yield of primer extension is achieved, the number of the DNA amplified strands is doubled after each cycle. The steps of denaturation, primer annealing, and polymerase extension can be repeated as often as needed to obtain relatively high concentrations of an amplified portion (amplicon) of the target sequence. Temperature cycling leads to rapid exponential growth of the target amplicon in accordance with the equation $$C_n = C_0(1+x)^n$$

wherein $C_0$ is the starting DNA concentration and n is the PCR cycle number and x is the average cycle yield (0 to 1) of strand replication. Where the PCR yield is quantitative or essentially quantitative (x>0.95-0.99), the desired PCR-amplified amplicons of the target sequence become the dominant sequences in the mixture after ~15-30 cycles, depending on the initial target DNA load. Although PCR has been widely accepted and implemented in molecular biology and DNA diagnostics, the method is yet limited by the requirement of the precise temperature-cycling apparatus, the need for hyper stable enzymes (e.g., polymerases), low multiplexing capabilities, and reaction contamination artifacts and concerns.

LCR. The ligase chain reaction (LCR) (e.g., Barany F., 1991; Wu D. Y. and Wallace R. B., 1989) is an alternative method for amplifying nucleic acids using temperature cycling. Briefly, LCR employs two pairs of self-complementary primers (or probes), the members of each pair hybridizing to respective, opposite (e.g., sense, antisense) target DNA strands, and wherein the members of each pair that hybridize to the same strand do so by hybridizing adjacent to each other on that respective strand, without gaps or mismatches. In this manner, two neighboring (adjacently hybridized) primers can be linked together by a ligase enzyme, providing a template sequence for the complementary LCR primers (also hybridizing adjacent to each other), such that repeated the cycles of denaturation, primer hybridization and ligation lead to amplification of a short segment of DNA. However, while the method has no polymerase extension requirement, there is still a requirement for cycling the between denaturation and annealing/ligation temperatures, and there is at some ability of the ligase to link two blunt-ended duplexes, leading to spontaneous, template-independent amplification that limits the applicability of LCR in detecting target nucleic acids at low concentrations.

Isothermal Amplification Technologies. Numerous attempts have been made to develop DNA amplification approaches, where the reaction does not require temperature cycling (e.g., Nucleic Acid Sequence Based Amplification (NASBA) (Davey C. and Malek L. T., 2000; Oehlenschlager F. et al, 1996), and Helicase-Dependent Amplification (HAD) (Vincent M. et al, 2004; An L. et al., 2005)). In typical isothermal amplification schemes, complementary DNA strands are separated by strand displacement during the primer extension stage, and thus require use of DNA polymerases that lack 5'-nuclease activity. Examples of such methods include Loop-Mediated Amplification (Notomi T. and Hase T., 2002; Notomi T. et al, 2000), Rolling-Circle Amplification (Lizardi P., 1998; Lizardi P. M. and Caplan M., 1998; Lizardi P. M., 2001a; Lizardi P. M., 2001b), along with various amplification methods based on use of RNA or composite RNA/DNA primers (Cleuziat P. and Mandrand B., 1998) including 5'-RNA-tailed composite primers (Kurn N., 2001; Kurn N., 2004; Kurn N., 2005) and Isothermal and Chimeric primer-initiated Amplification of Nucleic acids (ICAN) (Sagawa H. et al, 2003). All such amplification schemes are premised on having continuous DNA synthesis at a particular DNA site, which can be achieved by a number of ways including, for example, by a partial or complete by RNase H-mediated decomposition of the RNA segment of composite RNA/DNA primers; that is, after primer hybridization and extension by DNA polymerase, hydrolysis of the RNA segment of the primer promotes binding by another primer for subsequent extension and strand displacement. The RNA primer segment can be placed anywhere within the composite primer. In yet another approach, the 5'-segment of DNA primers are degraded using duplex-specific 5'-exonuclease activity (Mulrooney C. and Oultram J. D., 1999). The amplification methods that are based on partial or complete primer decomposition require a stage providing for a "fresh" primer re-annealing, wherein the remaining fragments of a previous primer have to dissociated or displaced by the fresh primer to restore the DNA priming site and support the cycling of the amplification reaction. This complicates the amplification mechanism and may slow down the reaction.

Alternatively, the primer need not be degraded, where the primer extension point can be rejuvenated via strand-specific DNA cleavage or nicking at a designated site. For example, Strand Displacement Amplification (SDA) (Walker G. T. et al, 1993; Walker G. T. et al, 1996; Fraiser M. S. et al, 1997; Walker G. T., 1998) is based on the use of a restriction enzyme to nick a hemi-modified recognition site. The method consists of a target generation process that makes copies of a target sequence that is flanked by nickable restriction sites. Amplification of these modified target sequences occurs through repeated nicking, strand displacement and extension at the restriction sites. The hemi-modified recognition sites are formed during the amplification where at least one of the four triphosphates is modified. Incorporation of modified nucleotides into amplification products blocks cleavage of the newly synthesized strands by restriction endonucleases that normally cleave both strands of double-stranded DNA.

Strand-specific cleavage of duplex DNAs is a key requirement for other reported amplification schemes (e.g. Oultram J. D. and Coutts J., 1999) and can be alternatively achieved by using recently discovered "nicking endonucleases" that cleave only one strand of a double-stranded DNA sequence. For example, Van Ness J. et al (Van Ness J. et al, 2003a; Van Ness J. et al, 2003b) suggested using the N BstNB enzyme that recognizes the 5'-GAGTC-3' sequence, and specifically cleaves the phosphodiester link four bases downstream on this strand. In contrast to SDA, the nicking endonuclease used is naturally strand specific so that there is no need to use modified nucleotide triphosphates to preclude cleavage of the other strand. However, the 3 to 7 nucleotides-long restriction recognition motifs of such nicking endonucleases limit applicability of the approach, and adapting the approach for amplification of any desired target DNA sequence requires complicating the system design by introducing additional oligonucleotides, primers and/or pre-amplification stages (see, e.g., Van Ness J. et al, 2003a; Van Ness J. et al, 2003b; Oultram J. D. and Coutts J., 1999).

Nick Displacement Amplification (NDA) (Saba J., 2004) is a form of isothermal amplification based on strand-specific nicking and strand displacement, and is regarded as a process for synthesizing a polynucleotide with complementarity to a duplexed target polynucleotide, containing a modification which appreciably influences nicking, comprising: (a) contacting a duplexed target with a nicking agent such that the non-target strand is selectively nicked at a prescribed location; (b) extending the 3'-ended fragment adjacent the nick with a polymerase such that the nicking site is rejuvenated and the 5'-ended strand adjacent the nick is displaced; and (c) repeating steps (a) and (b) such that there are multiple cycles of nicking, extension and displacement. NDA can be performed linearly and in a fashion similar to PCR wherein two primers, complementary to opposite DNA strands, are used and wherein extension of one primer generates a template for the other primer of the pair. FIG. 4, herein, shows a schematic representation of NDA. Similar to PCR, NDA is based on the use of two ND primers, one forward and one reverse primer, which are complementary to opposite strands of double stranded target and wherein extension of one primer generates template for the other primer. Shown is a scenario where amplification is initiated by a single-stranded target DNA (sense strand). An oligonucleotide primer (forward) incorporating a nick directing modification (ND) hybridizes to the target nucleic acid (stage A). A DNA polymerase recognizes the complex, and synthesizes a complementary strand (stage B). The product of primer extension is then recognized by a nick-directed nuclease (ND nuclease) that selectively cleaves the newly synthesized DNA strand (stage C) that contains the ND modification thereby restoring the primer structure. DNA polymerase once again extends the primer while displacing the DNA strand synthesized during the previous cycle (stage D). Sequential repetition of the stages B, C and D leads to perpetual accumulation of the strand displacement products. These amplification products have an indefinite 3'-ends, but identical 5'-sequences defined by design (location) of the forward ND primer and the cleavage specificity of ND nuclease employed. The cycling polymerase extension and ND nuclease nicking at the forward ND primer generates numerous extension products with indefinite ends, which are, in turn, targets for a second ND primer (reverse primer). Perpetual amplification from the reverse primer generates multiple DNA fragments with definite ends (corresponding to the forward primer-mediated nick site). The sequence of these extension products is identical to a target DNA sequence between the primer binding sites (excluding the primer sequences).

Practicing NDA is, however, limited by the requirement for a reliable way to nick only one of two DNA strands to restore the primer function in a cycling mode. The duplexed targets may originate from the priming of a target with a modified primer; for example, nicking modification may occur within the primer sequence that hybridizes to the target, wherein such nicking modification directs nicking within or adjacent to the primer (Id). The primer modifications can be nucleotide variants or mismatched nucleotides, recognized by mutant restriction enzymes or repair endonucleases. For example, the use of deoxyinosine (dI) modification in oligonucleotide primers is proposed for use as a nick-directing agent (Id), and it has been well established in the art that the certain endonucleases that initiate repair of dI lesions (see FIG. 1 herein), such as Endonuclease V from E. coli (Endo V), selectively cleave the dI-containing strand in DNA duplex at a site located 3' (downstream) from the lesion (see FIG. 2 herein).

Endo V from *E. coli* was first described by Gates and Linn (Gates F. T. III and Linn S., 1977), and later extensively characterized by Yao and co-workers (Yao M. et al, 1994; Yao M. and Kow Y. W., 1994; Yao M., Kow Y. W., 1995; Yao M., Kow Y. W., 1996; Yao M., Kow Y. W., 1997). Homologs of *E. coli* Endo V have been identified in a wide variety of organisms including archaebacteria, eubacteria and eukaryotes. Endo V analogs were also isolated from hyperthermophiles *Archaeoglobus fulgidus* (Liu J. et al, 2000), *Thermotoga maritima* (Huang J. et al, 2001; Huang J. et al, 2002), and mice (Moe A. et al, 2003). Deamination of adenosine in natural DNAs results in a dI-dT mismatch which may be repaired according to the pathway shown in FIG. 2 herein. However, such natural dI-dT mismatch repair does not provide a substrate primer for DNA polymerase because of the adjacent dI-dT mismatch; that is, the 3'-to-5'-Exo (endo) nuclease activity (aka, proof-reading activity) of a DNA polymerase degrades the 3'-nicked strand, and once the mutated dI-base is removed DNA integrity is restored by DNA extension and ligation). However, Endo V has also been shown to cleave complexes wherein dI forms a Watson-Crick base pair with dC. This property of the repair endonuclease makes dI containing primers useful in practicing NDA (see FIG. 3 herein). Unlike the case with nicking endonucleases, the use of deoxyinosine as a nick directing modification provides ample flexibility for NDA primer design with respect to any desired target nucleic acid sequence.

Millar D. S. et al have also disclosed an isothermal amplification reaction (Millar D. S. et al, 2006), which is similar to NDA in many aspects. Briefly, two oligonucleotide primers are designed in a fashion similar to PCR to provide isothermal amplification of nucleic acids in the presence of a strand displacing DNA polymerase, wherein the primers incorporate non-regular bases. Particular aspects comprise use of an enzyme that recognizes a non-regular base in double stranded DNA, and that causes a nick or excises a base in one DNA strand, at or near the site of the non-regular base, for DNA amplification substantially without thermal cycling. Similar to the case of NDA, Millar D. S. et al disclose numerous examples of non-regular bases (e.g., inosine) and respective enzymes (e.g., Endonuclease V, and variants thereof) that recognize the non-regular bases and cleave only one strand of duplex DNA to support the amplification reaction (Id).

In NDA (Saba J., 2004; Millar D. S. et al, 2006) and other NDA-related amplification schemes (Van Ness J. et al, 2003a; Van Ness J. et al, 2003b; Oultram J. D. and Coutts J., 1999), the nick directing primers do not need to dissociate and they can stay hybridized to the target nucleic acid indefinitely during the amplification while initiating numerous cycles of extension and strand displacement. This provides advantages over amplification schemes that are based on complete or partial degradation of the primer. Developers of ICAN made an attempt to adopt this advanced NDA format wherein RNA/DNA composite primers are not degraded, but rather restored by RNase H activity (e.g. Mukai H. et al, 2003). However, an advantage in this instance comes at the cost of having amplification primers terminated by ribonucleotides that are less efficiently extended by DNA polymerases than the DNA analogs.

Despite the isothermal aspects, the isothermal amplification methods including NDA (Saba J., 2004; Millar D. S. et al, 2006) and NDA-related methods (Van Ness J. et al, 2003a; Van Ness J. et al, 2003b; Oultram J. D. and Coutts J., 1999; Mukai H. et al, 2003) are limited because of reasons discussed herein, but primarily because of the relatively low amplification efficiency or amplification rate (e.g., Millar D. S. et al, 2006), There is therefore, a pronounced need in the art for more efficient and more rapid nucleic acid detection methods, including more efficient isothermal amplification methods that are not limited by the sequence of target nucleic acids of interest, multiplexing capabilities, choice of detection technology or requirements for post-amplification detection, sensitivity (i.e. minimum target load) and selectivity of amplification, and other factors and parameters that define the scope of the methods applicability in science and technology.

SUMMARY OF EXEMPLARY ASPECTS OF THE INVENTION

Particular aspects provide nucleic acid amplification and detection methods comprising: providing a reaction mixture containing a target nucleic acid with an amplifiable target sequence, forward and reverse external nick-directing primers (ND-primers), at least one internal ND-primer, a strand-displacing DNA polymerase, a nick-directing endonuclease for strand-specific cleavage of ND-primer-extension products, and deoxynucleoside 5'-triphosphates; and incubating the reaction mixture with reagents, and under conditions suitable to provide for amplification of the amplifiable target sequence, wherein the amplification comprises primer extension, by least one internal ND-primer, of an external ND-primer extension product comprising the amplifiable target sequence or a portion thereof but lacking the respective external ND-primer sequence or a portion thereof. Preferably, amplification comprises using a plurality of internal ND-primers, extension of one internal ND-primer extension product by a different internal ND-primer, and amplification is synergistic with respect to the number of primers employed. Preferably, amplification is isothermal amplification.

Certain aspects provide for isothermal strand-displacement amplification of nucleic acids by a method referred to herein as Accelerated Cascade Amplification (ACA).

Additional aspects provide nucleic acid amplification and detection kits for practicing the inventive methods The observed enhanced and synergistic amplification rate and/or efficiency of the disclosed ACA reactions were unexpected as described in detail herein below.

Specific, preferred aspects provide a method for amplification of a nucleic acid sequence, comprising: a) providing a reaction mixture comprising at least one target nucleic acid sequence having an amplifiable target sequence, a forward external nick-directing oligonucleotide primer (ND-primer) and a reverse external ND-primer, the external primers suitable to hybridize to the target nucleic acid sequence at nucleotide positions external to the amplifiable target sequence, at least one internal ND-primer suitable to hybridize to an external ND-primer extension product comprising the amplifiable target sequence or a portion thereof, but lacking a respective ND primer sequence or a portion thereof, a strand-displacing DNA polymerase suitable for primer extension of the hybridized primers, to provide respective primer-extension products, a nick-directing endonuclease suitable for strand-specific cleavage of the ND-primer-extension products to provide for primer-extension products lacking the respective ND-primers or portions thereof, and a mixture of deoxynucleoside 5'-triphosphates; and b) incubating the reaction mixture in the presence of reagents, and under reaction conditions suitable to support primer hybridization, DNA polymerase-mediated primer extension and strand displacement, and nick-directing endonuclease-mediated strand-specific cleavage of the extension products, to provide for amplification of the amplifiable target sequence, wherein the amplification comprises primer extension, by least one internal ND-primer, of an external ND-primer extension product comprising the amplifiable target sequence or a portion thereof but lacking the respective external ND-primer sequence or a portion thereof. In particular preferred aspects, a plurality of internal ND-primers are used, and the amplification comprises primer extension, by least one internal ND-primer, of an extension product of a different internal ND-primer lacking the respective different internal ND-primer sequence or a portion thereof. Certain embodiments comprise use of at least one forward internal ND-primer, and at least one reverse internal ND-primer. In particular embodiments, the plurality of internal ND-primers comprises a nested set of progressively more internal, internal ND-primers. In certain aspects, the nested set of internal ND-primers comprises both forward and reverse internal ND-primers. In particular aspects, the number of internal ND-primers used is a number equal to or greater than 2. In certain embodiments, the number of internal ND-primers used is a number in the range from 1 to 8. In particular embodiments, at least one of the ND-primers incorporates at least one of a deoxyinosine and a deoxyuridine nucleoside as a nick-directing modification, and wherein the nick-directing nuclease comprises Endonuclease V.

Preferably, the amplification rate or efficiency is enhanced relative to amplification mediated by use of the external ND-primers only. In certain aspects, the enhancement is synergistic with respect to the number of primers employed. In particular aspects, the concentration of the extension products of an internal ND-primer N, per unit reaction time, is approximated by the general formula $$C_N = C_0 \cdot K^N \cdot t^N$$

as discussed and defined herein below in working Example 4.

In certain preferred aspects of the methods, amplification comprises or consists of isothermal amplification. In particular embodiments, the isothermal amplification is performed at a temperature in the range of about 15° C. to about 80° C., or in the range of about 45° C. to about 75° C.

In certain aspects, the target nucleic acid is single-stranded, or the target nucleic acid is double-stranded, and wherein prior to, or during, the amplification reaction the double-stranded target nucleic acid is rendered single-stranded. In particular embodiments, the target nucleic acid is DNA. In certain aspects, the target nucleic acid is RNA, or at least one DNA copy of the RNA is synthesized using a reverse transcriptase prior to amplifying the amplifiable target DNA sequence. In certain aspects, at least one ND-primer incorporates more than one nick-directing modification.

In particular aspects of the methods, at least two of the ND-primers incorporate different nick-directing modifications, and the reaction mixture comprises respective nick-directing endonucleases providing for cleavage of ND-primer extension products comprising the different nick directing modifications. Certain aspects of the methods, comprise use of an ND-primer precursor that cannot serve as a primer in amplification of the amplifiable target sequence, and at least one of the ND-primers is generated during amplification by cleavage of the ND-primer precursor by a nick-directing endonuclease.

In particular aspects (e.g., multi-plexing), the reaction mixture comprises a plurality of target nucleic acids, and a respective plurality of amplifiable target sequences is amplified by use of respective sets of ND-primers. In certain embodiments, the amplification comprises whole genome amplification, wherein a plurality of amplifiable target sequences is amplified by use of respective sets of ND-primers.

In certain aspects of the methods, at least one of the ND-primers contains at least one structural modification other than a nick-directing modification. In particular embodiments, the structural modification comprises at least one duplex-stabilizing modification selected from one or more modified nucleotides, and a tail conjugated to the 5'-end of the ND-primer. In particular aspects, the tail is at least one of an intercalator and a minor groove binder.

In particular aspects, detecting the target nucleic acid comprises use of a detecting agent that interacts with amplification products to provide for a signal, and wherein detection of the signal is indicative of at least one of the presence, and the amount of the target nucleic acid in the reaction mixture. In certain preferred aspects, the detecting agent comprises a fluorescent agent or oligonucleotide probe that changes its fluorescence properties upon interaction with the amplification products. In particular embodiments, the detecting agent or probe comprises a FRET probe that changes its fluorescent properties upon forming a complementary complex with the amplification products. In certain aspects, the FRET probe comprises a hybridization-triggered FRET probe, or comprises a cleavable FRET probe (e.g., wherein the cleavable FRET probe comprises an Endonuclease IV-cleavable probe and the reaction mixture additionally incorporates Endonuclease IV).

In certain preferred aspects, the strand-displacing DNA polymerase has no 3'→5' nuclease activity. In particular embodiments, the nick-directing endonuclease comprises a nuclease with cleavage cycling capability, providing for cleavage of greater than 1, greater than 5, or greater than 10 ND-primer extension products per minute under the reaction conditions.

In particular preferred embodiments, the Endonuclease V used is that of *Thermotoga maritima* (SEQ ID NO:19), a variant thereof, or a mutant thereof selected from a group consisting of Y80A (SEQ ID NO:20), H116A (SEQ ID NO:21), R88A (SEQ ID NO:22) and K139A (SEQ ID NO:23).

In additional embodiments, at least one ND-primer is immobilized on a solid support. In certain aspects, at least one of the ND-primers is designed using specialty computer software.

Certain method embodiments further comprise detecting the amplified target sequence by at least one of post-amplification detection, and real-time detection.

Additional aspects provide a method for detection of a nucleic acid sequence in a sample, comprising: obtaining a sample comprising at least one target nucleic acid sequence having an amplifiable target sequence; amplifying the amplifiable target sequence according the herein-described methods; and detecting the amplified target sequence by at least one of post-amplification detection, and real-time detection.

Further aspects provide a kit for use in amplifying or detecting a nucleic acid sequence, comprising: at least one forward external nick-directing oligonucleotide primer (ND-primer) and at least one reverse external ND-primer, the external primers suitable to hybridize to a target nucleic acid sequence at nucleotide positions external to a amplifiable target sequence of the target nucleic acid; and at least one internal ND-primer suitable to hybridize to an external ND-primer extension product comprising the amplifiable target sequence or a portion thereof, but lacking a respective external ND primer sequence or a portion thereof. In certain embodiments, the kits further comprise at least one of a strand displacing DNA polymerase and a nick-directing endonuclease. In particular embodiments, the kits comprise a plurality of internal ND-primers, wherein at least one internal ND-primer is suitable to hybridize to an extension product of a different internal ND-primer lacking the respective different internal ND-primer sequence or a portion thereof. In certain aspects, the kit comprises at least one forward internal ND-primer, and at least one reverse internal ND-primer. In certain kit aspects, the plurality of internal ND-primers comprises a nested set of progressively more internal, internal ND-primers. In particular kit aspects, the nested set of internal ND-primers comprises both forward and reverse internal ND-primers. In certain kit embodiments, the number of internal ND-primers used is a number equal to or greater than 2, or is a number in the range from 1 to 8. In certain preferred kit embodiments, at least one of the ND-primers incorporates at least one of a deoxyinosine and a deoxyuridine nucleoside as a nick-directing modification.

DETAILED DESCRIPTION OF EXEMPLARY EMBODIMENTS

Figure 1:
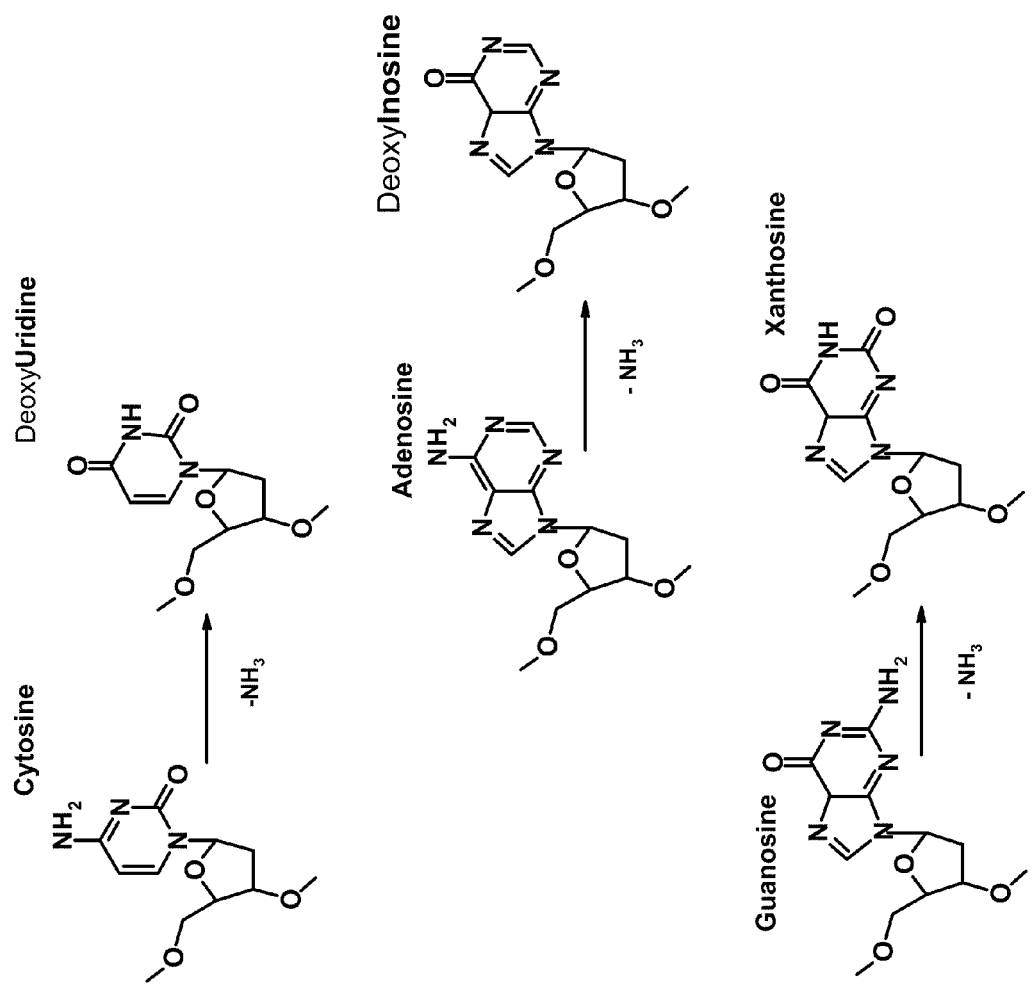
FIG. 1 shows art-recognized structures of mutant nucleosides that appear in DNA as result of base deamination.
Figure 2:
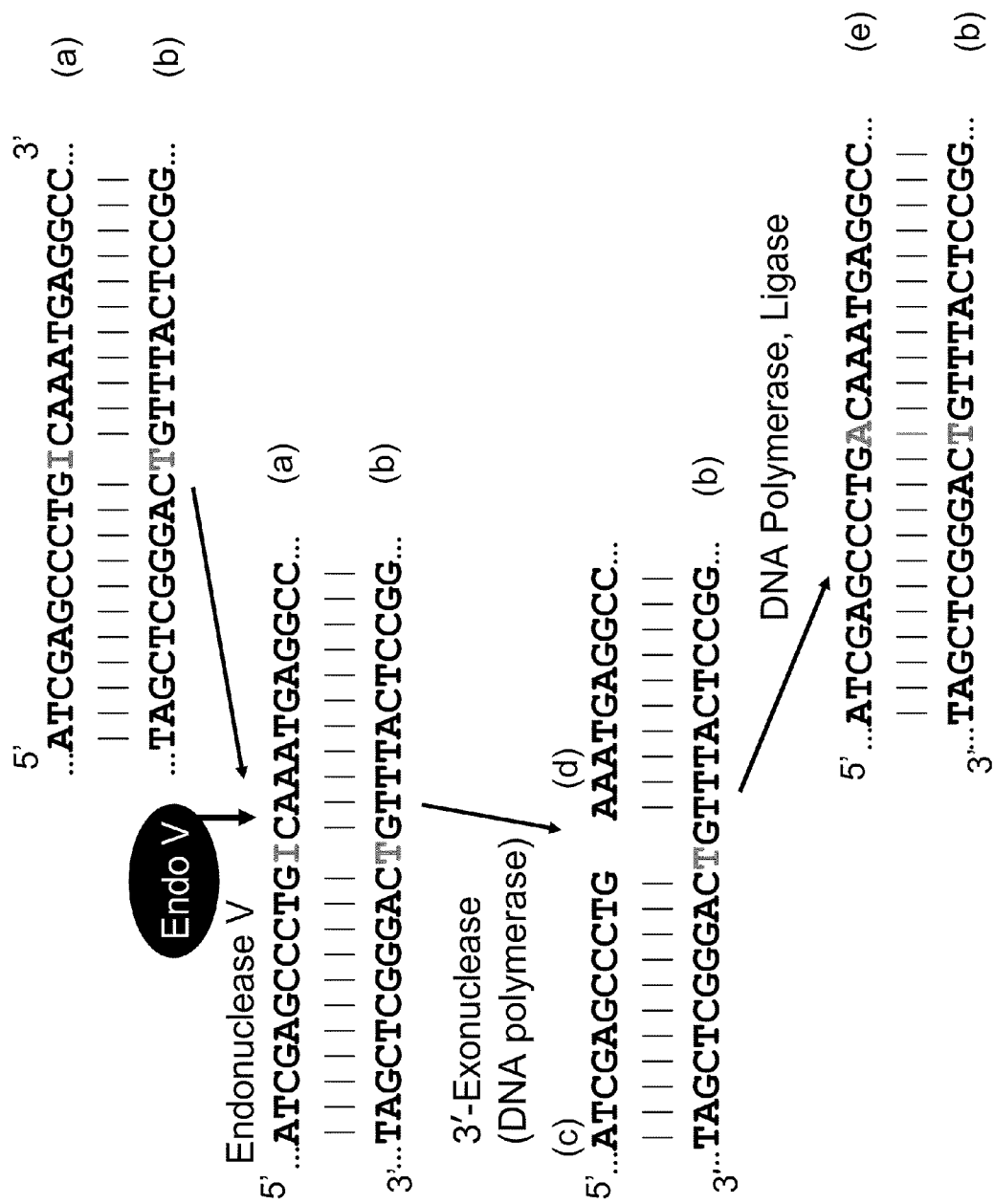
FIG. 2 shows a probable mechanism of deoxyinosine (dI) lesion repair, which is based on activity of an inosine 3'-endonuclease (Endo V). The nuclease recognizes the deoxyinosine containing strand and nicks it at the second phosphodiester bond on the 3'-side of the inosine base. The nicked complex is a poor substrate for DNA polymerase, because of the close proximity of the 3'-terminal dI/dT-mismatch. The 3'-to-5'-Exo (endo) nuclease activity of a DNA polymerase (aka, proof-reading activity) degrades the 3'-nicked strand to remove the mutated dI-base, and the DNA integrity is restored by DNA polymerase-mediated extension, and subsequent ligation. The nucleic acid sequences (a), (b), (c), (d) and (e) correspond to SEQ ID NOS:1-5, respectively.
Figure 3:
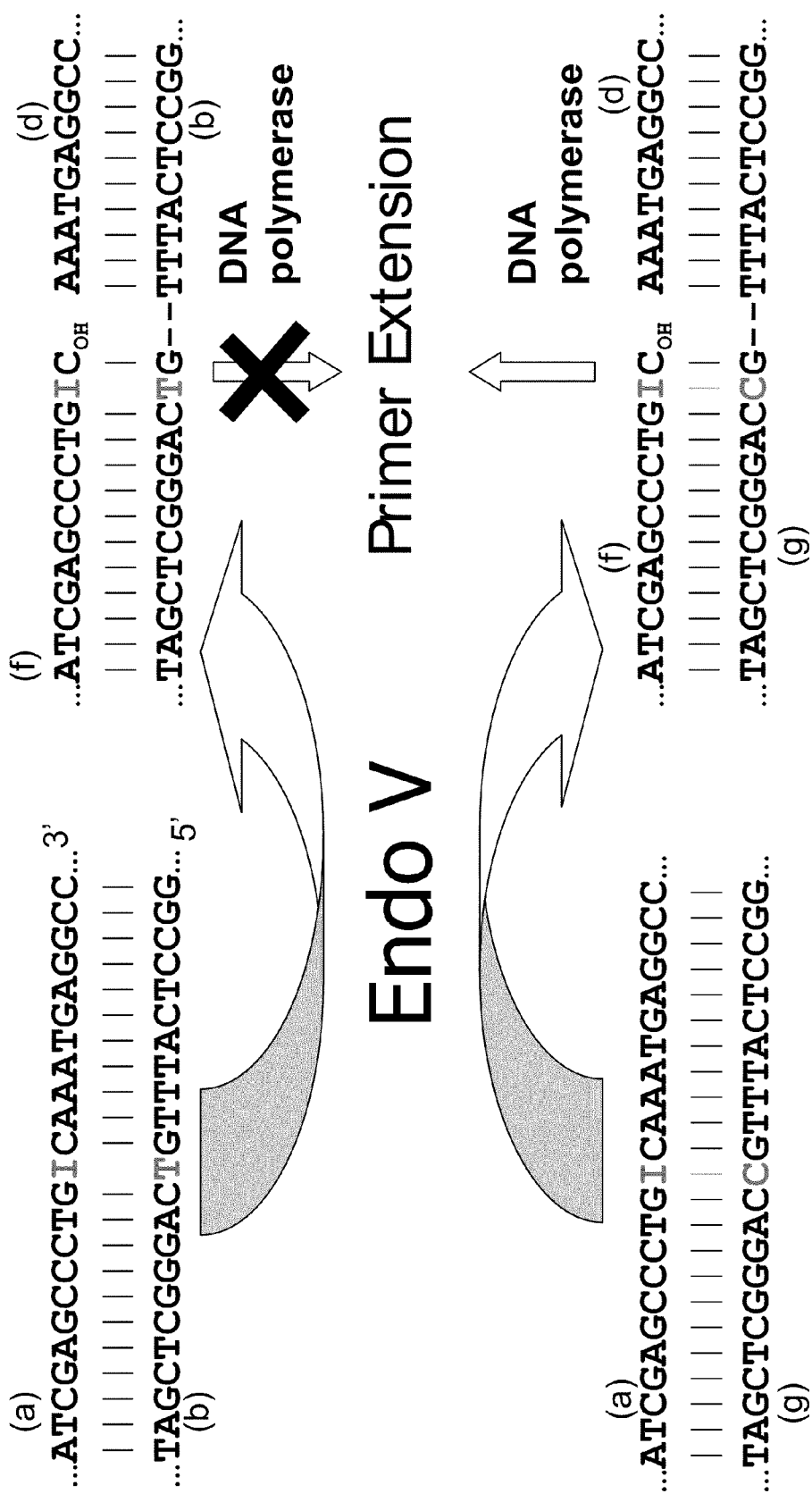
FIG. 3 illustrates products of cleavage of Watson-Crick matched and mismatched dI-containing duplexes by an inosine 3'-endonucleases. Adenosine deamination in natural DNAs coincides with formation of a mismatched, dI/dT-base pair (top portion of FIG. 3), cleavage of which does not provide a substrate (primer) for DNA polymerase due to the close proximity of the dI/dT mismatch to the nicked 3'-end, whereas nicking of the matched, dI/dC-base pair duplex (bottom) does provide an effective substrate (primer) for DNA polymerase. The nucleic acid sequences (a), (b), (d), (f) and (g) correspond to SEQ ID NO:1, SEQ ID NO:2, SEQ ID NO:4, SEQ ID NO:6 and SEQ ID NO:7, respectively.

Particular aspects provide nucleic acid amplification and detection methods comprising: providing a reaction mixture containing a target nucleic acid with an amplifiable target sequence, forward and reverse external nick-directing primers (ND-primers), at least one internal ND-primer, a strand-displacing DNA polymerase, a nick-directing endonuclease for strand-specific cleavage of ND-primer-extension products, and deoxynucleoside 5'-triphosphates; and incubating the reaction mixture with reagents, and under conditions suitable to provide for amplification of the amplifiable target sequence, wherein the amplification comprises primer extension, by least one internal ND-primer, of an external ND-primer extension product comprising the amplifiable target sequence or a portion thereof but lacking the respective external ND-primer sequence or a portion thereof. Preferably, amplification comprises using a plurality of internal ND-primers, extension of one internal ND-primer extension product by a different internal ND-primer, and amplification is synergistic with respect to the number of primers employed. Preferably, amplification is isothermal amplification.

Certain aspects provide for isothermal strand-displacement amplification of nucleic acids by a method referred to herein as Accelerated Cascade Amplification (ACA).

Additional aspects provide nucleic acid amplification and detection kits for practicing the inventive methods The observed enhanced and synergistic amplification rate and/or efficiency of the disclosed ACA reactions were unexpected as described in detail herein below.

DEFINITIONS

Terms and symbols of biochemistry, nucleic acid chemistry, molecular biology and molecular genetics used herein follow those of standard treaties and texts in the field (e.g., Sambrook J. et al, 1989; Kornberg A. and Baker T., 1992; Gait M. J., ed., 1984; Lehninger A. L., 1975; Eckstein F., ed., 1991, and the like). To facilitate understanding of particular exemplary aspects of the invention, a number of terms are discussed below.

In particular aspects, "sample" refers to any substance containing or presumed to contain a nucleic acid of interest. The term "sample" thus includes but is not limited to a sample of nucleic acid, cell, organism, tissue, fluid, for example, spinal fluid or lymph fluid, or substance including but not limited to, for example, plasma, serum, urine, tears, stool, respiratory and genitourinary tracts, saliva, semen, fragments of different organs, tissue, blood cells, samples of in vitro cell cultures, isolates from natural sources such as drinking water, microbial specimens, and objects or specimens that have been suspected to contain nucleic acid molecules.

In particular aspects, "target nucleic acid" or "nucleic acid of interest" refers to a nucleic acid or a fragment of nucleic that is to be amplified and/or detected using methods of the present invention. Nucleic acids of interest can be of any size and sequence; e.g. as big as genomic DNA. Preferably, the nucleic acid is of a size that provides for amplification thereof. For many methods of the invention, nucleotide sequences of target nucleic acids are, or preferably are known. However, in certain embodiments, the invention may be applied when sequence of target nucleic acids are unknown. For example, the present invention may be used for purpose of whole genome amplification (WGA) using a plurality of short ND primers (e.g. 6-8-mers). The goal of WGA is to amplify whole DNA contained in a sample up to a microgram level while respecting the original sequence representation. In certain aspects of WGA, the origin and sequence of nucleic acids may not be known. Two or more target nucleic acids can be fragments or portions of the same nucleic acid molecule. As used herein, target nucleic acids are different if they differ in nucleotide sequence by at least one nucleotide. In this aspect, the invention may be used to detect "polymorphic variations" wherein, for example, two nucleic acids of interest have significant degree of identity in the sequence but differ by only a few nucleotides (e.g. insertions, deletions) or by a single nucleotide, or single nucleotide polymorphism (SNP). Target nucleic acids can be single-stranded or double-stranded. When nucleic acid of interest is double-stranded or presumed to be double-stranded, the term "target nucleic acid" refers to a specific sequence in either strand of double-stranded nucleic acid. Therefore the full complement to any single stranded nucleic acid of interest is treated herein as the same (or complementary) target nucleic acid. Prior to applying methods of the invention, double-stranded nucleic acids of interest may be rendered completely or partially single-stranded using any physical, chemical or biological approach; e.g., denaturation at elevated temperatures (e.g., >90° C.), enzymatic digestion, etc. Either strand of a double-stranded nucleic acid may be referred toherein as a "sense" strand while another (complementary) strand may be referred to as an "antisense" strand. This definition may, for example, be used only for purpose of distinguishing two strands to facilitate the discussion, and it does not necessarily, absent further information, assign to the nucleic acid strand any special property. Amounts of nucleic acids of interest isolated from different sources are too low to enable direct detection. Therefore, the target nucleic acids are usually amplified, for example, using methods of the present invention. When a nucleic acid of interest is RNA, it may be converted prior to Accelerated Cascade Amplification" ("ACA"; as defined herein below) to DNA/RNA heteroduplexes or to duplex cDNA by known methods (e.g., Simpson D. et al (1988) and the like), employing a "reverse transcriptase" activity of enzymes that can extend an oligonucleotide primer hybridized to a RNA template providing synthesis of complementary DNA (cDNA) in the presence of deoxynucleoside 5'-triphosphates (dNTPs).

In certain aspects, target nucleic acids of the invention comprise polynucleotides comprising natural and/or modified nucleotides that support the complementary DNA strand synthesis initiated by oligonucleotide primers in the presence of DNA polymerase and nucleoside 5'-triphosphates. Nucleic acids are known to accumulate structural modifications due to nucleophilic, photochemical, radical and other chemical reactions of the nucleotides; for example, abasic sites or nucleotides with modified bases that do not participate in Watson-Crick pairing with natural nucleotides (e.g., xanthosine). Many of these structural modifications may not completely block the DNA synthesis, but at a certain density and/or location, they can render the target nucleic acid unamplifiable. The term "an amplifiable target sequence" refers to a target nucleic acid that, regardless of structural modifications, supports the synthesis of at least one copy of the target sequence of interest that can be further amplified by methods of the invention. In this aspect, the amplification products of the invention may not necessarily reflect the exact sequence of the target nucleic acid because of the structural modifications in the nucleic acids sample.

In particular aspects, "Amplification" and "amplifying" target nucleic acids, in general, refers to a procedure wherein multiple copies of the nucleic acid of interest are generated in the form of DNA copies.

In particular aspects, "amplicon" or "amplification product" refers to a primer extension product or products of amplification that may be a population of polynucleotides, single- or double-stranded, that are replicated from either strand or from one or more nucleic acids of interest. For example, Accelerated Cascade Amplification (ACA) methods of the invention typically result in amplification products of variable length and state. Regardless of the originating target nucleic acid strand and the amplicons state, e.g. double- or single-stranded, all amplicons which are usually homologous are treated herein as amplification products of the same target nucleic acid including the products of incomplete extension. Similar to PCR, "Nick Displacement Amplification" ("NDA", as discussed herein) and other amplification techniques, the amplicon sequences in ACA are generally defined by the oligonucleotide primers which are designed to hybridize to specific sequences of nucleic acids of interest such that the amplified target products represent target sequences located between binding sites of forward and reverse ND primers. Amplicons of the invention may or may not incorporate ND primers. Amplicons of the invention may additionally contain certain structural nucleotide modifications other than ND modifications, if their presence is required or useful for providing amplification products with special or improved properties; e.g. enhanced hybridization properties.

In particular aspects, the terms "complementary" or "complementary" are used herein in reference to the polynucleotides base-pairing rules. Double-stranded DNA, for example, consists of base pairs wherein, for example, G forms a three hydrogen bond complex, or pairs with C, and A forms a two hydrogen bond complex, or pairs with T, and it is regarded that G is complementary to C, and A is complementary to T. In this sense, for example, an oligonucleotide 5'-GATTTC-3' is complementary to the sequence 3'-CTAAAG-5'. Complementarity may be "partial" or "complete." In partial complementarity only some of the nucleic acids bases are matched according to the base pairing rules. The degree of complementarity between nucleic acid strands has significant effects on the strength of hybridization between nucleic acids. This is particularly important in performing amplification and detection reactions that depend upon nucleic acids binding. The terms may also be used in reference to individual nucleotides and oligonucleotide sequences within the context of polynucleotides. As used herein, the terms "complementary" or "complementarity" refer to the most common type of complementarity in nucleic acids, namely Watson-Crick base pairing as described above, although the oligonucleotide components and amplification products of the invention may participate, including an intelligent design, in other types of "non-canonical" pairings like Hoogsteen, wobble and G-T mismatch pairing.

In particular aspects, the term "homology" and "homologous" refers to a degree of identity between nucleic acids. There may be partial homology or complete homology.

In particular aspects, the term "secondary structure" refers to an intermolecular complex formation of one sequence in a polynucleotide with another sequence in the same polynucleotide due to complete or partial complementarity between these two sequences. Unless specified otherwise, the term "complex" means the same as "duplex" and it represents a double-stranded fragment or portion of a nucleic acid formed on the principal rules of the Watson-Crick base pairing. The terms "hairpin" structure or "stem-loop" structure may be also used herein describing elements of secondary structure and both terms refer to a double-helical region (stem) formed by base pairing between complementary sequences in a single strand RNA or DNA.

In particular aspects, "isothermal amplification" and "isothermal amplification reaction" refers to a process which generates multiple copies of a target nucleic acid, and which, unlike PCR, does not require temperature changes (temperature cycling) during the amplification, and which may rather be conducted at a relatively steady or relatively constant temperature. Reaction temperature in isothermal amplification, including in methods of the invention may fluctuate somewhat, but is not required for the purpose of amplicon strand separation as in PCR.

"PCR" is an abbreviation of term "polymerase chain reaction," the art-recognized nucleic acid amplification technology (e.g., U.S. Pat. Nos. 4,683,195 and 4,683,202 to Mullis K. B.). The commonly used PCR protocol employs two oligonucleotide primers, one for each strand, designed such that extension of one primer provides a template for the other primer in the next PCR cycle. Generally, a PCR reaction consists of repetitions (or cycles) of (i) a denaturation step which separates the strands of a double-stranded nucleic acid, followed by (ii) an annealing step, which allows primers to anneal to positions flanking a sequence of interest, and then (iii) an extension step which extends the primers in a 5' to 3' direction, thereby forming a nucleic acid fragment complementary to the target sequence. Each of the above steps may be conducted at a different temperature using an automated thermocycler. The PCR cycles can be repeated as often as desired resulting in an exponential accumulation of a target DNA amplicon fragment whose termini are usually defined by the 5'-ends of the primers used. Particular temperatures, incubation times at each step and rates of change between steps depend on many factors well-known to those of ordinary skill in the art and the examples can be found in numerous published protocols (e.g., McPherson M. J. et al. (1991 and 1995) and the like). Although conditions of PCR can vary in a broad range, a double-stranded target nucleic acid is usually denatured at a temperature of >90° C., primers are annealed at a temperature in the range of about 50-75° C., and the extension is preferably performed in the 72-7° C. range. The term "PCR" encompasses derivative forms of the reaction, including but not limited to, "RT-PCR," "real-time PCR," "nested PCR," "quantitative PCR," "multiplexed PCR," "asymmetric PCR" and the like.

Figure 4:
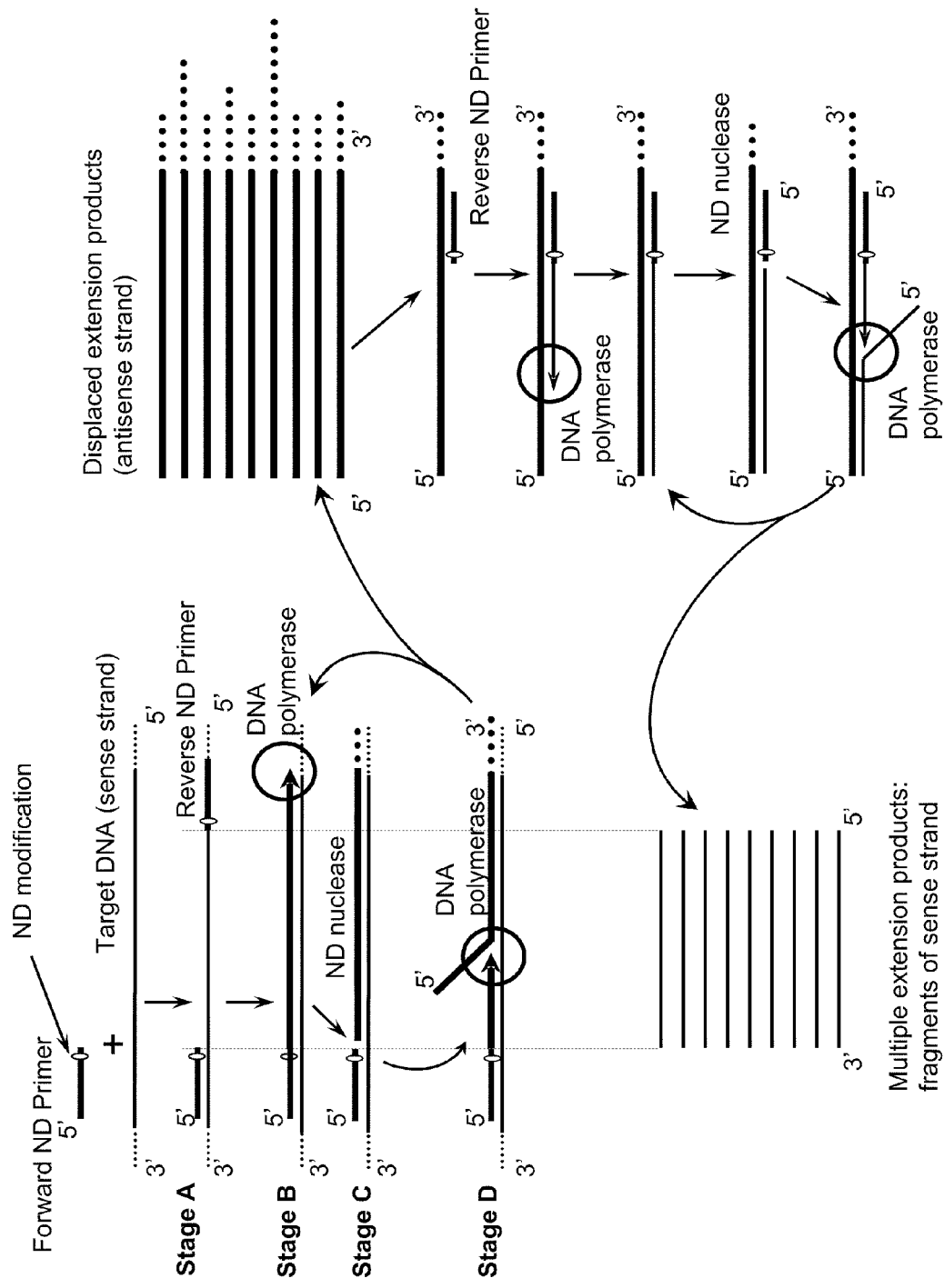
FIG. 4 shows schematic representation of a Nick Displacement Amplification (NDA) as described in Saba J. (2004). Similar to PCR, NDA is based on use of two ND primers, one forward and one reverse primer, which are complementary to opposite strands of double stranded target and wherein extension of one primer generates template for another primer. In this scenario, the oligonucleotide primers incorporate a nick-directing (ND) modification.

The term "Nick Displacement Amplification" ("NDA") refers to an isothermal amplification that is based on use of two "nick displacement" or "nick directing" ("ND") primers (e.g., as described in Saba J., 2004). ND primers incorporate a modification usually located near the primer's 3'-end. After hybridization with target nucleic acid and primer extension by strand displacing DNA polymerase, ND nuclease cleaves the strand incorporating the ND modification at the 3'-side and restores the priming function. The reaction of cleavage and extension cycles provide for amplification of nucleic acid of interest. FIG. 4 herein illustrates NDA amplification of a single-stranded target DNA using two ND primers. Other aspects of NDA may be found in Millar D. S. et al, 2006; Van Ness J. et al, 2003a; Van Ness J. et al, 2003b and similar disclosures.

Figure 5:
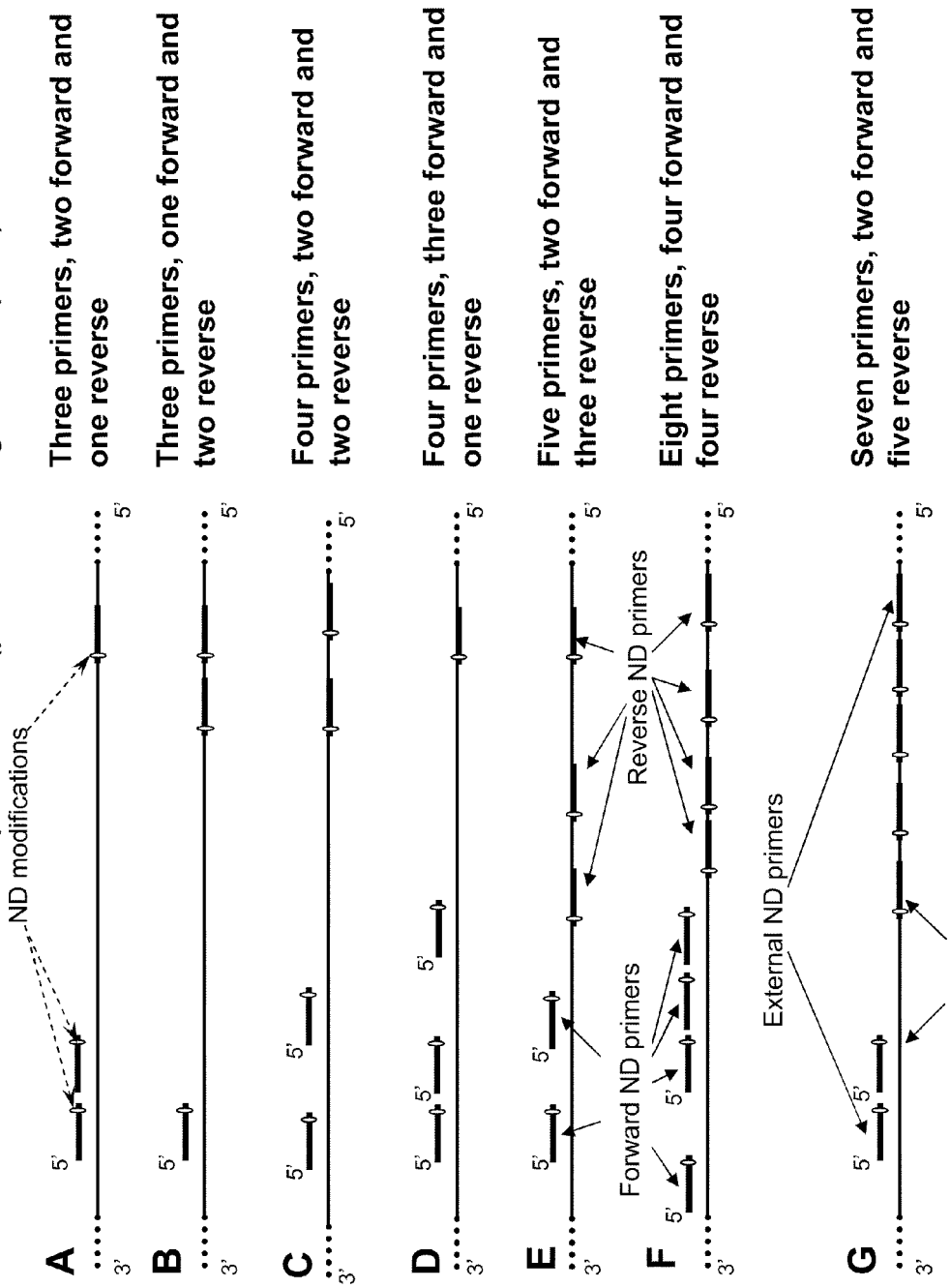
FIGS. 5A-5G show, according to particular exemplary aspects of the present invention, various system designs (A-E) of the inventive Accelerated Cascade Amplification (ACA) methods. Unlike PCR and NDA, ACA employs three or more nick directing (ND) primers (or the use of three or more appropriately disposed primer binding sites that can be occupied by one or more primers). Reverse ND primers are shown as fragments/portions of the target nucleic acid strand. The number of forward and reverse primers employed may be equal (examples C and F) or different (examples A, B, D and G). ND primers in ACA are designed such that products of extension of any forward ND primer serve as templates for any reverse ND primer used, and vice versa.

According to particular aspects of the present invention, the term "Accelerated Cascade Amplification" ("ACA") refers to an isothermal amplification of the present invention which is based on use of at least three nick directing (ND) primers (or the use of three or more appropriately disposed primer binding sites that can be occupied by one or more ND primers). ACA reactions may incorporate additional primers that have no ND modification. The number of ND primers (or the number of appropriately disposed primer binding sites that can be occupied by one or more ND primers) in ACA is unlimited. In preferred aspects the number of ND primers used is equal to or greater than: 1; 2; 3; 3; 4; 5; 6; 7; 8; 9; 10; 15; 20; 25; 30; 40; 50; 70; 80; or 100. In particular aspects, the number of ND primers used is in a range from about 3 to about 10. In certain aspects, ND primers represents a "plurality of primers" that represents a plurality of different sequences, and that can be of the same or different length. A plurality of ND primers is particularly useful when ACA is used for purpose of whole genome amplification (WGA). In certain aspects, at least one ND primer is a forward ND primer, while others are reverse or vice versa. ND primer sequences in ACA are selected such that extension of any forward ND primer serves as a template for any reverse ND primer applied and vice versa. Examples of ND primer designs for ACA are shown in FIG. 5. In these aspects, the ND primers are regarded as "designed to provide Accelerated Cascade Amplification." It will be appreciated by those of ordinary skill in the art that the present invention encompasses embodiments wherein fewer than three ND primers may provide for ACA. For example, the same ND primer designed to be complementary to one nucleic acid strand may have two primer binding sites within its extension product. Such a scenario is treated herein as three different ND primers even though these three different ND primer functions are provided by the same oligonucleotide. Unlike in PCR, NDA and other amplification technologies, reaction speed in ACA can be controlled by the number of ND primers used (see, e.g., working EXAMPLE 1 herein).

The term "Whole Genome Amplification" ("WGA") refers to the art-recognized method commonly applied to amplify genomic DNAs up to a microgram level while preserving the original sequence representation. Unlike methods of sequence specific amplification, wherein the goal is to amplify a certain fragment of a target nucleic acid, whole genome amplification aims to amplify all DNA molecules in the sample. The method is based on use of random hexanucleotide primers providing multiple displacement amplification reactions using denatured DNA as template. Examples of WGA may be found, e.g., in Blanco L. et al, (1989). In certain aspects, ACA methods of the present invention are applied for whole genome amplification.

As used herein, the term "nuclease" refers to an enzyme which expresses a phosphomonoesterase or phosphodiesterase activity and capable of cleaving a phosphorester bond in compounds such as R'—O—P(O)(OH)$_2$ and R'—O—P(O)(OH)—O—R" resulting in products R'—OH+ P(O)(OH)$_3$ and R'—OH+P(O)(OH)$_2$—O—R" (or R"—OH+ P(O)(OH)$_2$—O—R'), respectively and wherein R' and R" may be moieties of any structure which are not necessarily of a nucleotide nature. The term "nucleases" incorporates both "exo" and "endo" nucleases.

In particular aspects, the terms "nick directing endonuclease" or "nick directing nuclease" ("ND nuclease") refer to a nuclease that cleaves one strand of a double-stranded nucleic acid containing a nick directing modification at or near the modification such that extension of the cleaved strand by DNA polymerase does not eliminate the nick directing modification, thus supporting repetitive cycling of the cleavage and DNA extension reactions. ND nucleases which recognize and cleave nucleic acids at the 3'-sites from the "nick directing modifications" are preferred ND endonucleases in practicing methods of the invention. The ND nucleases of the invention are preferably duplex specific but they may cleave nucleic acids incorporating nick directing modifications when these nucleic acids are in single-stranded state. For example, Endonuclease V used herein as a preferred ND nuclease is known to be able to cleave single-stranded DNA polymers incorporating deoxyinosine and deoxyuridine modifications. Preferably, ND nucleases of the invention selectively cleave nucleic acids containing ND modifications at least 10-times more efficiently than regular nucleic acid with no ND modifications. ND nucleases of the invention are essentially free or express very little "general" duplex specific or single-strand specific nuclease activity so that they do not cleave oligonucleotide components and target nucleic acids unless these oligonucleotide components or target nucleic acids incorporate ND modifications. The term "duplex specific nuclease" refers in general to an enzyme that recognizes specific DNA duplex structures and cleaves these structures, e.g. 5'-flap endonucleases. The term "single strand specific nuclease" refers to an enzyme that recognizes and cleaves nucleic acids in single-strand state. In a preferred embodiment of the invention, ND primers incorporate deoxyinosine or deoxyuridine modifications which are recognized and cleaved by Endonuclease V, or a functional variant thereof. As used herein, the term Endonuclease V (Endo V) encompasses functional variants thereof, including any nuclease that having enzymatic activity (cleavage specificity and/or activity) of the Endonuclease V from *Escherichia coli*, which preferentially hydrolyzes the second phosphodiester bond in the DNA strand on the 3' side of a deoxyinosine or deoxyuridine modification). In a preferred embodiment of the invention, the Endonuclease V is that *Thermotoga maritima* (SEQ ID NO:19) of a mutant Endonuclease V from *Thermotoga maritima* selected from a group of Y80A (SEQ ID NO:20), H116A (SEQ ID NO:21), R88A (SEQ ID NO:22) and K139A (SEQ ID NO:23) mutants. Additional mutants encompassed by the present invention are described in U.S. Pat. No. 7,198,894, which is incorporated herein by reference. Certain nucleases other than ND nucleases may be used in practicing methods of the invention, in particular, for nucleic acid detection by real-time detection.

DNA polymerases isolated from natural sources may generally have two types of duplex specific nuclease activities, 5'→3' and 3'→5' nuclease activities. DNA polymerases with 5'→3' nuclease activity cleave nucleic acid duplex at or near the 5'-end, whereas DNA polymerases with 3'→5' nuclease activity, also known as proofreading activity, cleave nucleic acid duplex at or near its 3'-end. As used herein, the term "strand displacing DNA polymerase" refers to DNA polymerases that essentially lack 5'→3' nuclease activity and are capable of displacing downstream DNA encountered during synthesis. Strand displacing DNA polymerases are preferably used in methods of the present invention. The strand displacing DNA polymerases of the invention may or may not have 3'→5' nuclease activity. Preferred DNA polymerases have no associated nuclease activity, including 3'→5' nuclease activity.

The term "nick directing modifications" ("ND modifications") has very broad meaning and it refers to any approach or structural entity or combination thereof within oligonucleotides or polynucleotides, including target nucleic acids and products of amplification, which direct ND nucleases to cleave only one of two duplex strands, usually but not necessarily the strand incorporating the nick directing modification. In this aspect, the term "nick directing modification" incorporates, for example, certain aspects of strand specific cleavage disclosed in SDA (Walker G. T. et al, 1993; Walker G. T. et al, 1996; Fraiser M. S. et al, 1997; Walker G. T., 1998). Examples of nick-directing modifications include but are not limited to nucleotide sequences which commonly comprise natural deoxynucleotides representing binding and cleavage sites of strand-specific nucleases also known as "nicking endonucleases" (e.g. Nb.BbvCI, Nb.BsmI, Nb.BsrDI, Nb.BtsI, Nt.AlwI, Nt.BbvCI, Nt.BspQI, Nt.BstNBI and Nt.CviPII), RNA nucleotides or RNA fragments incorporated into composite RNA/DNA primers (Cleuziat P. and Mandrand B., 1998; Kurn N., 2001; Kurn N., 2004; Kurn N., 2005; Sagawa H. et al, 2003), wherein RNase H serves as a ND nuclease. Modified deoxynucleotide dI and dU are additional preferred examples of ND modifications that are recognized and cleaved in DNA duplexes by Endonuclease V. In certain aspects, ND modifications may also be any residues or moieties that are not of a nucleotide nature. Other examples of nick-directing modification include but are not limited to those that are described, for instance, in publications of Saba J. (2004) and Millar D. S. et al (2006), which are incorporated herein by reference. ND modifications of the invention may be located anywhere within the respective ND primer sequence and the optimal location is usually defined by the type of the particular ND modification(s) used.

As used herein, "nick directing primer" or "ND primer" refers to an oligonucleotide primer that incorporates a "nick directing modification." Nick directing primers may occur naturally in nucleic acids incorporating certain ND modifications, for example, 5-methyl cytosine, inosine, deoxyuridine, etc. Some ND primers may be named herein as "forward" ND primers while other primers are named "reverse" ND primers. Unless indicated otherwise, this terminology does not necessarily assign to the primers any special property and it is used for the purpose of distinguishing the oligonucleotide primers in discussion. For example, when one or more ND primers are named forward primers and they complementary to, e.g. a sense target strand, then the term reverse primers apply to ND primers which are complementary to an antisense target strand and to the products of the forward primers extension. The terms "internal" and "external" are used herein for the purpose of distinguishing two or more ACA primers that are made complementary to the same target strand (see, e.g., FIG. 5G herein) such that an external primer hybridizes to a target strand at the 5' side of an internal primer bound to the same strand.

As used herein, the terms "nick directing primer precursor," "nick directing precursor" or "ND precursor" refers to oligonucleotides or polynucleotides that incorporate one or more ND primers. The precursor or precursors may be used in methods of the invention to generate one or more ND primers by cleavage of the precursors during the isothermal amplification. The ND precursor may or may not serve as a primer in methods of the invention.

In certain preferred embodiments of the present invention, detection of the target nucleic acids can be performed in "real-time" or "real time." Real time detection is possible when all detection components are available during the amplification and the reaction conditions such as temperature, buffering agents to maintain pH at a selected level, salts, co-factors, scavengers, and the like support both stages of the reaction, amplification and the detection. This permits a target nucleic acid to be measured as the amplification reaction progresses decreasing the number of subsequent handling steps required for the detection of amplified material. "Real-time detection" means an amplification reaction for which the amount of reaction product, i.e. target nucleic acid, is monitored as the reaction proceeds. Real-time amplification is distinguished primarily in the detecting chemistries for monitoring the target nucleic acids in the reaction, for example, Tyagi et al (1999; incorporated herein by reference) use hybridization-triggered FRET probes ("Molecular Beacons"). The Endo IV assay described in (Kutyavin I. V. et al, 2004; Kutyavin I. V. et al, 2006) is yet another example of the detection technologies that may be used to detect the amplicons of the present invention in real time. Reviews of the detection chemistries for real-time amplification can be also found in Didenko V. V., 2001, Mackay I. M. et al, 2002, and Mackay J., Landt O., 2007, which are incorporated herein by reference. In preferred embodiments of the present invention, detection of nucleic acids is based on use of FRET effect and FRET probes.

In certain aspects, the amplification and detection stages of the invention may be performed separately, not in real time, when the detection stage follows the amplification. The terms "detection performed after the amplification" and "post-amplification detection" are used herein to describe such assays.

"Multiplexed amplification" refers to an amplification reaction wherein multiple target nucleic acids are simultaneously amplified.

"Polynucleotide" and "oligonucleotide" are used herein interchangeably and each means a linear polymer of nucleotide monomers. Polynucleotides typically range in size from a few monomeric units, e.g. 5-40, when they are usually referred to as "oligonucleotides," to several thousand monomeric units. The exact size will depend on many factors, which in turn depends on the ultimate function or use of the oligonucleotide. The oligonucleotides may be generated in any manner, including chemical synthesis, DNA replication, reverse transcription, or a combination thereof. Whenever a polynucleotide or oligonucleotide is represented by a sequence of letters, for example, "CCGTATG," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine. Usually DNA polynucleotides comprise these four deoxyribonucleosides linked by phosphodiester linkage whereas RNA comprises uridine ("U") in place of "T" for the ribose counterparts.

The term "natural nucleosides" as used herein refers to four deoxynucleosides which may be commonly found in DNAs isolated from natural sources. Natural nucleosides are deoxyadenosine, deoxycytidine, deoxyguanosine, and deoxythymidine. The term also encompasses their ribose counterparts, with uridine in place of thymidine.

As used herein, the terms "unnatural nucleosides" or "modified nucleotides" refer to nucleoside analogs that are different in their structure from those natural nucleosides for DNA and RNA polymers. Some of the naturally occurring nucleic acids of interest may contain nucleosides that are structurally different from the natural nucleosides defined above, for example, DNAs of eukaryotes may incorporate 5-methyl-cytosine and tRNAs are notorious for harboring many nucleoside analogs. However, as used herein, the terms "unnatural nucleosides" or "modified nucleotides" encompasses these nucleoside modifications even though they can be found in natural sources. For example, ribothymidine and deoxyuridine are treated herein as unnatural nucleosides. Certain modified nucleotides are used in the invention as "nick directing modifications." Examples include but not limited to deoxyinosine and deoxyuridine.

The term "oligonucleotide component" refers to any molecule of polynucleotide nature that is required or helpful in conducting either amplification or detection reaction of the invention or both. Oligonucleotide components include but not limited to oligonucleotide primers, e.g. ND primers of the invention, probes, hybridization and cleavage enhancers, effectors, etc. Oligonucleotide components can be labeled or have structural modifications of any kind.

The term "oligonucleotide primer" refers to a single-stranded DNA or RNA molecule that hybridizes to a target nucleic acid and primes enzymatic synthesis of a second nucleic acid strand in presence of a DNA polymerase. In this case, as used herein, the target nucleic acid "serves as a template" for the oligonucleotide primer.

As used herein, the term an "oligonucleotide probe" refers to an oligonucleotide component which is used to detect amplification products of the present invention. The oligonucleotide probes of the invention may incorporate detectable elements like labels, e.g. dye, mass tag, etc. In preferred embodiments, the oligonucleotide probes contain two dyes which are in a FRET interaction and wherein hybridization of the probes with amplified target nucleic acids results in a detectable fluorescent signal. These probes may be also referred herein as "FRET probes." Similar to ND primers, the oligonucleotide probes of the present invention may be "modified" or contain "structural modifications" that, for example, enhance their hybridization properties, improve the binding or cleavage specificity, etc.

The term "structural modifications" refers to any chemical substances such as atoms, moieties, residues, polymers, linkers or nucleotide analogs which are usually of a synthetic nature and which are not commonly present in natural nucleic acids. As used herein, the term "structural modifications" also include nucleoside or nucleotide analogs which rarely present in natural nucleic acid including but not limited to inosine (hypoxanthine), 5-bromouracil, 5-methylcytosine, 5-iodouracil, 2-aminoadenosine, 6-methyladenosine, preudouridine and the like. Certain structural modifications may be used in the invention as nick directing modifications.

"Duplex-stabilizing modifications" refer to structural modifications, the presence of which in double-stranded nucleic acids provides a duplex-stabilizing effect when compared in thermal stability, usually measured as Tm, with respective nucleic acid complexes that have no structural modification and comprised natural nucleotides. Duplex-stabilizing modifications are structural modifications that are most commonly applied in synthesis of oligonucleotide probes and primers. Duplex-stabilizing modifications are commonly represented by modified nucleotides that can be "universal" bases (Burgner D. et al, 2004) and 'tails' like intercalators and minor groove binders.

"Hybridizing," "hybridization" or "annealing" refers to a process of interaction between two or more polynucleotides forming a complementary complex through base pairing which is most commonly a duplex or double stranded complex as originally described in Doty P. et al (1960). The stability of a nucleic acid duplex is measured by the melting temperature, or "$T_m$." "melting temperature" or "Tm" means the temperature at which a complementary complex of nucleic acids, usually double-stranded, becomes half dissociated into single strands. These terms are also used in describing stabilities of polynucleotide secondary structures wherein two or more fragments of the same polynucleotide interact in a complementary fashion with each other forming complexes, usually hairpin-like structures.

"Hybridization properties" of a polynucleotide means an ability of this polynucleotide or its fragment to form a sequence specific complex with another complementary polynucleotide or its fragment. "Hybridization properties" is also used herein as a general term in describing the complementary complex stability. In this aspect, "hybridization properties" are similar in use to yet another term, "melting temperature" or "Tm." "Improved" or "enhanced hybridization properties" of a polynucleotide refers to an increase in stability of a complex of this polynucleotide with its complementary sequence due to any means including but not limited to a change in reaction conditions such as pH, salt concentration and composition, for example, an increase in magnesium ion concentration, presence of complex stabilizing agents such as intercalators or minor groove binders, etc., conjugated or not. The hybridization properties of a polynucleotide or oligonucleotide can also be altered by an increase or decrease in polynucleotide or oligonucleotide length. The cause of the hybridization property enhancement is generally defined herein in context.

"Detecting agent" refers to any molecule or particle which associates with nucleic acids in a specific fashion and wherein this association complex may be detected by any physical, chemical or biological means. The most commonly used detecting agents are intercalating dyes and fluorescent agents. For example, amplification products in PCR can be detected using intercalating dyes as described by Wittwer C. T. et al in U.S. Pat. Nos. 6,174,670 and 6,569,627.

The term "label" refers to any atom or molecule that can be used to provide a detectable signal and that can be attached to a nucleic acid or oligonucleotide. Labels include but are not limited to isotopes, radiolabels such as $^{32}P$; binding moieties such as biotin; haptens such as digoxygenin; luminogenic, mass tags, phosphorescent or fluorescent moieties, fluorescent dyes alone or in combination with other dyes or moieties that can suppress or shift emission spectra by FRET effect. Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable. The term "FRET-labeled" refers an oligonucleotide probe which usually incorporates two dyes that are in a FRET interaction. A FRET-labeled oligonucleotide may incorporate but one fluorescent dye, but in this context it is understood herein that the fluorescence of the dye conjugated to an oligonucleotide is suppressed by a means other than a quenching dye, e.g. fluorescence of fluorescein is reduced in the presence of neighboring guanosines.

"Fluorescent label" refers to a label that provides fluorescent signal. A fluorescent label is commonly a fluorescent dye, but it may be any molecule including but not limited to a macromolecule like protein, or a particle made from inorganic material like quantum dots, as described in (Robelek R. et al, 2004).

"FRET" is an abbreviation of Förster Resonance Energy Transfer effect. FRET is a distance-dependent interaction occurring between two dye molecules in which excitation is transferred from a donor to an acceptor fluorophore through dipole-dipole interaction without the emission of a photon. As a result, the donor molecule fluorescence is quenched, and the acceptor molecule becomes excited. The Efficiency of FRET depends on spectral properties, relative orientation and distance between the donor and acceptor chromophores (Förster T., 1965). In the case of random dipole orientation, and a good overlap between emission spectrum of the donor and absorption spectrum of the acceptor, the efficiency of FRET is dependent on the inverse sixth power of the intermolecular separation (Clegg R. M., 1992; Clegg R. M., 1995; Selvin P. R., 1995). This makes FRET useful over distances comparable to the dimensions of biological macromolecules (Stryer L. and Haugland R. P., 1967) and this effect is widely used in biomedical research and particularly in probe designs for nucleic acid detection (Didenko V. V., 2001).

As used herein, "FRET probe" refers to a fluorescent oligonucleotide which is used for detection of a nucleic acid of interest wherein detection is based on FRET effect. The FRET probe commonly contains two chromophores. The acceptor chromophore is usually a non-fluorescent dye chosen to quench fluorescence of the reporting fluorophore (Eftink M. R., 1991).

A "reaction mixture" generally means a solution containing all the necessary reactants for performing an amplification or detection reaction or both.

The term "reaction vessel" refers to any kind of a container used to perform the amplification and/or detection reactions of the methods of the invention and wherein the term "reaction vessel" means any appropriate way of isolation of the reaction mixture from the environment. A "reaction vessel" may be made from any solid material, including but not limited to, plastic, glass, quartz, metal, etc. The reaction vessels may be of any size, wherein the reaction volume may be measured in nanoliter, microliter, milliliter or liter scales. The reaction vessels can be of any shape, e.g. tubes or plates wherein multiple reaction vessels are combined in one plate. The reaction vessels may be made from a liquid material wherein, for example, aqueous drops of the reaction mixtures of the invention are suspended and floating in oil. The term "reaction vessel" also includes a micro-fluidic or fluidic card made from any material, usually plastic, and wherein the card comprises reaction chambers and channels allowing mixing the reaction components in an order or simultaneously as required by the methods of the invention.

As used herein, the term "kit" refers to any system for delivering materials. In the context of reaction assays, such delivery systems include elements allowing the storage, transport, or delivery of reaction components such as oligonucleotides, buffering components, additives, reaction enhancers, enzymes and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

The term "solid support" refers to any material that provides a solid structure with which another material can be attached. Such materials may include but not limited to silicon, plastic, metal, glass, ceramic surfaces, and the like. Solid supports may be of a rigid or non-rigid nature like gels, rubbers, polymers, etc. and may be any type of shape including spherical shapes like beads. Certain embodiments of the present invention have at least one of the reaction components such as, e.g. ND primer, oligonucleotide probe, or modified amplicon immobilized on solid support at amplifying or detecting stages or both. A biological material is "immobilized" to a solid support when it is associated with the solid support through a random or non-random chemical or physical interaction. The immobilization or attachment may be through a covalent bond using specialty spacer molecule or linker group. However, the immobilization need not be covalent or permanent.

As used herein, "detection assay" or "assay" refers a reaction or chain of reactions that are performed to detect nucleic acids of interest. The assay may comprise multiple stages including amplification and detection reactions performed consequently or in real time, nucleic acid isolation and intermediate purification stages, immobilization, labeling, etc. The terms "detection assay" or "assay" encompass a variety of derivative forms of the methods of the invention, including but not limited to, a "post-amplification assay" when the detection is performed after the amplification stage, a "real time assay" when the amplification and detection are performed simultaneously, a "FRET assay" when the detection is based using FRET effect, "immobilized assay" when one of either amplification or detection oligonucleotide components or an amplification product is immobilized on solid support, and the like.

The term "assay design" has broad meaning related to any, sometimes not necessarily to a particular, method of the invention including all reaction conditions (e.g. temperature, salt, pH, enzymes, oligonucleotide component concentrations, etc.), structural parameters (e.g. length and position of ND primers and probes, design of specialty sequences, etc.) and assay derivative forms (e.g. post-amplification, real time, immobilized, FRET detection schemes, etc.) chosen to amplify and/or to detect the nucleic acids of interest.

Isothermal Amplification of Target Nucleic Acids:

Particular aspects of the present invention provide methods for isothermal amplification of a target nucleic acid, comprising providing a reaction mixture having a target nucleic acid, at least three nick directing primers (or the use of three or more appropriately disposed primer binding sites that can be occupied by one or more ND primers), a strand displacing DNA polymerase, a nick-directing endonuclease, and a mixture of deoxynucleoside 5'-triphosphates; and incubating the reaction mixture under conditions suitable to support hybridization of the nick directing primers with the target nucleic acid, primer extension, strand displacement and strand-specific cleavage of the extension products by the nick directing nuclease in a cycling mode, wherein Accelerated Cascade Amplification (ACA) of the target nucleic acid is provided.

Target nucleic acids, or nucleic acids of interest are preferably single-stranded. ACA of the invention is initiated when ND primers hybridize to single-stranded nucleic acid forming a substrate for extension by DNA polymerase. When target nucleic acids are double-stranded, they are rendered single stranded by any physical, chemical or biological approach before applying the methods of the invention. For example, double-stranded nucleic acid can be denatured at elevated temperature, e.g. 90-95° C. The target nucleic acids may be derived from any organism or other source, including but not limited to prokaryotes, eukaryotes, plants, animals, and viruses, as well as synthetic nucleic acids. The target nucleic acids may be DNA, RNA, and/or variants thereof. Nucleic acids of interest can be isolated and purified from the sample sources before applying methods of the present invention. Preferably, the target nucleic acids are sufficiently free of proteins and any other substances interfering with amplification and/or detection reactions. Many methods are available for the isolation and purification of nucleic acids of interest including commercial kits and specialty instruments. For example, nucleic acids can be isolated using organic extraction with a phenol/chloroform reagent followed by ethanol precipitation (Ausubel F. M et al, eds., 1993). Solid phase adsorption method (Walsh P. S. et al, 1991; Boom W. R. et al, 1993) and salt-induced DNA precipitation (Miller S. A. et al, 1988) are yet other known approaches to purify nucleic acids. In a preferred embodiment, the target nucleic acid is DNA. In another embodiment, the target nucleic is RNA. Prior to applying the methods of the invention, a DNA copy (cDNA) of target RNA can be obtained using an oligonucleotide primer that hybridize to the target RNA, and extending of this primer in the presence of a reverse transcriptase and nucleoside 5'-triphosphates. The resulting DNA/RNA heteroduplex can then be rendered single-stranded using techniques known in the art, for example, denaturation at elevated temperatures. Alternatively, the RNA strand may be degraded in presence of RNase H nuclease. The oligonucleotide primer used in synthesis of the DNA copy may or may not be a nick-directing primer (ND primer). In certain aspects, target RNA may be used directly to initiate ACA. For example, the oligonucleotide primer used in synthesis of cDNA may be a ND primer, incorporating deoxyinosine or deoxyuridine nucleotides. Endonuclease V may cleave the extended primer in the resulted DNA/RNA heteroduplex, thus initiating the synthesis of other target DNA copies through cycles of cleavage, strand displacement and extension.

Many amplification reactions described to date are based on the use of two oligonucleotide primers designed to be complementary to opposite strands of a target nucleic acid such, such that extension of one primer provides a template for another primer. Examples include PCR (Mullis K. B. et al, 1987; Mullis K. B., 1987), NASBA (Davey C. and Malek L. T., 2000; Oehlenschlager F. et al, 1996), HAD (Vincent M. et al, 2004; An L. et al., 2005), amplification methods based on the use of RNA or composite RNA/DNA primers (Cleuziat P. and Mandrand B., 1998; Sagawa H. et al, 2003), SDA (Walker G. T. et al, 1993; Walker G. T. et al, 1996; Fraiser M. S. et al, 1997; Walker G. T., 1998), NDA (Saba J., 2004; Millar D. S. et al, 2006) and other amplification reactions.

Accelerated Cascade Amplification (ACA) of the present invention is different in this aspect; that is, ACA is based on the use of at least three oligonucleotide primers that incorporate nick directing modifications. In preferred embodiment, the ACA reaction mixtures comprise of more than three ND primers. The number of ND primers in ACA depends on many factors and it is generally unlimited. In yet another embodiment, the ND primers of the invention represent a plurality of primers. A plurality of ND primers is especially useful when ACA is used for the purpose of whole genome amplification (WGA) (Blanco L. et al, 1989). For example, a plurality of all possible hexa-, hepta- or octanucleotide primers incorporating deoxyinosine or deoxyuridine nucleotide may be prepared, and these primer mixtures may be applied for WGA using Endonuclease V as a nick directing endonuclease. ACA reaction mixtures may additionally incorporate primers that have no ND modifications. ND primers creating the plurality of primers for WGA may vary in length, and may be prepared by chemical synthesis or produced otherwise. The sequence of ND primers may be known or unknown or random. For example, a nucleic acid may be amplified by known techniques, e.g. PCR, in the presence of deoxyinosine or deoxyuridine 5'-triphosphates in a mixture with four natural dNTPs. The amplification product then may be cleaved in the presence of Endonuclease V, generating a plurality of ND primers that can be used in methods of the invention for WGA and other purposes.

In certain embodiments, only one or two oligonucleotide ND primers are used, but in such instances, the target nucleic acid must provide for two external ND primer binding sites and at least one internal ND primer binding site that can be occupied by the one or two ND primerst to provide for ACA.

When the target nucleic acid sequence is known and a particular target fragment needs to be amplified, the number of ND primers employed for ACA amplification is generally less than that used in WGA. As shown in the working Examples herein, the amplification speed of ACA depends on the number of ND primers applied. However, the probability of priming at nucleic acid sites other than the target sequence may increase proportionally with the number of ND primers used in ACA. This, in turn, may lead to synthesis and amplification of undesired sequences that compete with and/or contaminate the target amplicons. The cost of the ACA reactions is also reflective of the number of ND primers used. Those of ordinary skill in the art will appreciate that optimal system design, including the number of ND primers may be determined for individual implementations of the invention to address the above arguments and concerns, while achieving rapid and efficient ACA amplification. The design of ND primers to provide ACA preferably incorporates the following rules: at least one ND primer in ACA design is a reverse primer while others are forward primers, or vice versa; ND primer sequences in ACA are selected such that extension of any forward ND primer provides a template for any reverse ND primer applied, and vice versa; any strand of double-stranded nucleic acid may be amplified by the same set of ND primers designed to provide ACA.

However, it may be preferred to employ a target nucleic acid that is single stranded. For example, when three ND primers are used to amplify a single-stranded nucleic acid, they are preferably designed such that two ND primers are complementary to the single stranded nucleic acid, while the third ND primer is complementary to the products of their extension. Examples of ND primer designs to provide ACA are shown in FIG. 5 herein. The number of forward versus reverse ND primers used in ACA may vary. In a preferred embodiment, the number of forward and reverse ND primers used in ACA is equal. In yet another preferred embodiment, the number of forward and reverse ND primers differs by 1. ND primers may be applied in reaction consecutively where, for example, exterior ND primers are used first, followed by addition of interior ND primers. In PCR, this approach is known as nested PCR. As generally recognized and accepted in the art, simultaneous use of more than two PCR primers in amplifying the same target nucleic acid affords no advantage, and consequently the process is performed as two consecutive separate reactions. Therefore, in this aspect, ACA is fundamentally different from PCR, nested PCR and other amplification techniques.

In preferred embodiments, all ND primers of ACA are applied simultaneously. ND primers in ACA may overlap in their binding sites or share a certain degree of homology. In preferred aspects, ND primers do not overlap. ACA can be used to amplify DNA fragments essentially of any length or almost as long the target nucleic acid itself. However, the length of the amplicons may affect the amplification rate. Therefore, when ACA is used for nucleic acid detection, ND primers are preferably designed to have their binding sites in close proximity to each other, resulting in amplicons that are ~50-500 nucleotide in length.

ND primers of the invention can be prepared by any approach known in the art. In preferred aspects, ND primers are produced using methods organic and nucleic acids chemistry. ND primers of the invention may be also prepared by nuclease digestion of a polymer nucleic acid prior or during ACA amplification. For example, Endonuclease V can cleave single- and double-stranded nucleic acids incorporating inosine (dI) and deoxyuridine (dU) modifications. A single- or double-stranded polynucleotide may be prepared to incorporate dI or dU modifications, e.g. using PCR in presence of dUTP or dITP. Exposure of this polymer in a media containing Endo V activity leads to digestion at the modification sites, providing ND primers. Use of this approach to prepare ND primers requires a substantial degree of homology between the polymer used to prepare ND primers and the nucleic acids to be amplified. ND primers are usually selected to have 3' sequences that are substantially complementary to a target nucleic acid sequence. ND primers are designed in length and nucleotide composition to have sufficient hybridization properties to form complementary complexes with respective template strands to enable primer elongations to occur. When dI and dU are used in the design of the ND primers, the nick-directing modifications are preferably introduced into the ND primers such that deoxyinosine and deoxyuridine form respective Watson-Crick base pairs with cytosine and adenosine in the target nucleic acid strand. However, ND primer sequences do not necessary need to reflect the exact sequence of the target template. For example, a non-complementary nucleotide fragment may be attached to the 5' end of the primer, with the remainder of the primer sequence being substantially complementary to the target nucleic acid. ND primers can be designed such that this 5' nucleotide fragment is incorporated into the ACA products in a duplex form. The 5'-nucleotide fragment may comprise a specialty sequence. For example, this specialty sequence may prompt the respective amplicons to fold into a secondary structure wherein this structure can be used for the amplicon detection as described in Kutyavin I. V. (2007a). The specialty sequence may also incorporate one or more restriction sites to make the amplicons suitable for use in molecular biology and genetic engineering. Non-complementary bases or longer sequences can be interspersed into the primer, provided that the primer sequence has sufficient complementarity with the sequence of the target/template to hybridize and thereby form a template-primer complex for synthesis of the extension product. In one aspect, the ND modification is located within a primer sequence that is substantially complementary to the target nucleic acid. In another aspect, ND is located within a primer sequence, e.g. a 5'-tail sequence, that is not complementary to the target nucleic acid.

In particular embodiments of the invention, at least one of the ND primers incorporates more than one ND modification. In another embodiment, ND primers incorporate different ND modifications and the reaction mixture comprises nick-directing endonucleases providing cleavage of nucleic acids incorporating said different nick directing modifications. Nick-directing modifications may be of a nucleotide nature, for example, a nucleotide sequence which represents a binding and cleavage site of a restriction enzyme that cleaves only one strand of duplex nucleic acids. These strand specific nucleases are also known as "nicking endonucleases" and examples thereof include but are not limited to Nb.BbvCI, Nb.BsmI, Nb.BsrDI, Nb.BtsI, Nt.AlwI, Nt.BbvCI, Nt.BspQI, Nt.BstNBI and Nt.CviPII, which can be obtained from, e.g. New England Biolabs. Nick-directing modifications useful for methods of the invention may be RNA nucleotides, or RNA fragments incorporated into composite RNA/DNA primers (see, e.g., Cleuziat P. and Mandrand B., 1998; Kurn N., 2001; Kurn N., 2004; Kurn N., 2005; and Sagawa H. et al, 2003), wherein RNase H serves as a ND nuclease to provide the strand-specific cleavage of the double-stranded extension products obtained with these composite RNA/DNA primers. In this aspect, ND primers of the invention may comprise only RNA nucleotides. ND modifications of the invention may be located anywhere within the ND primer sequence and the optimal location is usually defined by particular type(s) of the ND modification used. For example, RNA segments in the composite RNA/DNA nick-directing primers may be located at the 5'-end (e.g., Cleuziat P. and Mandrand B., 1998; Kurn N., 2001; Kurn N., 2004; Kurn N., 2005), in the middle, or at the 3'-end of the primer sequences (e.g., Sagawa H. et al, 2003). When nick-directing modifications are modified nucleotides such as deoxyinosine and/or deoxyuridine, and the ND nuclease used is Endonuclease V, these ND modifications are preferentially located at or near the 3'-end.

Nick-directing modifications of the invention may also be any residues or moieties that are not of a nucleotide nature. Other examples of nick-directing modification include but are not limited to those that are described, for instance, in publications of Saba J. (2004) and Millar D. S. et al (2006), which are incorporated herein by reference. In preferred embodiments of the invention, nick-directing modifications are modified nucleotides. In yet other preferred embodiments, these modified nucleotides are deoxyinosine (dI) and deoxyuridine (dU), which are used in the design of ND primers of the invention to direct strand-specific cleavage of duplex nucleic acids by Endonuclease V.

In one embodiment of the invention, the nick-directing primers contain structural modifications other than nick-directing modifications. These structural modifications can be of nucleotide and non-nucleotide nature, hydrophobic and hydrophilic, as big as natural polypeptides and as small as single atom. Examples of these structural modifications include but are not limited to chemical substances such as atoms, moieties, residues, polymers, linkers, tails, markers or nucleotide analogs, which are usually of a synthetic nature and which are not commonly present in natural nucleic acids, e.g. nucleoside or nucleotide analogs such as 5-bromouracil, 5-methylcytosine, 5-iodouracil, 2-aminoadenosine, 6-methyladenosine, preudouridine and the like. ND primers can also incorporate detectable labels. In this aspect ND primers can perform two functions by providing amplification and detection of target nucleic acids. In a preferred embodiment, these structural modifications are duplex-stabilizing modifications. Use of such structural modifications in design of ND primers of the invention may be particularly beneficial because it allows for preparing primers with elevated hybridization properties. n one embodiment, the duplex-stabilizing modifications are modified nucleotides. Examples of these modified nucleotides that are known to provide duplex stabilization include but are not limited to Locked Nucleic Acids (LNA) (Latorra D. et al, 2003a; Latorra D. et al, 2003b; Di Giusto D. A. and King G. C., 2004), Polyamide Nucleic Acids (PNA) (Egholm M. et al, 1993), ribonucleotides, 2'-O-methyl RNA and 2'-fluoro RNA, 2,6-diaminopurine and 5-methylcytosine nucleotides (Lebedev Y. et al, 1996), 5-propynolpyrimidines (Froehler B. et al, 1997), pyrazolopyrimidines or 8-aza-7-deazapurines (Petrie C. R. et al, 1998; Meyer R. B. et al, 2000; Gall A. A. et al, 2003) and different variations thereof. In another embodiment, duplex-stabilizing modifications comprise a 'tail' conjugated to the 5'-end of the nick-directing primers. Examples of such tails are minor groove binders (MGB) (Kutyavin I. V. et al, 1997; Afonina I. et al, 1997; Kutyavin I. V. et al, 1998) and intercalators (Asseline U. et al, 1984; Nguyen T. T. et al, 1989).

Unlike the primers used in PCR and other amplification technologies, ND primers of the invention are generally less restricted in the number, type and location of structural modifications used in their design. However, those of ordinary skill in the art will appreciate that certain design rules may still apply in order to maintain the ND primer capability to initiate DNA extension. For example, at least 4, and preferably more than 4 nucleotides at the 3'-end of ND primers should be natural nucleotides. Nonetheless, some modified nucleotides may be used within the 3'-end sequences, for example, 2,6-diaminopurine, 5-propynyluridine, 5-methyl cytosine, etc., including certain nick directing modifications like deoxyinosine and deoxyuridine. The duplex-stabilizing tails like intercalators and minor groove binders should preferably be conjugated to the 5'-end.

Not unlike other amplification technologies, the functional efficiency of ND primers in methods of the invention depends, at least in part, on their hybridization properties. In particular aspects, ND primers may have melting temperatures that are close to, or even below the ACA reaction temperature. Nonetheless, ND primers employed in ACA do not need to cycle in the target hybridization, and may remain bound to the DNA template indefinitely during the amplification reaction. Therefore ND primers are preferably designed to have hybridization properties or melting temperatures that are above the ACA reaction temperature. Hybridization properties of ND primers are primarily defined by their length, base composition and reaction conditions (e.g. magnesium ion concentration). Duplex-stabilizing modifications can be effectively applied in the design, providing ND primers with sufficient hybridization properties. In this aspect, hybridization properties of ND primers may be improved by amplifying target nucleic acids in the presence of base-modified duplex-stabilizing dNTPs. This technology has been described in detail (Kutyavin I. V., 2007b), which is incorporated herein by reference.

A simple estimate of the Tm value may be calculated using the equation Tm=81.5+0.41(% G+C), when a nucleic acid is in aqueous solution at 1 M NaCl. More accurate calculations can be made using the base pair thermodynamics of a "nearest-neighbors" approach (Breslauer K. J. et al, 1986; SantaLucia J. Jr., 1998). Melting temperatures of secondary structures may be determined using the approach and algorithm described in, e.g., Zuker M. and Jacobsen A. B., 1995, or Walter A. E. et al, 1994. Commercial programs, including Oligo™, Primer Design and programs available on the internet, including Primer3 and Oligo Calculator can be also used to calculate a Tm of a nucleic acid sequence useful according to the invention. Commercial programs, e.g., Visual OMP (DNA software), Beacon designer 7.00 (Premier Biosoft International), may also be helpful. However, these programs are usually made for the design of PCR primers, and specialty software may be used to incorporate all and/or different and numerous aspects of the invention. In a preferred embodiment, the nick-directing primers and/or probes of the invention are designed using specialty computer software.

In one embodiment of the invention, at least one of the ND primers is generated during the isothermal amplification by cleavage of a nick-directing primer precursor (ND precursor). In another embodiment, the ND precursor cannot serve as a primer in isothermal amplification of a target nucleic acid. In yet another embodiment, the ND primer is generated from a ND precursor by the activity of nick-directing endonuclease. The precursor or precursors may be used in methods of the invention to generate one or more ND primers by cleavage of the precursors during the isothermal amplification. The precursor may be completely complementary to the target nucleic acid or may incorporate nucleotides or nucleotide sequences that are not complementary to the target nucleic acid. In some aspects, the ND precursor is an ND primer having more than one ND modification. For example, when a ND primer contains two dI modifications, it may be cleaved by Endonuclease V during the amplification, resulting in two ND primers having a single dI modification. The cleavage may take place while the ND primer or precursor is in a single-stranded state, not hybridized to the target nucleic acid. The ND precursor may or may not serve as a primer in methods of the invention. For example, the ND precursor may be blocked from the extension by DNA polymerase by virtue of having nucleotides or sequences at the 3'-end of the ND precursor that are not complementary to the target nucleic acid. Alternatively certain structural modifications that do not support the extension by DNA polymerases, e.g., 3'-phosphate moiety, or tails like —P(O)(OH)—OCH$_2$CH$_2$CH$_2$OH, are introduced at or nearby the 3'-end of the precursor. The endonuclease that cleaves "inactive" precursors to generate "active" ND primers may be other than a ND nuclease. Examples include but are not limited to Endonuclease IV. For example, a ND precursor may contain a 3'-moiety like a phosphate or —P(O)(OH)—OCH$_2$CH$_2$CH$_2$OH tail, which can be cleaved by Endonuclease IV thereby providing an "active" ND primer.

Methods of the invention can be used to amplify more than one target nucleic acid in a single reaction mixture. In one embodiment, this can be achieved using the same set of ND primers. For example, two or more target nucleic acids may differ by one or more nucleotides including insertions and deletions while at the same time having a sufficient degree of homology through the rest of the nucleotide sequence. These nucleic acids of interest or polymorphic variations can be amplified simultaneously using the same set of ND primers when these polymorphic variations are located between the binding sites of forward and reverse ND primers. In another embodiment, two or more target nucleic acids are amplified by methods of the invention, wherein a respective set of ND primers is used for every nucleic acid of interest.

Methods of the invention can be used for many more purposes than other amplification schemes are used for. For example, ACA can be used in amplifying nucleic acids for sequencing or to prepare single- or double-stranded DNA fragments for genetic engineering. Amounts of nucleic acids of interest isolated from different sources are commonly not present in sufficient amounts to enable direct detection. Therefore the target nucleic acids need to be amplified, and this can be accomplished using ACA. In one embodiment, the isothermal amplification of the invention is performed to detect a target nucleic acid in or from a nucleic acid sample. In another embodiment, detection of a target nucleic acid is performed after the amplification. In yet another embodiment, detection of a target nucleic acid is performed in real-time. Real-time detection is a preferred format to practice ACA for nucleic acid detection. However, some detecting technologies can interfere or negatively affect the amplification process. Post-amplification detection can be applied in such cases. For example, methods of isothermal amplification disclosed herein employ DNA polymerases which lack duplex specific 5'-nuclease activity. The Presence of 5'-nucleases during the amplification should be avoided because the 5'-nucleases may interfere with the strand-displacement amplification. This may limit real-time use of detection technologies that are based on cleavage of FRET probes by 5'-nucleases, e.g. INVADER assay (Brow M. A. D. et al, 1998; Lyamichev et al, 1999).

Figure 9:
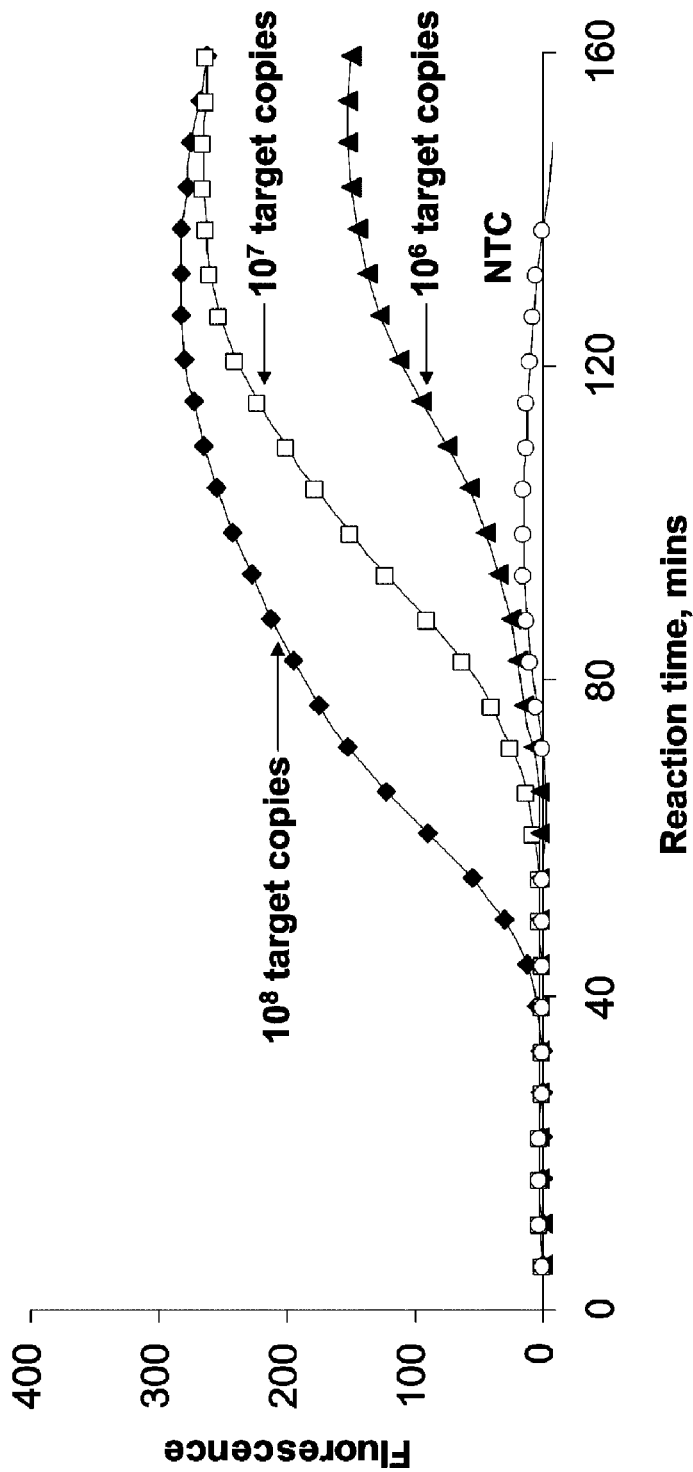
FIG. 9 shows, according to particular exemplary aspects of the present invention, fluorescence monitoring results of an exemplary reaction obtained by real-time detection of M13mp18 target DNA in the presence of eight (8) deoxyinosine incorporating primers (Primers 1-8 as described in FIG. 6), an Endo IV cleavable FRET probe, Cleavage Enhancer, Endonuclease V, Endonuclease IV, DNA polymerase and mixture of deoxynucleoside 5'-triphosphates in 50 mM KCl, 1 mM $MgCl_2$, 20 mM Tris-HCl (pH8.0). The structures of oligonucleotide components used in this experiment were those as shown in FIG. 6. The relative alignment and positioning of the primers, probe and cleavage enhancer are as shown in FIG. 8B. The reactions were incubated at 46° C. and fluorescence of Yakima Yellow reporting dye was monitored using the Cy3 channel of a SmartCycler (Cepheid). Linear fluorescence background was subtracted, and the fluorescence data points were plotted (y-axis) as a function of the reaction time (in minutes, along the x-axis). A detailed description of the experiment and results can be found herein under working EXAMPLE 3. "NTC" is an abbreviation for the "No-target Control" experiment. The amount of the target DNA was varied in the reactions as indicated for each real-time curve.

In one embodiment of the invention, detection of the target nucleic acid comprises use of a detecting agent, wherein the detecting agent interacts with amplification products providing a signal, and wherein detection of the signal is indicative of presence of the target nucleic acid in the reaction mixture. In another embodiment, the detecting agent comprises a fluorescent agent. In yet another embodiment, the fluorescent agent changes its fluorescence properties upon interaction with the amplification products to provide a signal. The preferred detecting agents of the invention are intercalating dyes and fluorescent agents. For example, amplification products can be detected using intercalating dyes like SYBR Green as described by Wittwer C. T. et al (2001) and Wittwer C. T. et al (2003). As shown herein (working Examples 1 and 2), SYBR Green dye can be used to detect amplicons of the invention including detection in real-time (see, e.g., FIG. 7). In one embodiment, detection of the target nucleic acid comprises use of an oligonucleotide probe which incorporates a label. In a preferred embodiment, the label comprises a fluorescent label. In another preferred embodiment, the oligonucleotide probe comprises a FRET probe, wherein the FRET probe changes its fluorescent properties upon forming a complementary complex with products of the isothermal amplification, and wherein the changes are indicative of the presence of the target nucleic acid. Use of the FRET assays typically allows real-time detection. Methods of the invention are preferentially based on use FRET probes because this allows target-specific detection, wherein non-target amplicons are not detected. In one embodiment, the FRET probe comprises a hybridization-triggered FRET probe. Hybridization-triggered FRET probes change their fluorescent properties upon hybridization with a target nucleic acid. This separates FRET dyes that are commonly conjugated to opposite probe ends altering FRET effects and providing a detectable signal. Examples of hybridization-triggered FRET probe technologies that may be used in methods of the invention include but are not limited to Adjacent Hybridization Probes (Cardullo R. A. et al, 1988), Self-Quenching Fluorescence probes (Livak K. J. et al, 1998), Molecular Beacons (Bonnet G. et al, 1999; Marras S. A. E. et al, 2002), PNA Molecular Beacons (Ortiz E. et al, 1998) and Eclipse (Afonina I. A. et al, 2002). In another embodiment of the invention, the FRET probe comprises a cleavable FRET probe. For example, amplicons of the invention can be detected using FRET oligonucleotide probes which are designed for cleavage by Endonuclease IV (Endo IV) as described in (Kutyavin I. V. et al, 2004, and Kutyavin I. V. et al, 2006. Endonuclease IV does not cleave internucleotide phosphodiester bonds ("general" nuclease activity), but efficiently cleaves a DNA strand in duplexes containing abasic sites. and also removes phosphates and other tails from the 3'-end of nicked duplexes. Endo IV does not interfere with ACA. The instant working Example 3 and FIG. 9 illustrate use of this technology in methods of the invention for real-time detection of target nucleic acids. These experiments also illustrate another embodiment of the invention, wherein amplification and detection of a target nucleic acid is performed to measure the amount of the target nucleic acid in or from the sample. Endo IV is stable at elevated temperatures and therefore this detection technology can be effectively used in a broad temperature range, e.g., 30-70° C.

Methods of the invention comprise use of a strand-displacing DNA polymerase that lacks 5'→3' nuclease activity. Examples include but are not limited to phi29 DNA polymerase, DNA Polymerase I Klenow Fragment, Klenow Fragment (3'→5' exo-), Vent DNA polymerase, Vent (exo-) DNA polymerase, Bst DNA polymerase Large Fragment, etc. The choice of DNA polymerase may depend on reaction conditions (e.g. reaction temperature), compatibility with ND nucleases of the invention, and many other factors. It also may depend on the nick-directing modification used in design of ND primers. For example, many strand-displacing DNA polymerases have 3'→5' nuclease activity, also known as proofreading activity, e.g. phi29 DNA polymerase and DNA Polymerase I Klenow Fragment. This proofreading activity may cleave ND primers during the amplification therefore removing certain nick directing modifications especially if these modifications are structural modifications like modified nucleotides (e.g. deoxyinosine and deoxyuridine) and they are located close to the 3'-end. In a preferred embodiment of the invention, the strand-displacing DNA polymerase has no 3'→5' nuclease activity, for example, Klenow Fragment (3'→5' exo-), Vent (exo-) DNA polymerase, Bst DNA polymerase Large Fragment, etc.

Double stranded nucleic acids containing a nick-directing modification are, for example, produced in reactions by DNA polymerase-mediated extension of a ND-primer hybridized to the target nucleic acid or an amplification product thereof. In particular methods of the invention, ND nuclease-mediated strand-specific cleavage provides for amplification of the amplifiable target sequence resulting in primer-extension products that lack the respective ND primer sequences or a portion thereof. In one embodiment of the invention, the strand-specific cleavage provided by the ND nuclease allows a "fresh" ND primer to hybridize to the target nucleic acid or amplification product thereof, providing for another cycle of DNA polymerase-mediated extension and strand displacement of the primer-extension products that lack the respective ND primer sequences or a portion thereof. In particular preferred embodiments, the strand-specific cleavage provided by the ND nuclease restores the capability of the ND primer or its portion to support DNA polymerase-mediated extension of this ND primer or the portion thereof. In particularly preferred embodiments, this "restored" ND primer or its portion has sufficient hybridization properties to remain hybridized with the target nucleic acid, or an amplification product thereof, for an extended period, or indefinitely during the amplification reaction, resulting in multiple primer-extension events and corresponding products that lack the respective ND primer sequences or a portion thereof.

Nick-directing nucleases that can be used in ACA are nucleases that cleave one strand of double-stranded nucleic acids containing nick-directing (ND) modifications at or near the modifications, such that extension of the cleaved strand by DNA polymerase does not eliminate the nick directing modification, thus supporting repetitive cycling of the cleavage and DNA extension reactions. The ND nucleases of the invention are preferably duplex-specific, but they may cleave nucleic acids incorporating nick directing modifications when these nucleic acids are in single-stranded state, for example, Endonuclease V cleaves single-stranded DNA polymers incorporating deoxyinosine and deoxyuridine modifications. ND nucleases of the invention selectively cleave nucleic acids containing ND modifications at least 10-times more efficiently than corresponding, regular nucleic acids with no ND modifications. The preferred ND nucleases of the invention are essentially free of, or express very little enzymatic activities other than the required ND nuclease activity. For example, ND nucleases preferably do not cleave single-stranded or double-stranded nucleic acids unless these nucleic acids incorporate ND modifications. The choice of a ND nuclease for practicing methods of the invention is respectively defined by a nick-directing modification used and vice versa. In some aspects, ND primers of the invention may incorporate different ND modifications. This necessitates the use of different ND nucleases in the reactions that cleave the amplicons of the invention incorporating these different ND modifications. Examples of ND nucleases useful for the invention include but are not limited to "nicking endonucleases," e.g. Nb.BbvCI, Nb.BsmI, Nb.BsrDI, Nb.BtsI, Nt.AlwI, Nt.BbvCI, Nt.BspQI, Nt.BstNBI and Nt.CviPII (New England Biolabs) that recognize specific nucleotide sequences in double-stranded DNA and cleave only one strand.

In a preferred embodiment of the invention, ND primers incorporate one or more deoxyinosine or deoxyuridine modifications, which are recognized and cleaved by Endonuclease V (Gates F. T. III and Linn S., 1977; Yao M. et al, 1994; Yao M. and Kow Y. W., 1994; Yao M., Kow Y. W., 1995; Yao M., Kow Y. W., 1996; Yao M., Kow Y. W., 1997). Endonuclease V can be isolated from a variety of organisms including archaebacteria, eubacteria and eukaryotes using techniques and approaches well established in the art. For example, Endonuclease V was identified and isolated from hyperthermophiles *Archaeoglobus fulgidus* (Liu J. et al, 2000), *Thermotoga maritima* (Huang J. et al, 2001; Huang J. et al, 2002) and mice (Moe A. et al, 2003). The thermo stable enzymes such as Endonucleases V from *Archaeoglobus fulgidus, Thermotoga maritima* are particularly useful in methods of the invention because these nucleases express activity at temperatures>50° C.

In another preferred embodiment of the invention, the nick-directing endonuclease is a nuclease with improved cleavage cycling properties providing cleavage more than one product of extension of the nick-directing primer in one minute. In yet another preferred embodiment, the nick-directing endonuclease cleaves more than five products of extension of the nick directing primer in one minute. In particular aspects, the capability of nick-directing nuclease to cleave multiple products of extension of the nick directing primers in a cycling mode enhances the efficiency (amplification speed), target specificity and other parameters of ACA. It may be anticipated, in particular, that the amplification rate in ACA depends on the processivity of ND nucleases (cycling capabilities). The greater the number of nucleic acid duplexes cleaved by a nick-directing nuclease, the faster ACA amplification proceeds. However, many known nick-directing endonucleases have limited cycling capabilities. For example, Endonucleases V isolated from natural sources commonly displays elevated affinity to dI-containing duplex substrates including the cleaved substrate (Huang J. et al, 2001; Huang J. et al, 2002; Yao M. et al, 1994; Yao M. and Kow Y. W., 1994; Yao M., Kow Y. W., 1995; Yao M., Kow Y. W., 1996; Yao M., Kow Y. W., 1997). This tight-binding of the endonuclease to the cleaved duplex substrate reduces the Endonuclease V processivity or capability for cycling, i.e. when one molecule of the enzyme can cleave multiple duplex substrates. Nick-directing nucleases with improved and elevated cycling capabilities can be prepared by methods of molecular biology and genetic engineering established in the art. An example of this is provided by Huang J. et al, 2002 which is incorporated herein by reference. The authors prepared, isolated and studied a number of mutants of Endonuclease V from *Thermotoga maritima*. Several mutants, in particular, Y80A, H116A, R88A and K139A, were found to have improved cleavage cycling properties in reaction with excess of double-stranded substrate incorporating deoxyinosine modification (E:S=1:10). Therefore, in preferred embodiments of the invention, the Endonuclease V is at least one mutant or variant Endonuclease V from *Thermotoga maritima* selected from a group consisting of Y80A, H116A, R88A and K139A mutants. Additional mutants encompassed by the present invention are described in U.S. Pat. No. 7,198,894, which is incorporated herein by reference.

Amplification and detection reactions of the invention can be performed in different reaction vessels and the reaction mixtures comprise a solution containing all the necessary reactants for performing the amplification and/or detection of target nucleic acids, which in addition to primary components, such as target nucleic acids, DNA polymerases, ND nucleases, ND primers, probes, nucleoside 5'-triphosphates or other necessary components, may include at least one additional agent selected from, but not limited to detecting agents, specialty enzymes, modified dNTPs, buffering agents to maintain pH at a selected level, salts, co-factors and additives, for example, 1-methyl-2-pyrrolidinone, glycerol, poly (ethylene glycol), dimethyl sulfoxide or formamide and the like. Many strand-displacing DNA polymerases and ND nucleases require the presence of magnesium or other metal ions for expressing the enzymatic activity, and the reaction mixtures may incorporate these components. The amplification temperature in methods of the invention depends on many factors, including the purpose of the method, stability and activity of the enzymes used, hybridization properties of primers, probes and other oligonucleotide components, etc., and the amplification temperature can be from about 10 to about 85° C. In one embodiment, isothermal amplification is performed at temperatures between about 15 and about 50° C. In another embodiment, the isothermal amplification is performed at temperatures between about 50 and about 80° C. WGA applications may require relatively low temperatures (~15-30° C.) whereas elevated temperatures (>50° C.) may be preferred for methods of nucleic acid detection. Thermal stability and optimal temperature activity of the enzymes used is yet another factor effecting the choice of the reaction temperature. For example, as shown herein in the working Examples of the invention, combination of Endonuclease V from *E. coli* and Klenow Fragment (exo-) do not allow performing the amplification at temperatures>48° C., likely due to instability of one of the enzymes. Thermostable enzymes, e.g., Endonuclease V from *Thermotoga maritima* and *Archaeoglobus fulgidus* and DNA polymerases Vent (exo-), Bst DNA polymerase Large Fragment are needed to perform the methods of the invention at elevated temperatures.

Methods of the invention may be performed in both homogeneous (when all reaction components are in a solution) and heterogeneous forms (when at least one of the components is immobilized). In one embodiment, at least one ND primer is immobilized on solid support. There are numerous aspects of performing methods of the invention in heterogeneous formats wherein, for example, one of the primers, preferably internal, is not an ND primer and may comprise, for example, a structural modification or tag that serves to immobilize this primer on a solid support after or during the amplification for further stages of, e.g., detection or sequencing of the target nucleic acid.

Aspects of the invention also include a kit to perform the methods of the invention, wherein the kit comprises at least three nick-directing primers designed to provide accelerated cascade amplification (ACA). In yet another embodiment, the kit further comprises at least one of a strand-displacing DNA polymerase, and a nick-directing endonuclease.

The oligonucleotide components of the invention such as ND primers, cleavage enhancers and probes may be synthesized using techniques that are well known in the Art. Although the ND primers can be prepared by, for example, cloning and restriction digestion of appropriate sequences, direct chemical synthesis is a preferred approach. Oligonucleotide components can be prepared by a suitable chemical synthesis method, including, for example, the phosphodiester method disclosed in Brown E. L. et al (1979), the phosphotriester method described in Narang S. A. et al (1979). The preferred approach is the diethylphosphoramidate method disclosed in Beaucage S. L., Caruthers M. H. (1981), in combination with the solid support method disclosed in Caruthers M. H., Matteucci M. D. (1984) and performed using one of commercial automated oligonucleotide synthesizer. When oligonucleotide components of the invention need to be labeled with a fluorescent dye, a wide range of fluorophores may be applied in probe and primer designs and synthesis. Available fluorophores include but not limited to coumarin, fluorescein (FAM, usually 6-fluorescein or 6-FAM), tetrachlorofluorescein (TET), hexachloro fluorescein (HEX), rhodamine, tetramethylrhodamine, BODIPY, Cy3, Cy5, Cy7, Texas red and ROX. Fluorophores may be chosen to absorb and emit in the visible spectrum or outside the visible spectrum, such as in the ultraviolet or infrared ranges. FRET probes of the invention commonly incorporate a pair of fluorophores, one of which may be a none-fluorescent chromophore (commonly referred as a "dark quencher"). Suitable dark quenchers described in the art include Dabcyl and its derivatives like Methyl Red. Commercial non-fluorescent quenchers, e.g., Eclipse (Glen Research) and BHQ1, BHQ2, BHQ3 (Biosearch Technologies), may be also used for synthesis of FRET probes of the invention. Preferred quenchers are either dark quenchers or fluorophores that do not fluoresce in the chosen detection range of an assay. The donor and acceptor fluorophores for manufacturing of the labeled oligonucleotide components of the invention may be selected from suitable fluorescent groups, e.g. 6-FAM (6-carboxyfluorescein); 6-hexachloro-fluorescein ([4,7,2',4',5',7'-hexachloro-(3',6'-dipivaloylfluoresceinyl)-5-carboxylic acid]); 6-tetrachloro-fluorescein ([4,7,2', 7'-tetrachloro-(3',6'-dipivaloylfluoresceinyl)-6-carboxylic acid]); 6-TAMRA (6-carboxytetramethylrhodamine; Dabcyl (4-((4-(dimethylamino)phenyl) azo)benzoic acid); Cy5 (Indodicarbocyanine-5); Cy3 (Indo-dicarbocyanine-3); and the like. Modified nucleoside or nucleotide analogs including nick-directing modifications like deoxyinosine (hypoxanthine) and deoxyuridine, which are rarely present in natural nucleic acids may be incorporated synthetically into oligonucleotide components, for example, 5-bromouracil, 5-methylcytosine, 5-iodouracil, 2-aminoadenosine (2,6-diaminopurine), 6-methyladenosine, preudouridine and the like. The same applies to linkers, spacers, specialty tails like intercalators and minor groove binders. All these chemical components can be prepared according to methods of organic chemistry or using respective protocols that can be found in manuscripts and patents cited herein. Many structural modifications and modified nucleosides useful to prepare oligonucleotide components of the invention are available, commonly in convenient forms of phosphoramidites and specialty CPG, from commercial sources, e.g., Glen Research, Biosearch Technologies, etc.

Detailed Exemplary Embodiments

The amounts of nucleic acids of interest present in or isolated from different sources are often insufficient for basic research, biotechnological production and other scientific and industrial purposes including direct detection. Therefore the target nucleic acids typically need to be amplified. The following Materials and Methods, and working Examples are provided and disclosed to demonstrate certain aspects and methods of the invention for amplification and detection of target nucleic acids. The examples are provided solely for illustrative purposes, and are not intended to limit the scope of the inventive methods and applications.

Materials and Methods

Figure 6:
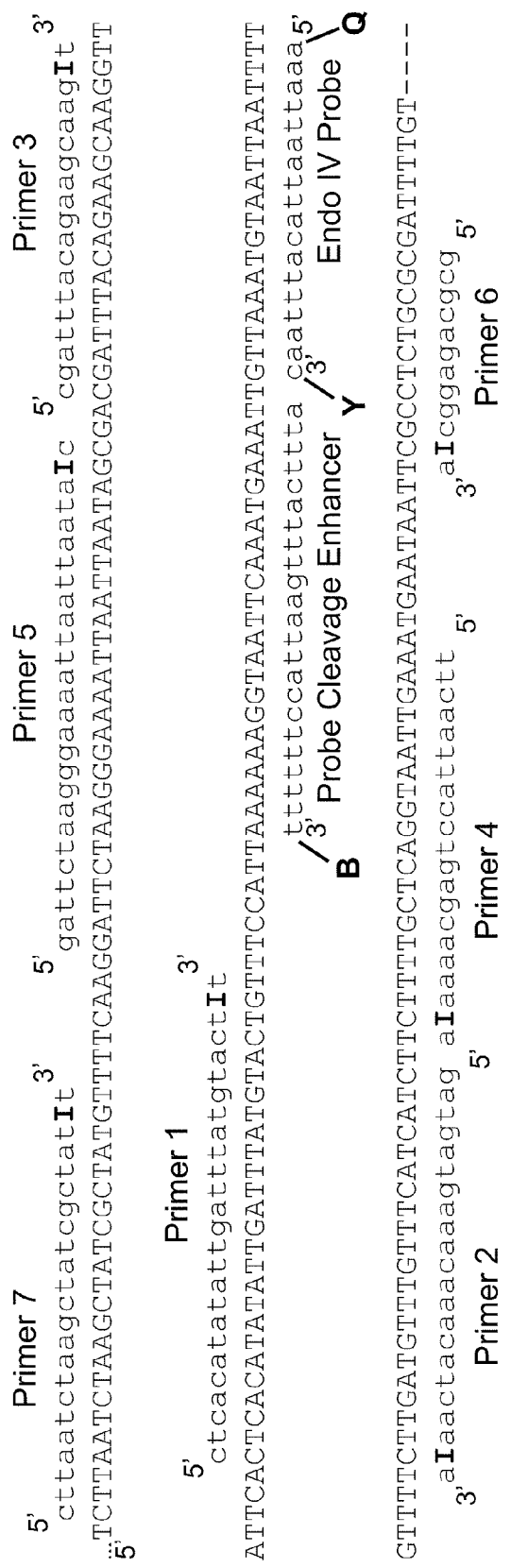
FIG. 6 shows, according to particular exemplary aspects of the present invention, an M13mp18 target fragment (SEQ ID NO:8) (GenBank accession #M77815, between nucleotides T4086-G4349) and oligonucleotide components used in Examples of the present invention. "B" is a —P(O)OH—OCH$_2$CH$_2$CH$_2$OH moiety conjugated to the 3'-OH group of a "Cleavage Enhancer" oligonucleotide (SEQ ID NO:9) in order to block its elongation by DNA polymerase. The "Endo IV" cleavable FRET oligonucleotide probe (SEQ ID NO:10) incorporated a 5' quencher dye "Q" (BHQ2 from Biosearch Technologies), and fluorescence-reporting dye "Y" (Yakima Yellow from Glen Research). "I" is the abbreviation for the deoxyinosine nucleotide used in the design of nick-directing primers 1-8, corresponding to SEQ ID NOS:11-18, respectively. Primers, probe and cleavage enhancer are aligned with the M13mp18 sequence (SEQ ID NO:8) to show their binding position in 5'-3' orientation as indicated.

Synthesis of oligonucleotide components. Structures and sequences of exemplary nick-directing primers, Endo IV cleavable FRET probe and Cleavage Enhancer are shown in FIG. 6. A Yakima Yellow reporting dye was incorporated onto the 3'-end of the probe using Epoch Yakima Yellow™ CPG from Glen Research. BHQ2 "dark" quencher was introduced using BHQ-2 DMT Amidite from Biosearch Technologies. A propanediol tail was introduced onto the 3'-end of the Cleavage Enhancer using 3'-Spacer C3 CPG from Glen Research. Deoxyinosine containing primers were prepared using dI-CE Phosphoramidite from Glen Research. Standard phosphoramidites, solid supports and reagents to perform the solid support oligonucleotide synthesis were also purchased from Glen Research. 5-Ethylthio-1H-tetrazile solution (0.25 M) was used as a coupling agent. Oligonucleotides were synthesized either on ABI394 DNA synthesizer (Applied Biosystems) or MerMaid 6 DNA synthesizer (BioAutomation Corporation) using protocols recommended by the manufacturers for 0.2 or 1 mmole synthesis scales. After the automated synthesis, oligonucleotides were deprotected in aqueous 30% ammonia solution by incubation for 2 days at room temperature, 12 hours at 55° C. or 2 hours at 70° C.

Purification of oligonucleotide components. Tri-ON oligonucleotides were purified by HPLC on a reverse phase C18 column (LUNA 5 µg/m, 100 A, 250×4.6 mm, Phenomenex Inc) using gradient of acetonitryl in 0.1 M triethyl ammonium acetate (pH 8.0) or carbonate (pH 8.5) buffer with flow rate of 1 ml/min. A gradient profile including washing stage 0→14% (10"), 14→45% (23'), 45→90% (10"), 90→90% (5'50"), 90→0% (30"), 0→0% (7'30") was be applied for purification of all Tri-ON oligonucleotides. The product containing fractions were dried down in vacuum (SPD 1010 SpeedVac system, TermoSavant) and trityl groups were removed by treatment in 80% aqueous acetic acid at room temperature for 40-60 minutes. After addition to the detritylation reaction (100 μl) of 20 μl sodium acetate (3 M), the oligonucleotide components were precipitated in alcohol (1.5 ml), centrifuged, washed with alcohol and dried down. Concentration of the oligonucleotide components was determined based on the optical density at 260 nm and the extinction coefficients calculated for individual oligonucleotides using on-line Oligo-Analyzer 3.0 software provided by Integrated DNA Technologies. Based on the measurements, convenient stock solutions in water were prepared and stored at −20° C. for further use.

Oligonucleotide quality control. The purity of all prepared oligonucleotide components was confirmed by analytical 8-20% PAAG electrophoresis, reverse phase HPLC and by spectroscopy on Cary 4000 UV-VIS spectrophotometer equipped with Cary WinUV software, Bio Package 3.0 (Varian, Inc.).

Example 1

An Exemplary M13mp18 Target Nucleic Acid was Amplified by the Inventive Accelerated Cascade Amplification (ACA) Method In this Example, an exemplary M13mp18 target nucleic acid was amplified by the inventive Accelerated Cascade Amplification (ACA) method.

Reaction mixtures of 25 μl total volume were prepared on ice to incorporate the following components with indicated providers, amounts and concentrations: M13mp18 single-stranded DNA (New England BioLabs Inc.) at $10^8$ copies per reaction; deoxyinosine incorporating primers (variable number, with structures shown in FIG. 6) at 100 nM for each individual primer; SYBR Green (Invitrogen) at 0.2 U/μl; dATP, dTTP, dCTP and dGTP (Sigma) at 200 μM for each nucleoside 5'-triphosphate; Endonuclease V (New England BioLabs Inc.) at 0.04 U/μl; Klenow fragment (3'→5' exo-) (DNA polymerase with no nuclease activity from New England BioLabs Inc.) at 0.4 U/μl in 50 mM KCl, 1 mM $MgCl_2$, 20 mM Tris-HCl (pH8.0). The reactions were incubated at 46° C., and fluorescence was monitored using Smart-Cycler™ (Cepheid). Initial fluorescence was subtracted.

Figure 7:
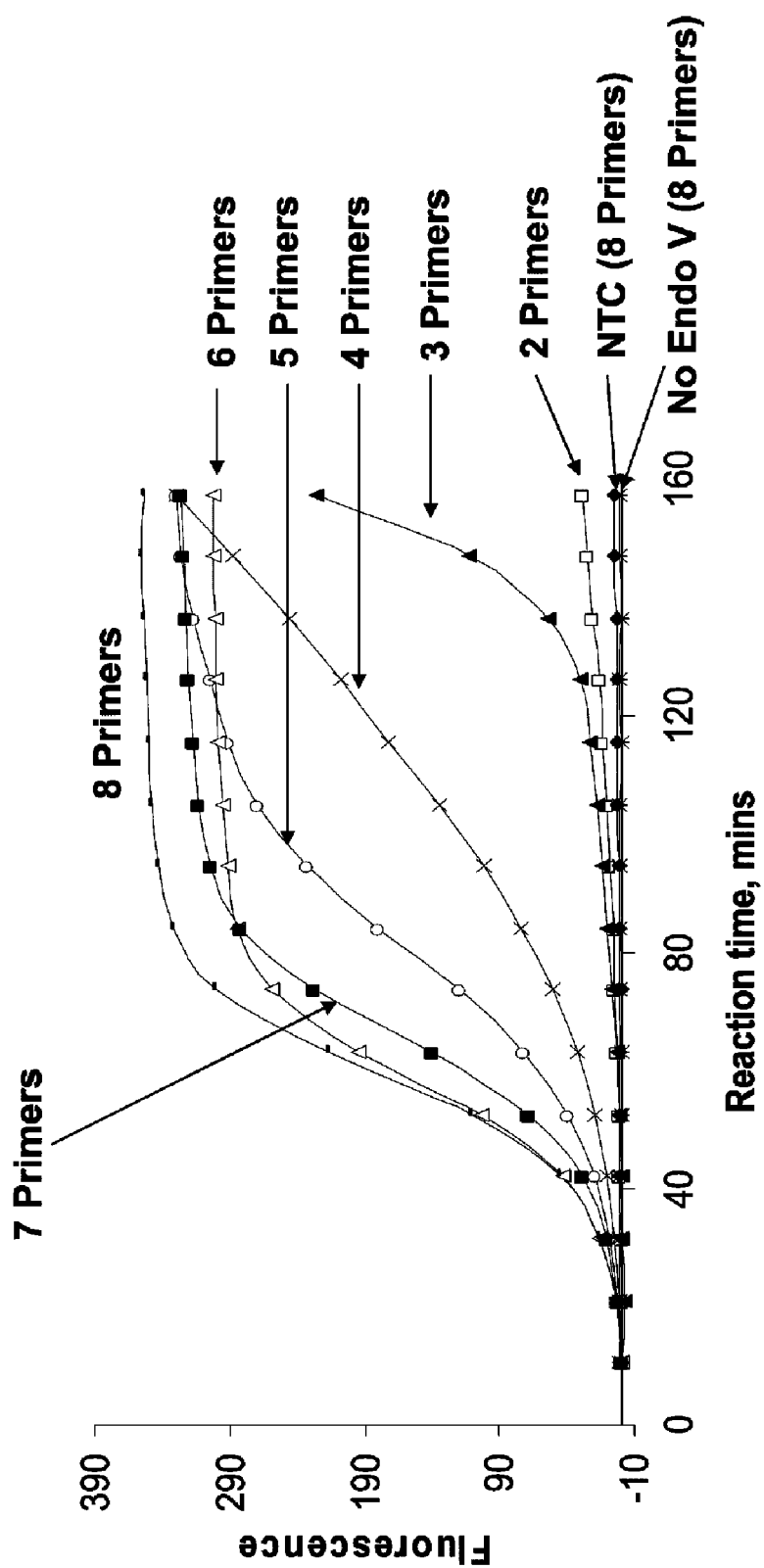
FIG. 7 shows, according to particular exemplary aspects of the present invention, results of fluorescence monitoring of Accelerated Cascade Amplification (ACA) of M13mp18 target nucleic acid with variable numbers of nick-directing primers used in the reaction. The reaction mixtures comprised target DNA ($10^8$ copies per reaction), ND primers (variable), nick displacing DNA polymerase, Endonuclease V, SYBR Green and deoxynucleoside 5'-triphosphates in 50 mM KCl, 1 mM MgCl$_2$, 20 mM Tris-HCl (pH8.0). Sequences of the ND primers are those shown in FIG. 6. The individual numbers of the ND primers corresponds to the order in which they were introduced into the reactions having multiple primers. For example: the reaction labeled "2 Primers" comprises primers 1 and 2; the reaction labeled "3 Primers" comprises primers 1, 2 and 3, whereas the reaction labeled "4 Primers" comprises primers 1, 2, 3 and 4, etc. The reaction mixtures were incubated at 46° C., and amplification products were detected in real-time (shown in minutes on the x-axis) by increasing fluorescence of SYBR® Green I (from Invitrogen™) (shown on y-axis). "NTC" is an abbreviation for the "No-Template Control" reaction, wherein no target DNA was added to the mixture of 8 Primers. The "No Endo V" experiment represents a reaction, wherein Endonuclease V was omitted. A detailed description of the experimental reactions and results is provided herein under working EXAMPLE 1.

Results are shown in FIG. 7. Each real-time curve represents an average of 3-4 individual reactions of the same composition using the number of the primers as indicated. The individual number designations (e.g., Primer 1, Primer 2, Primer 3, etc.) of the nick-directing primers (ND primers) shown in FIG. 6 additionally corresponds to the order in which they were introduced into the reactions of FIG. 7 that comprised multiple primers. For example, the "2 Primers" reaction of FIG. 7 comprises primers 1 and 2; the "3 Primers" reaction of FIG. 7 comprises primers 1, 2 and 3, whereas the "4 Primers" reaction of FIG. 7 comprises primers 1, 2, 3 and 4, and so forth. In order to avoid absorption of target nucleic acid to the plastic tubes at subnanomolar concentration, M13mp18 DNA was diluted to desired concentrations in 100 nM octadeca deoxyadenilate ($dA_{18}$) which was conjugated by its 3'-end to a 1,3-propandiol phosphate moiety and these stock solutions were stored frozen and used to prepare the exemplary reactions of the invention.

The "2 Primers" reaction of FIG. 7 represents an example of Nick Directing Amplification (NDA) as disclosed in, e.g., Saba J. (2004) and Millar D. S. et al (2006). No appreciable change in fluorescence was observed after incubation of this reaction mixture for 2.5 hours. The reaction is too slow and inefficient to amplify the M13mp18 target fragment to a level detectable by a SYBR Green fluorescent dye. Surprisingly, addition to the same reaction mixture of third nick directing primer (the "3 Primers" reaction of FIG. 7) significantly accelerated the target amplification, resulting in a real-time fluorescent curve. The "3 Primers" reaction of FIG. 7 represents an example of the present Accelerated Cascade Amplification (ACA) invention, wherein three nick-directing primers are designed and used to provide ACA of a target nucleic acid of interest. As can be seen in FIG. 7, the speed and efficiency of ACA increased substantial with increasing the number of ND primers applied in reactions reaching a saturation level at a number of ND primers of about 6 or greater. The ACA amplification was target specific and no fluorescence change was detected in the "no target control" (NTC) reactions with all of the studied primer combinations. Importantly, no target amplification, as indicated by no change in reaction fluorescence, was observed when Endonuclease V was omitted in the studied reaction (e.g. see the "No Endo V, (8 Primers)" reaction in FIG. 7).

The substantial enhancement of target amplification seen in ACA with increasing numbers of ND primers used in the reaction was unexpected, (see below for discussion). As appreciated in the art, extension of any external forward primer, such as an ND primer added to a reaction mixture should eventually displace any internal primer, such as a forward ND primer hybridized to the same target strand downstream. Moreover, the extension product of the external primer, by virtue of forming a duplex with the target, would be expected to prevent any internal primer from hybridizing to the same template strand (in duplex form) thereby effectively eliminating the internal ND primers from the amplification process. The same scenario would be expected to apply with respect to elongation of the external reverse ND primer with an expected exclusion of internal reverse ND primers. In these aspect, therefore, it would be further expected that the overall amplification process would be effectively defined by the two, most external primers, one of which is forward and another is reverse; that is, corresponding to the case of Nick Displacing Amplification NDA (Saba J., 2004; Millar D. S. et al, 2006), which consists of the use of only two ND primers (i.e., corresponding to the two external ND primers in ACA). Moreover, there would have been no expectation of an accelerated amplification, as seen herein for ACA, based on the knowledge in the art relating to implementations of nested PCR, which is not an isothermal amplification method, but rather involves strand denaturation between amplification cycles, such that even if the external and internal primers were used in the same reaction (which in fact is not the case in nested PCR), the primer pairs would not compete in template hybridization processes, and wherein, as recognized in the art, there is no advantage in the simultaneous use of both external and internal primer pairs in the same reaction, because the internal primers produce shorter, higher yield amplicons, and effectively dominate the PCR yield, particular at higher cycle numbers.

Surprisingly, however, the observed results (FIG. 7) indicate that ND primers in ACA not only do not interfere with each other, but provide for an unexpectedly enhanced amplification, representing amplification products of sizes corresponding not only to the external primer pairs, but also to all internal primer pairs (see Example 2 below and FIG. 8 discussed therein), which Applicant refers to herein as Accelerated Cascade Amplification (ACA). Moreover, this representation of all fragment sizes, coupled with the extent of the reaction acceleration produced by the use of additional ND primers suggested to Applicant (as discussed below) a mechanism of ACA action involving sequential, cascading ND primer-mediated amplification reactions.

Example 2

Analysis of Products of Accelerated Cascade Amplification (ACA) of an Exemplary M13mp18 Target Nucleic Acid by Electrophoresis in 10% PAAG Showed Unanticipated Results, and Suggested a 'Cascade' Mechanism for ACA In this Example, analysis of products of Accelerated Cascade Amplification (ACA) of an exemplary M13mp18 target nucleic acid by electrophoresis in 10% PAAG showed unanticipated results, and suggested a 'cascade' mechanism for ACA.

Reaction mixtures of 200 µl total volume were prepared on ice, and comprised the following components with the indicated amounts and concentrations: M13mp18 single-stranded DNA at $10^8$ copies per reaction; eight (8) deoxyinosine incorporating primers (Primer Nos. 1-8, as shown in FIG. 6) at 100 nM for each individual primer; dATP, dTTP, dCTP and dGTP at 200 µM for each nucleoside 5'-triphosphate; Endonuclease V at 0.04 U/µl; Klenow fragment (3'→5' exo-) at 0.4 U/µl in 50 mM KCl, 1 mM $MgCl_2$, 20 mM Tris-HCl (pH8.0). The reactions were incubated at 46° C. and samples (25 µl) were taken after 21, 42, 53, 74, 84, 95, 116 and 137 minutes of incubation. The amplification was stopped by addition of 1.25 µl of 40 mM EDTA. Before loading the samples into a 10% precast polyacrylamide gel (EMBI Tec), a 2 µl volume of each sample was mixed with 5 µl of water and 1.5 µl of 6× loading solution containing SYBR® Green I and the mixtures were loaded into the gel wells. After electrophoresis, DNA in the gel was visualized by fluorescence of SYBR Green. The fluorescent image of the gel is shown in FIG. 8A.

Specifically, FIG. 8A shows, according to particular exemplary aspects of the present invention, results of a 10% polyacrylamide gel (PAAG) electrophoretic analysis of products of the Accelerated Cascade Amplification of M13mp18. Like the "8 primers" reaction of FIG. 7, the reaction mixtures comprised M13mp18 target DNA (108 copies per reaction), and the eight (8) ND primers (FIG. 6 Primers 1-8). The "M" lanes correspond to sample wells loaded with DNA duplex markers of 100, 200, 300 and incrementally longer base pairs (bp). DNA in the gel was visualized by monitoring fluorescence of SYBR Green added to the samples prior the electrophoresis. SYBR Green predominantly binds and therefore detects double-stranded products. A series of discrete double-stranded reaction products are visible in the lanes, and increase in intensity with reaction time. Based on the molecular weight markers, the primary reaction products are between about 50 and about 250 bp.

As shown in FIG. 8A, the results of electrophoretic analysis of ACA amplification indicated the appearance of multiple DNA fragments within a length range of ~50-250 base pairs. As the reaction progressed, the amount of amplified material increased, in good agreement with the real-time results of the "8 Primers" reaction shown in FIG. 7, which shows accelerated fluorescence accumulation detectably visible by about 40 minutes and thereafter. As discussed above under working Example 1, neither the substantial enhancement of target amplification seen in ACA with increasing numbers of ND primers, nor the accumulation of amplification products of sizes corresponding to both external primers and all internal primer pairs (see FIG. 8B) was expected in the reaction.

FIG. 8B shows (upper portion of FIG. 8B) a schematic representation of a portion of a target M13mp18 nucleic acid along with alignment of four (4) forward, four (4) reverse ND primers, Endo IV cleavable FRET probe and the Probe Cleavage Enhancer. Oligonucleotide lengths, relative position of oligonucleotides vs. target nucleic acid and each other are shown to scale with the 5'-3' orientation as indicated. The sequence and alignment of the primers, Endo IV probe and the Probe Cleavage Enhancer are as shown in FIG. 6 herein (although relative to FIG. 6, the forward and reverse directions have been reversed for illustrative convenience). As can be seen, the observed amplicon length range of the amplification products shown in the gel analysis of FIG. 8A is consistent with the range limits defined by (i) the distance between the external Primers 1 and Primer 8 (see FIG. 6), and (ii) the distance between the internal Primer 4 and Primer 5 binding sites (see FIG. 6); that is, 215 and 54 nucleotides, respectively. Theoretical double-stranded Accelerated Cascade Amplification (ACA) products are depicted below the target nucleic acid schematic. The numbers shown to the right of the respective theoretical reaction products indicate the respective amplicon lengths (in base pairs (bp)) calculated for the longest strand of each double-stranded product, with ND primers incorporated. As can be seen, the theoretical amplicon lengths (i.e., 86, 109, 130, 160, 194, 213 and 238) correlate very well with the actual polyacrylamide agarose gel (PAAG) electrophoretic profiles of FIG. 8A, showing respective bands of these size classes. Additionally, the shortest ACA amplification products (~50-100 bp) appeared at later reaction times, and tended to accumulate, somewhat disproportionately, at late stages of the reaction (e.g. at reaction times greater than about 74, 84 or 95 minutes).

Without being bound by any particular theory, and according to particular aspects of Applicant's conception, the double-stranded ACA products visible in the gel analysis of FIG. 8A, represent the ACA products predicted by Applicant if: (i) ACA amplification is effectively initiated by the most external reverse ND primer; and (ii) the internal ND primers, effectively enter into the ACA amplification process in a sequential cascade (e.g. one after another); that is, beginning with the most external of the internal ND primers, followed by the next most external of the internal ND primers, and so forth, in an sequential, cascading process which Applicant refers to herein as Accelerated Cascade Amplification (ACA). This mechanism is discussed in further detail herein below.

Applicant notes that the SYBR® Green I dye used in these experiments predominantly binds, and therefore predominantly allows for detection of double-stranded products. While single-stranded amplicons may be present in the reaction mixtures, they are less efficiently detected by SYBR® Green. The electrophoretic gel image shown in FIG. 8A, therefore, likely does not represent the entire distribution and relative ratios of all nucleic acid products of the ACA amplification, but rather reflects the ratios and relative distribution of the predominant double-stranded ACA products.

Example 3

Real Time Detection of Accelerated Cascade Amplification (ACA) of an Exemplary M13mp18 Target at Different Target Nucleic Acid Concentrations was Accomplished Using an Endo IV Cleavable FRET Probe)

In this Example, real time detection of Accelerated Cascade Amplification (ACA) of an exemplary M13mp18 target at different target nucleic acid concentrations was accomplished using an Endo IV cleavable FRET probe.

Reaction mixtures of 25 µl total volume were prepared on ice, and comprised the following components at the indicated amounts and concentrations: M13mp18 single-stranded DNA at variable, $10^6$, $10^7$ and $10^8$ copies per reaction including "no template control" ("NTC"); eight (8) deoxyinosine incorporating primers (Primer nos. 1-8; having the structures shown in FIG. 6) at 100 nM for each individual primer; Endo IV cleavable FRET probe and Cleavage Enhancer (see FIG. 6) at 200 nM; dATP, dTTP, dCTP and dGTP at 200 µM for each nucleoside 5'-triphosphate; Endonuclease V at 0.04 U/µl; Endonuclease IV (Trevigen, Inc.) at 0.05 U/µl; Klenow fragment (3'→5' exo-) at 0.4 U/µl in 50 mM KCl, 1 mM $MgCl_2$, 20 mM Tris-HCl (pH8.0). The reactions were incubated at 46° C. and fluorescence of Yakima Yellow (Glen Research) was monitored in Cy3 channel of SmartCycler™ (Cepheid). Linear fluorescence background was subtracted, and the fluorescence data points were plotted as a function of the reaction time. The resulting real-time curves are shown in FIG. 9.

Specifically, FIG. 9 shows, according to particular exemplary aspects of the present invention, fluorescence monitoring results of an exemplary reaction obtained by real-time detection of M13 mp18 target DNA in the presence of eight (8) deoxyinosine incorporating primers (Primers 1-8 as described in FIG. 6). The relative alignment and positioning of the primers, Endo IV cleavable probe and cleavage enhancer are as shown in FIG. 8B. The amount of the target DNA was varied in the reactions as indicated for each real-time curve.

When an Endo IV cleavable probe and cleavage enhancer hybridize to a single-stranded target nucleic acid, the resulting complex (see, e.g., FIG. 6) simulates an abasic site for Endonuclease IV. The endonuclease recognizes the structure and cleaves the 3'-tail of the probe. Where the 3'-tail incorporates a fluorescent dye, and where a quencher moiety is conjugated to the opposite 5'-end of the probe, the Endonuclease IV cleavage leads to disruption of the FRET effect between the dyes, resulting in an increase of the reaction fluorescence. The reaction is target specific, and the increase in fluorescence is indicative of the presence of the target nucleic acid in the reaction mixture. This detection technology is described, for example, in detail in Kutyavin I. V. et al, (2004 and 2006).

Figure 8:
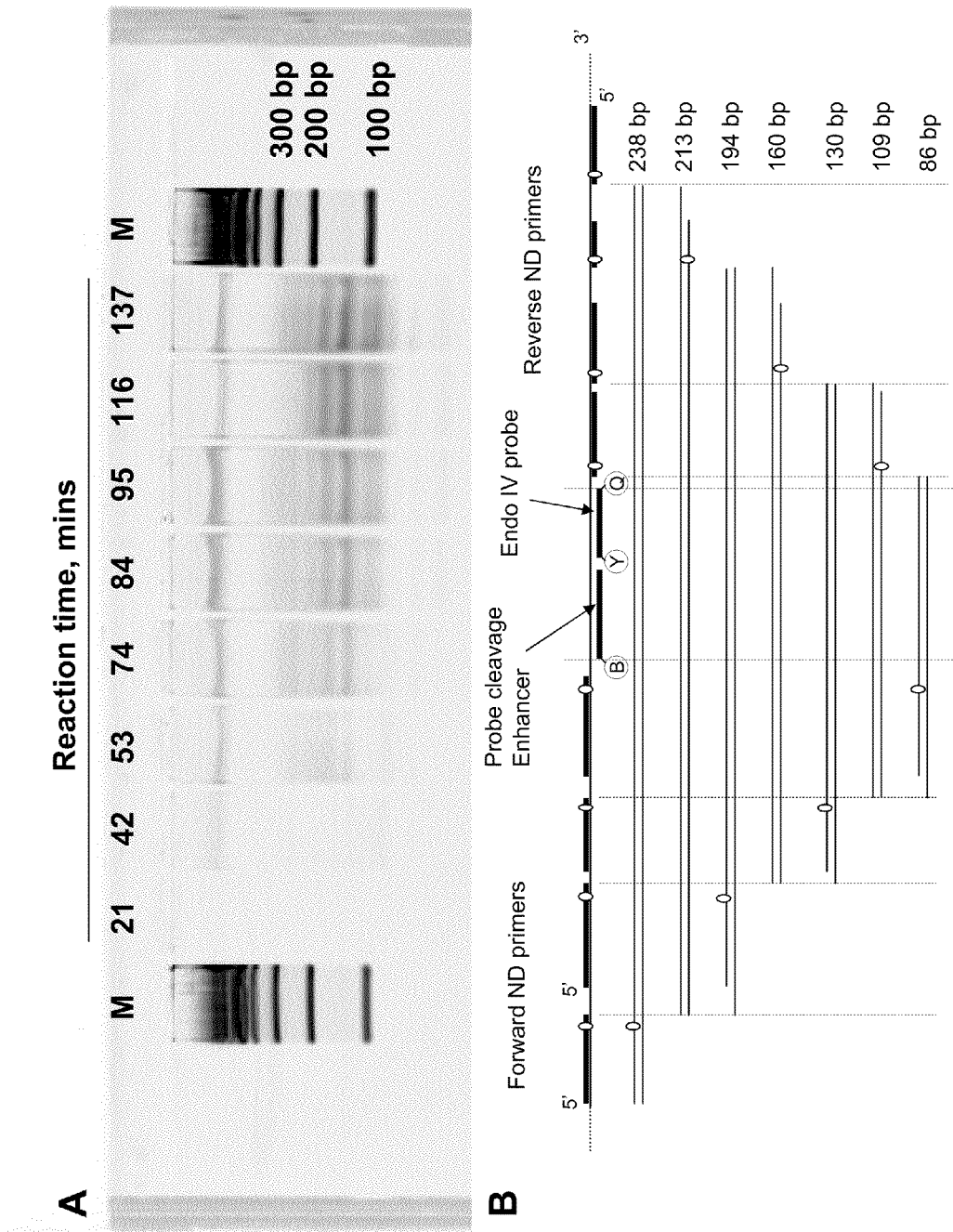
FIG. 8A shows, according to particular exemplary aspects of the present invention, results of a 10% polyacrylamide gel (PAAG) electrophoretic analysis of products of the Accelerated Cascade Amplification of M13mp18. Like the "8 Primers" reaction shown in FIG. 7, the reaction mixtures comprised M13mp18 target DNA (108 copies per reaction), eight (8) ND primers (FIG. 6 Primers 1-8), nick displacing DNA polymerase, Endonuclease V and deoxynucleoside 5'-triphosphates in 50 mM KCl, 1 mM MgCl$_2$, 20 mM Tris-HCl (pH8.0). The reaction was incubated at 46° C. and the analyzed samples of the reaction were taken at times as indicated at the top of each sample well (gel lane). The "M" lanes correspond to sample wells loaded with DNA duplex markers of 100, 200, 300 and incrementally longer base pairs (bp). DNA in the gel was visualized by monitoring fluorescence of SYBR Green added to the samples prior the electrophoresis. A series of discrete double-stranded reaction products are visible in the lanes, and increase in intensity with reaction time. Based on the molecular weight markers, the primary reaction products are between about 50 and about 250 bp. A detailed description of the experiment and results is provided herein under working EXAMPLE 2.
FIG. 8B shows (upper portion of FIG. 8B) a schematic representation of a portion of a target M13mp18 nucleic acid along with alignment of four (4) forward, four (4) reverse ND primers, Endo IV cleavable FRET probe and the Probe Cleavage Enhancer. Oligonucleotide lengths, relative position of oligonucleotides vs. target nucleic acid and each other are shown to scale with the 5'-3' orientation as indicated. The sequence and alignment of the primers, Endo IV probe and the Probe Cleavage Enhancer are as shown in FIG. 6 herein (although relative to FIG. 6, the forward and reverse directions have been reversed for illustrative convenience). Putative double-stranded Accelerated Cascade Amplification (ACA) products are also depicted below the target nucleic acid schematic. According to particular aspects of Applicant's conception, as described in more detail herein under working Example 2, these double-stranded products represent the products predicted if: (i) the amplification is initiated by the most external reverse primer; and (ii) the primers enter the amplification sequentially, one after another. The numbers shown to the right of the respective reaction products indicate the anticipated amplicon length (in base pairs (bp)), calculated for the longest strand of each double-stranded product, with ND primers incorporated. As can be seen, the predicted amplicon lengths (i.e., 86, 109, 130, 160, 194, 213 and 238) correlate very well with the actual polyacrylamide agarose gel (PAAG) electrophoretic profiles of FIG. 8A, showing respective bands of these size classes.

The results shown in FIG. 9 indicate that, relative to the reaction mixture components of the non-FRET-based ACA reactions represented in FIGS. 7 and 8, the presence of the FRET probe, cleavage enhancer and additional endonuclease, i.e. Endonuclease IV, did not interfere with the inventive ACA amplification system. 'S-shaped' real-time curves were observed in all cases when the target DNA was present in the reaction mixtures. The data also shows that the ACA amplicons incorporate single-stranded target fragments complementary to the probe and enhancer at a sufficient concentration to be detected in FRET-based assays. The results of FIG. 9 illustrate that methods of the invention have substantial and broad utility for nucleic acid detection, including substantial utility for such formats as real-time detection methods. Moreover, the data of this experiment also indicates that the inventive ACA methods can be used for quantitative measurements of target nucleic acids in samples. For example, as shown in FIG. 9, the appearance of the fluorescence curve threshold in time was found to be in proportion to the initial target concentration.

Example 4

Mechanistic Considerations with Respect to Accelerated Cascade Amplification (ACA), and Further Enhanced ACA Embodiments This Example discusses mechanistic considerations with respect to Accelerated Cascade Amplification (ACA), and discloses further enhanced ACA methods.

Those of ordinary skill in the art will appreciate that, based on the examples provided herein, and on the cumulative knowledge in the relevant art, it may be difficult, if not impossible to establish a definitive mechanism of a complex and multi-component reaction such as the presently disclosed Accelerated Cascade Amplification (ACA). Likely, further research will be required to fully explain the unexpected results provided herein and, in particular the dependence of the accelerated cascade amplification rate on the number of nick-directing (ND) primers used in the ACA reaction Nonetheless, without being bound by any particular theory, and according to particular aspects of Applicant's conception, ACA amplification is most likely not a random or chaotic process, but rather an organized process of sequential amplification reactions, wherein the ND primers of ACA effectively enter into the ACA amplification process in a sequential cascade (e.g, one after another)'; that is, beginning with the most external of the internal ND primers, followed by the next most external of the internal ND primers, and so forth, in an sequential, cascading process which Applicant refers to herein as Accelerated Cascade Amplification (ACA).

ND Primer 'Entry' Via a Sequential Cascade

Applicant's hypothesis is based on the premise that the most external ND primer (e.g., forward ND primer) is initially or first engaged in recurring amplification (cleavage and extension) events, providing for multiple copies of target nucleic acid suitable for hybridization with the most external reverse ND primer molecules. The concentration of these target amplicons ($C_1$) provided by the most external forward ND primer in time (t) may be described by a simplified equation.

$$C_1 = C_0 \cdot K_1 \cdot t,$$

wherein $C_0$ is the starting concentration of the respective target strand and $K_1$ is a constant reflecting number of ND primer-mediated cleavage and polymerase extension cycles provided at this ND primer 1 within an incremental time period, e.g. one minute.

The opposing most external primer (e.g., the reverse ND primer 2) enters the amplification process second, hybridizing to the extension products of the most external forward ND primer 1, and provides respective amplification products based on recurring cleavage and extension ($C_2$) events—the concentration of which, in time, is described by respective equation $$C_2 = C_1 \cdot K_2 \cdot t,$$

which, given $C_1 = C_0 \cdot K_1 \cdot t$, may be transformed to $$C_2 = C_0 K_1 K_2 t^2.$$

Note that ND primers in this sequential ACA amplification scheme are not incorporated into their respective ND primer extension products because of the ND cleavage events. Therefore, the external forward primer 1 is not complementary to the amplicons produced by the most external reverse ND primer 2. However, the products of amplification generated by the ND primer 2, may serve as templates for the next internal forward ND primer 3, which has a template binding site that adjoins that of forward ND primer 1.

This next internal forward primer 3 thus enters the amplification system third, and provides respective amplification products based on recurring cleavage and extension ($C_3$) events—the concentration of which, in time, is described by respective equation $$C_3 = C_0 \cdot K_1 \cdot K_2 \cdot K_3 \cdot t^3.$$

Following the same sequential logic, products of the cleavage and extension of this internal forward ND primer 3 are not templates for the most external reverse ND primer 2, but nonetheless are products complementary to the next internal reverse ND primer 4, which has a template binding site that adjoins that of external reverse ND primer 2. This next internal reverse ND primer 4 thus enters the amplification system fourth, providing its own respective amplification products based on recurring cleavage and extension ($C_4$) events—the concentration of which, in time, is described by respective equation $$C_4 = C_0 \cdot K_1 \cdot K_2 K_3 \cdot K_4 \cdot t^4,$$

and so forth.

In Applicant's model, given a set of nested ND primers comprising a subset of progressively more internal forward ND primers and a subset of progressively more internal reverse ND primers, the ND primers enter the amplification reaction in a sequential order or cascade, wherein, for example, entry of the most external forward ND primer is followed by entry of the most external reverse ND primer, followed by the entry of the next progressively more internal forward ND primer, followed by entry of the next progressively more internal reverse ND primer, and so on, and wherein the ND primer 'entry order' is thereby effectively defined by the primer 'nesting structure'; that is, by the respective ND primer's binding-site location within the target nucleic acid relative to the binding-sties of the other ND primers. In this model, therefore, any forward external ND primer enters the system before the next progressively more internal forward ND primer, which in turn enters the system before the next progressively more internal forward ND primer, and so forth, and the same would apply with respect to the entry order of the reverse ND primer members of the nested ND primer set. Entry order of the ND primers thereby follows a progressively narrowing 'ping-pong' between forward and reverse primer members of the nested ND primer set.

Following this sequential cascade, the last ND primer, N, enters the amplification system last, providing its own respective amplification products based on recurring cleavage and extension ($C_N$) events—the concentration of which, in time, is described by respective equation $$C_N = C_0 \cdot K_1 \cdot K_2 K_3 \cdot \ldots K_N \cdot t^N.$$

The individual constants $K_N$ of the cleavage and extension cycling are primarily defined by the activities of the ND nuclease and the DNA polymerase at a given priming site, and this value may vary somewhat from primer to primer. However, assuming that these constants are identical, the above equation may be simplified to $$C_N = C_0 \cdot K^N \cdot t^N.$$

Significantly, with respect to the accelerated amplification aspect of ACA, Applicant notes that the mass of the amplification products ($C_F$) generated in ACA is a sum of products provided by the individual ND primers $C_F = C_1 + C_2 + C_3 + \ldots C_N$. The equation variable $t^N$ alone is a major mathematical function, particularly at N values>2, where the Nth power is the number of ND primers used in the ACA process, thereby explaining the substantial acceleration of amplification with each additional ND primer entering the system. On the one hand, the "primer saturation" effect observed in Example may reflect the time required before all ND primers become involved in ACA and the reaction reaches its maximum speed. Alternatively, the "primer saturation" effect may also reflect that at a number of ND primers>6, the amplification rate is predominantly controlled by a "rate-limiting" factor other than $t^N$. The factor $K^N$ (constant reflecting number of ND primer-mediated cleavage and polymerase extension cycles provided at a respective ND primer within an incremental time period) may represent such a rate-limiting factor; that is, where K (a measure of cycling capability) has a low value.

Delayed Accumulation of Shortest Amplicons

The hypothesis of sequential ND primer 'entry' in Accelerated Cascade Amplification (ACA) may, at least to some extent, also explain the appearance of the shortest amplicons in late stages of the amplification.

Representation of all Size Classes of the Nested ND Primer Set Structure

As discussed above, not only was the substantially enhanced amplification rate unexpected, but the representation of all theoretical size classes was unexpected. Applicant's proposed model involving sequential ND primer 'entry' in Accelerated Cascade Amplification (ACA) offers a plausible explanation for this result.

Basically, while the double-stranded nature of extension product complexes from the most external, e.g., forward ND primers would preclude hybridization by internal ND primers to those template complexes, subsequent nicking, strand displacement and generation of respective reverse ND primer-mediated extension products that lack the most external forward ND primer binding site, provides for templates that are only accessible by progressively more internal primers as the sequential cascade proceeds. All theoretical fragment sizes are thus generated, because not only is template access by internal primers facilitated by the amplification cascade, but the external primers are effectively recycled in essentially continuous production of amplification products.

Therefore, without being bound by mechanism, Applicant's model not only provides a plausible mechanism for unexpected aspects of ACA, but also provides a direction and method for even faster and more efficient ACA, based on the above equations, which indicate that the factor $K^N$ (a measure of cycling capability) likely represents a rate-limiting factor that can be enhanced by the use of appropriate enzymes.

Further ACA Improvements

The *E. coli* Endonuclease V used in the working Examples of the invention is known to have a limited cycling capability (Yao M. et al, 1994; Yao M. and Kow Y. W., 1994; Yao M., Kow Y. W., 1995; Yao M., Kow Y. W., 1996; Yao M., Kow Y. W., 1997). Therefore, according to additional aspects of the present invention, use of a cycling Endonuclease V having an increased cycling capability is used to further accelerate the system.

As used herein, the term Endonuclease V (Endo V) encompasses functional variants thereof, including any nuclease that having enzymatic activity (cleavage specificity and/or activity) of the Endonuclease V from *Escherichia coli*, which, for example, preferentially hydrolyzes the second phosphodiester bond in the DNA strand on the 3' side of a deoxyinosine or deoxyuridine modification). In a preferred embodiment of the invention, the Endonuclease V is a variant or mutant Endonuclease V that has an enhanced cycling capability, such as at least one Endonuclease V (*Thermotoga maritime*) mutant selected from a group consisting of Y80A, H116A, R88A and K139A mutants.

Additional mutants encompassed by the present invention are described in U.S. Pat. No. 7,198,894, which is incorporated herein by reference. Certain nucleases other than ND nucleases may be used in practicing methods of the invention, in particular, for nucleic acid detection by real-time detection.

Cooperative and/or Synergistic Amplification by ND-Primers in ACA

According to particular aspects, the observed ACA amplification rates are highly cooperative and/or synergistic relative not only to the amplification rate expected and observed using only two external ND-primers (e.g., as in NDA methods), but also with respect to what might be expected based on amplification rates observed in art-recognized multi-plex PCR methods.

For example, in art-recognized multi-plex PCR methods, the mass accumulation rate of the total mass of amplified material (e.g., amplified material from all targets in the reaction) is the additive sum of the individual mass accumulation rates for each target. Accordingly, the amount of amplicon material produced in a single PCR cycle using two pairs of primers (one for each of two similarly sized targets) is roughly double the amount of amplicon material produced in a single PCR cycle using only one pair of primers (for a single target); that is, effectively equivalent to the benefit of an additional cycle.

By contrast, and as shown herein, the observed ACA amplification rates are highly cooperative and/or synergistic relative to prior art techniques, in that the use of additional ND-primers provides for amplification enhancement in excess over that expected for any mere additive sum of individual mass accumulation rates of amplicons of the amplifiable target sequence.

In PCR, when the initial concentration of the target nucleic acids is low (<100 copies per reaction), it can take about 20-30 PCR cycles to amplify the target nucleic acids to a detectable level. Based on the above estimates, a 15-30 minutes long individual PCR reaction can be 'accelerated' in the amplicon mass production when two targets are amplified instead one by ~45-60 seconds (one cycle). This is a relatively minor increase in PCR productivity or speed. Knowing that many of isothermal amplification technologies are generally slower than PCR, the same reaction 'acceleration', if not worse than that, may be anticipated for the isothermal amplification reactions, if the additional primers introduced to the reaction mixture would have the additive effect on the reaction productivity.

In this aspect, the acceleration observed in ACA of the present invention cannot be explained by the additive effect. SYBR Green dye used in the Examples of the invention detects the overall amount of double-stranded amplicons. The unusual and very rapid acceleration in the amplicon mass production observed herein with every single additional ND primer introduced into the reaction indicates a cooperative or synergistic effect in increasing the amount of the amplified material in ACA. For example, addition of fourth ND primer (curve "4 Primers" in FIG. 7) to the reaction with three ND primers ("3 Primers") reduced the reaction time by as much as ~80 minutes from ~130 to ~50 minutes.

REFERENCES CITED (AND INCORPORATED HEREIN BY REFERENCE THERETO)

Afonina I., Zivarts M., Kutyavin I., Lukhtanov E., Gamper H. and Meyer R. B. (1997) Efficient Priming of PCR with Short Oligonucleotides Conjugated to a Minor Groove Binder. *Nucleic Acids Res.*, 25: 2657-2660.

Afonina I. A., Reed M. W., Lusby E., Shishkina I. G. and Belousov Y. S. (2002) Minor groove binder-conjugated DNA probes for Quantitative DNA detection by hybridization-triggered fluorescence. *BioTechniques*, 32: 940-949.

An L., Tang W., Ranalli T. A., Kim H.-J., Wytiaz J., and Kong H. (2005) Characterization of a thermostable UvrD Helicase and its participation in helicase dependant amplification, *J. Biol. Chem.*, 280, 28952-28958.

Asseline U., Delarue M., Lancelot G., Toulme F., Thuong N. T., Montenay-Garestier T., Helene C. (1984) Nucleic acid-binding molecules with high affinity and base sequence specificity: intercalating agents covalently linked to oligonucleotides. *Proc. Natl. Acad. Sci. USA*, 81, 3297-3301.

Ausubel F. M, Brent R., Kingston R. E., Moore D. D., Seidman J. G., and Struhl K., eds., (1993) *Current Protocols in Molecular Biology*, Vol. 1, Chapter 2, Section I, John Wiley & Sons, New York.

Barany F. (1991) Genetic disease detection and DNA amplification using cloned thermostable ligase. *Proc. Natl. Acad. Sci. USA*, 88, 189-193.

Barany F., Cao W., Huang J., Lu J. (2007) Detection of nucleic acid differences using combined endonuclease cleavage and ligation reactions, U.S. Pat. No. 7,198,894.

Beaucage S. L., Caruthers M. H. (1981) Deoxynucleoside phosphoramidites—A new class of key intermediates for deoxypolynucleotide synthesis, *Tetrahedron Lett.*, 22: 1859-1862.

Blanco L., Bernard A., Lazaro J. M., Martin G., Garmendia C. And Salas M. (1989) Highly efficient DNA synthesis by the phage φ29 DNA polymerase. Symmetrical mode of DNA replication. *J. Biol. Chem.*, 264, 8935-8940.

Bonnet G., Tyagi S., Libchaber A. and Kramer, F. R. (1999) Thermodynamic basis of the enhanced specificity of structured DNA probes. *Proc. Natl. Acad. Sci. USA*, 96: 6171-6176.

Boom W. R., Henriette M. A., Kievits T., Lens P. F. (1993) Process for isolating nucleic acid, U.S. Pat. No. 5,234,809.

Breslauer K. J., Frank R., Blocker H., Marky L. A. (1986) Predicting DNA duplex stability from the base sequence, *Proc. Natl. Acad. Sci. USA*, 83: 3746-3750.

Brow M. A. D., Hall J. S. G., Lyamichev V., Olive D. M., Prudent J. R. (1998) Detection of nucleic acid sequences by invader-directed cleavage. U.S. Pat. No. 5,846,717.

Brown E. L., Belagaje R., Ryan M. J., Khorana H. G. (1979) Chemical synthesis and cloning of a tyrosine tRNA gene, *Methods Enzymol.*, 68: 109-151.

Burgner D., D'Amato M., Kwiatkowski D. P., Loakes D. (2004) Improved allelic differentiation using sequence-specific oligonucleotide hybridization incorporating an additional base-analogue mismatch, *Nucleosides Nucleotides Nucleic Acids*, 23: 755-765.

Cardullo R. A., Agrawal S., Flores C., Zamecnik P. C. and Wolf D. E. (1988) Nucleic acid hybridization by nonradioactive fluorescence resonance energy transfer. *Proc. Natl. Acad. Sci. USA*, 85: 8790-8794.

Caruthers M. H., Matteucci M. D. (1984) Process for preparing polynucleotides, U.S. Pat. No. 4,458,066.

Clegg R. M. (1992) Fluorescence resonance energy transfer and nucleic acids. *Methods Enzymol.*, 211: 353-388.

Clegg R. M. (1995) Fluorescence energy transfer. *Curr. Opin. Biotech.*, 6: 103-110.

Cleuziat P. and Mandrand B. (1998) Method for amplifying nucleic acid sequences by strand displacement using DNA/RNA chimeric primers, U.S. Pat. No. 5,824,517.

Davey C. and Malek L. T. (2000) Nucleic acid amplification process, U.S. Pat. No. 6,063,603.

Didenko V. V. (2001) DNA probes using fluorescence resonance energy transfer (FRET): design and application. *BioTechniques*, 31, 1106-1121.

Di Giusto D. A. and King G. C. (2004) Strong positional preference in the interaction of LNA oligonucleotides with DNA polymerase and proofreading exonuclease activities: implications for genotyping assays. *Nucleic Acids Res.*, 32: e32.

Doty P., Marmur J. E. and Schildkraut C. (1960) Strand separation and specific recombination in deoxyribonucleic acids: Physical chemical studies, *Proc. Natl. Acad. Sci. USA*, 46: 461-476.

Eckstein F., ed., (1991) *Oligonucleotides and Analogs: A Practical Approach*. Oxford University Press, New York.

Egholm M., Buchardt O., Christensen L., Behrens C., Freier S. M., Driver D. A., Berg R. H., Kim S. K., Norden B. and Nielsen P. E. (1993) PNA hybridizes to complementary oligonucleotides obeying the Watson-Crick hydrogen bonding rules, *Nature*, 365, 566-568.

Eftink M. R. (1991) Fluorescence quenching: theory and applications. In Lakowicz J. R. (ed.), *Topics in Fluorescence Spectroscopy*. Plenum Press, New York, V. 2: 53-126.

Förster T. (1965) Delocalized excitation and excitation transfer. In Sinanoglu, O. (ed.), *Modern Quantum Chemistry, Istanbul Lectures, part III*. Academic Press, New York: 93-137.

Fraiser M. S., Spargo C. A., Walker G. T., Van Cleve M., Wright D. J., Little M. C. (1997) Strand displacement amplification using thermophilic enzymes. U.S. Pat. No. 5,648,211.

Froehler, B., Wagner, R., Matteucci, M., Jones, R. J., Gutierrez, A. J., Pudlo, J. (1997) Enhanced triple-helix and double-helix formation with oligomers containing modified pyrimidines, U.S. Pat. No. 5,645,985.

Gait M. J., ed., (1984) *Oligonucleotide Synthesis: A Practical Approach*, IRL Practical Approach Series, IRL Press, Oxford.

Gall A. A., Kutyavin I. V., Vermeulen N. M. J., Dempcy R. O. (2003) Non-aggregating, non-quenching oligomers comprising nucleotide analogues; methods of synthesis and use thereof. U.S. Pat. No. 6,660,845.

Gates F. T. III and Linn S. (1977) Endonuclease V of *Escherichia coli*. *J. Biol. Chem.*, 252, 1647-1653.

Huang J., Lu J., Barany F., and Cao W. (2001) Multiple cleavage activities of Endonuclease V from *Thermotoga maritima*: Recognition and strand nicking mechanism. *Biochemistry*, 40, 8738-8748.

Huang J., Lu J., Barany F., and Cao W. (2002) Mutational analysis of Endonuclease V from *Thermotoga maritima*. *Biochemistry*, 41, 8342-8350.

Kornberg A., and Baker T. (1992) *DNA Replication*, Second Edition, W.H. Freeman and Company, New York.

Kurn N. (2001) Methods and compositions for linear isothermal amplification of polynucleotide sequences, using a RNA-DNA composite primer, U.S. Pat. No. 6,251,639.

Kurn, N. (2004) Methods and compositions for linear isothermal amplification of polynucleotide sequences. U.S. Pat. No. 6,692,918.

Kurn, N. (2005) Methods and compositions for generation of multiple copies of nucleic acid sequences and methods of detection thereof. U.S. Pat. No. 6,858,413.

Kutyavin I. V., Lukhtanov E. A., Gamper H. B., Meyer R. B., Gall A. (1997) Oligonucleotide-cyclopropapyrroloindole conjugates as sequence specific hybridization and crosslinking agents for nucleic acids, U.S. Pat. No. 5,659,022.

Kutyavin I. V., Lukhtanov E. A., Gamper H. B., Meyer R. B. (1998) Covalently linked oligonucleotide minor groove binder conjugates, U.S. Pat. No. 5,801,155.

Kutyavin I. V., Milesi D., Hoekstra M. F. (2004) Abasic site endonuclease assay, US Patent Application #20040101893.

Kutyavin I. V., Milesi D., Belousov Y., Podyminogin M., Vorobiev A., Gorn V., Lukhtanov E. A., Vermeulen N. M. J., Mahoney W. (2006) A novel endonuclease IV post-PCR genotyping system. *Nucleic Acids Res.*, 34: e128.

Kutyavin I. V. (2007a) Use of products of PCR amplification carrying elements of secondary structure to improve PCR-based nucleic acid detection, WO/2007/127999; PCT/US2007/067836.

Kutyavin I. V. (2007b) Use of base-modified deoxynucleoside triphosphates to improve nucleic acid detection, WO/2007/127992; PCT/US2007/067826.

Latorra D., Arar K., Hurley J. M. (2003a) Design considerations and effects of LNA in PCR primers, *Mol. Cell. Probes*, 17: 253-259.

Latorra D., Campbell K., Wolter A., Hurley J. M. (2003b) Enhanced allele-specific PCR discrimination in SNP genotyping using 3' locked nucleic acid (LNA) primers, *Hum. Mutat.*, 22: 79-85.

Lebedev Y., Akopyans N., Azhikina T., Shevchenko Y., Potapov V., Stecenko D., Berg D., Sverdlov E. (1996) Oligonucleotides containing 2-aminoadenine and 5-methylcytosine are more effective as primers for PCR amplification than their nonmodified counterparts, *Genet. Anal.*, 13, 15-21.

Lehninger A. L. (1975) *Biochemistry*, 2nd edition. New York, Worth Publishers, Inc.

Liu J., He B., Qing H., and Kow Y. W. (2000) A deoxyinosine specific endonuclease from hyperthermophile, *Archaeoglobus fulgidus*: a homolog of *Escherichia coli* endonuclease V. *Mut. Res.*, 461, 169-177.

Livak K. J., Flood S. J. A., Marmaro J. and Mullah K. B. (1998) Self-quenching fluorescent probe. U.S. Pat. No. 5,723,591.

Lizardi P. (1998) Rolling circle replication reporter systems, U.S. Pat. No. 5,854,033.

Lizardi P. M. and Caplan, M. (1998) Unimolecular segment amplification and sequencing. U.S. Pat. No. 6,143,495.

Lizardi P. M. (2001a) Rolling circle replication reporter systems. U.S. Pat. No. 6,210,884.

Lizardi P. M. (2001b) Molecular cloning using rolling circle amplification. U.S. Pat. No. 6,287,824.

Lyamichev V., Mast A., Hall J., Prudent J., Kaiser M., Takova T., Kwiatkowski R., Sander T., de Arruda M., Arco D., Neri B. and Brow M. (1999) Polymorphism identification and quantitative detection of genomic DNA by invasive cleavage of oligonucleotide probes. *Nat. Biotechnol.*, 17, 292-296.

Mackay I. M., Arden K. E., Nitsche A. (2002) Real-time PCR in virology, *Nucleic Acids Res.*, 30: 1292-1305.

Mackay J., Landt O. (2007) Real-time PCR fluorescent chemistries, *Methods Mol. Biol.*, 353: 237-262.

Marras S. A. E., Kramer F. R. and Tyagi S. (2002) Efficiencies of fluorescence resonance energy transfer and contact-mediated quenching in oligonucleotide probes. *Nucleic Acids Res.*, 30: e122.

McPherson M. J., Quirke P., Taylor G. R., eds (1991) *PCR: A Practical Approach*. IRL Press, Oxford. McPherson M. J., Quirke P., Taylor G. R., eds (1995) *PCR2: A Practical Approach*. IRL Press, Oxford.

Meyer R. B., Afonina I. A., Kutyavin I. V. (2000) Oligonucleotide containing pyrazolo[3,4-d]pyrimidines for hybridization and mismatch discrimination. U.S. Pat. No. 6,127,121.

Millar D. S., Melki J. R., Grigg G. W. (2006) Isothermal strand displacement amplification using primers containing a non-regular base, WO 2006/125267.

Miller S. A., Dykes D. D. and Polesky H. F. (1988) A simple salting out procedure for extracting DNA from human nucleated cells. *Nucleic Acids Res.*, 16: 1215.

Moe A., Ringvoll J., Nordstrand L. M., Eide L., Bjørås M., Seeberg E., Rognes T. and Klungland A. (2003) Incision at hypoxanthine residues in DNA by a mammalian homologue of the *Escherichia coli* antimutator enzyme endonuclease V. *Nucleic Acids Res.*, 31, 3893-3900.

Mukai H., Sagawa H., Uemori T., Yamamoto J., Tomono J., Kobavashi E., Euoki T., Takeda O., Miyake K., Sato Y., Moriyama M., Sawaragi H., Hagiya M., Asada K., Kato I. (2003) Method for amplifying nucleic acid sequence. US Patent application 20030073081.

Mullis K. B. (1987) Process for amplifying nucleic acid sequences, U.S. Pat. No. 4,683,202.

Mullis K. B., Erlich H. A., Arnheim N., Horn G. T., Saiki R. K., and Scharf S. J. (1987) Process for amplifying, detecting, and/or -cloning nucleic acid sequences, U.S. Pat. No. 4,683,195.

Mulrooney C. and Oultram J. D. (1999) Amplification of nucleic acids, WO/1999/049081; PCT/GB1999/000929.

Narang S. A., Hsiung H. M., Brousseau R. (1979) Improved phosphotriester method for the synthesis of gene fragments, *Methods Enzymol.*, 68: 90-98.

Nguyen T. T., Helene C., Asseline U. (1989) Novel compounds containing an oligonucleotide sequence bounded to an intercalating agent, a process for their synthesis and their use, U.S. Pat. No. 4,835,263.

Notomi T. and Hase T. (2002) Process for synthesizing nucleic acid, U.S. Pat. No. 6,410,278.

Notomi T., Okayama H., Masubuchi H., Yonekawa T., Watanabe K., Amino N., and Hase T. (2000) Loop-mediated isothermal amplification of DNA, *Nucleic Acids Res.*, 28, e63.

Oehlenschlager F., Schwille P. and Eigen M. (1996) Detection of HIV-1 RNA by nucleic acid sequence-based amplification combined with fluorescence correlation spectroscopy. *Proc. Natl. Acad. Sci. USA*, 93, 12811-12816.

Oultram J. D. and Coutts J. (1999) Amplification of nucleic acids, WO/1999/009211; PCT/GB1998/002427.

Ortiz E., Estrada G. and Lizardi P. M. (1998) PNA molecular beacons for rapid detection of PCR amplicons. *Mol. Cell. Probes*, 12, 219-226.

Petrie, C. R., Meyer, R. B., Tabone, J. C., Hurst, G. D. (1998) Cross-linking oligonucleotides. U.S. Pat. No. 5,824,796.

Robelek R., Niu L., Schmid E. L., Knoll W. (2004) Multiplexed hybridization detection of quantum dot-conjugated DNA sequences using surface plasmon enhanced fluorescence microscopy and spectrometry, *Anal. Chem.*, 76: 6160-6165.

Saba J. (2004) An Isothermal Nucleic Acid Amplification (Nick Displacement Amplification, U.S. Provisional patent application Ser. No. 60/211,975 filed on Jun. 16, 2000 and disclosed on May 16, 2004 in: http://www.wbabin.net/saba/saba13.htm.

Sagawa H., Uemori T., Mukai H., Yamamoto J., Tomono J., Kobayashi E., Enoki T., Asada K., Kato I. (2003) Method of amplifying nucleic acid. European Patent Application #1312682.

Sambrook J., Fritsch E. F. and Maniatis T. (1989) *Molecular Cloning: A Laboratory Manual,* 2nd Edition. Cold Spring Harbor Lab. Cold Spring Harbor, N.Y.

SantaLucia J. Jr. (1998) A unified view of polymer, dumbbell, and oligonucleotide DNA nearest-neighbor thermodynamics. *Proc. Natl. Acad. Sci. USA*, 95: 1460-1465.

Selvin P. R. (1995) Fluorescence resonance energy transfer. *Methods Enzymol.*, 246: 300-334.

Simpson D., Crosby R. M., and Skopek T. R. (1988) A method for specific cloning and sequencing of human hprt cDNA for mutation analysis. *Biochem. Biophys. Res. Commun.*, 151: 487-492.

Stryer L. and Haugland R. P. (1967) Energy transfer: a spectroscopic ruler. *Proc. Natl. Acad. Sci. USA*, 58: 719-726.

Tyagi S., Kramer F. R., Lizardi P. M. (1999) Detectably labeled dual conformation oligonucleotide probes, assays and kits, U.S. Pat. No. 5,925,517.

Van Ness J., Van Ness L. K., and Galas D. J. (2003a) Isothermal reactions for the amplification of oligonucleotides, *Proc. Natl. Acad. Sci. USA*, 100, 4504-4509.

Van Ness J., Galas D. J., Van Ness L. K. (2003b) Exponential amplification of nucleic acids using nicking agents, US Patent Application Publication #2003/0138800.

Vincent M., Xu Y. and Kong H. (2004) Helicase dependant isothermal DNA amplification, EMBO reports, 5: 795-800.

Walker G. T. (1998) Strand displacement amplification. U.S. Pat. No. 5,712,124.

Walker G. T., Linn C. P. and Nadeau J. G. (1996) DNA detection by strand displacement amplification and fluorescence polarization with signal enhancement using DNA binding protein. *Nucleic Acids Res.*, 24, 384-353.

Walker G. T., Little M. C., and Nadeau J. G. (1993) Nucleic acid target generation. U.S. Pat. No. 5,270,184.

Walsh P. S., Metzger D. A. and Higuchi R. (1991) Chelex 100 as a medium for simple extraction of DNA for PCR-based typing from forensic material. *Biotechniques*, 10: 506-513.

Walter A. E., Turner D. H., Kim J., Little M. H., Muller P., Mathews D. H., Zuker M. (1994) Coaxial stacking of helixes enhances binding of oligoribonucleotides and improves predictions of RNA folding, *Proc. Natl. Acad. Sci. USA*, 91: 9218-9222.

Wittwer C. T., Ririe K. M., Rasmussen R. P. (2001) Monitoring amplification of DNA during PCR, U.S. Pat. No. 6,174,670.

Wittwer C. T., Ririe K. M., Rasmussen R. P. (2003) Monitoring hybridization during PCR using SYBR™ Green I, U.S. Pat. No. 6,569,627.

Wu, D. Y. and Wallace, R. B. (1989) The ligation amplification (LAR)-amplification of specific DNA sequences using sequential rounds of template-dependant ligation. *Genomics*, 4, 560-569.

Yao M., Hatahet Z., Melamede R. J. and Kow Y. W. (1994) Purification and Characterization of a Novel Deoxyinosine-specific Enzyme, Deoxyinosine 3'-Endonuclease, from *Escherichia coli. J. Biol. Chem.*, 269, 16260-16268.

Yao M. and Kow Y. W. (1994) Strand-specific Cleavage of Mismatch-containing DNA by Deoxyinosine 3'-Endonuclease from *Escherichia coli. J. Biol. Chem.*, 269, 31390-31396.

Yao M., Kow Y. W. (1995) Interaction of Deoxyinosine 3'-Endonuclease from *Escherichia coli* with DNA Containing Deoxyinosine. *J. Biol. Chem.*, 270, 28609-28616.

Yao M., Kow Y. W. (1996) Cleavage of Insertion/Deletion Mismatches, Flap and Pseudo-Y DNA Structures by Deoxyinosine 3'-Endonuclease from *Escherichia coli*. *J. Biol. Chem.*, 271, 30672-30676.

Yao M., Kow Y. W. (1997) Further Characterization of *Escherichia coli* Endonuclease V. Mechanism of Recognition for Deoxyinosine, Deoxyuridine, and Base Mismatches in DNA. *J. Biol. Chem.*, 272, 30774-30779.

Zuker M. and Jacobsen A. B. (1995) Well-Determined Regions in RNA Secondary Structure Prediction Analysis of small Subunit Ribosomal RNA, *Nucleic Acids Res.*, 23: 2791-2797.

---

The invention claimed is:

1. A method for amplification and detection of a nucleic acid sequence, comprising:
   a) providing a reaction mixture comprising
      at least one target nucleic acid sequence having an amplifiable target sequence,
      a forward external nick-directing oligonucleotide primer (ND-primer) and a reverse external ND-primer, the external primers suitable to hybridize to the target nucleic acid sequence at nucleotide positions external to the amplifiable target sequence,
      at least one internal ND-primer suitable to hybridize to an external ND-primer extension product comprising the amplifiable target sequence or a portion thereof, but lacking a respective ND primer sequence or a portion thereof,
      a strand-displacing DNA polymerase suitable for primer extension of the hybridized primers, to provide respective primer-extension products,
      a nick-directing endonuclease suitable for strand-specific cleavage of the ND-primer-extension products to provide for primer-extension products lacking the respective ND-primers or portions thereof,
      a cleavable FRET probe, and
      a mixture of deoxynucleoside 5'-triphosphates;
   b) incubating the reaction mixture in the presence of reagents, and under reaction conditions suitable to support primer hybridization, DNA polymerase-mediated primer extension and strand displacement, and nick-directing endonuclease-mediated strand-specific cleavage of the extension products, to provide for amplification of the amplifiable target sequence, wherein the amplification comprises primer extension, by least one internal ND-primer, of an external ND-primer extension product comprising the amplifiable target sequence or a portion thereof but lacking the respective external ND-primer sequence or a portion thereof; and
   c) detecting, based on the cleavable FRET probe, the amplified target sequence or portion thereof.

2. The method of claim 1, comprising use of a plurality of internal ND-primers, and wherein the amplification comprises primer extension, by least one internal ND-primer, of an extension product of a different internal ND-primer lacking the respective different internal ND-primer sequence or a portion thereof.

3. The method of claim 2, comprising at least one forward internal ND-primer, and at least one reverse internal ND-primer.

4. The method of claim 2, wherein the plurality of internal ND-primers comprises a nested set of internal ND-primers.

5. The method of claim 4, wherein the nested set of internal ND-primers comprises both forward and reverse internal ND-primers.

6. The method of claim 2, wherein the number of internal ND-primers used is a number equal to or greater than 2.

7. The method of claim 2, wherein the number of internal ND-primers used is a number in the range from 1 to 8.

8. The method of claim 1, wherein at least one of the ND-primers incorporates at least one of a deoxyinosine and a deoxyuridine nucleoside as a nick-directing modification, and wherein the nick-directing nuclease comprises Endonuclease V.

9. The method of claim 1, wherein the amplification rate or efficiency is enhanced relative to amplification mediated by use of the external ND-primers only.

10. The method of claim 9, wherein the enhancement is synergistic with respect to the number of primers employed.

11. The method of claim 1, wherein in incubating to provide for amplification of the amplifiable target sequence, the concentration of extension products of an internal ND-primer N, per unit reaction time, is approximated by the general formula $$C_N = C_0 \cdot K^N \cdot t^N$$

as defined herein.

12. The method of any one of claims 1 and 2, wherein amplification comprises or consists of isothermal amplification.

13. The method of claim 12, wherein the isothermal amplification is performed at a temperature in the range of about 15° C. to about 80° C., or in the range of about 45° C. to about 75° C.

14. The method of claim 1, further comprising detecting the amplified target sequence by at least one of post-amplification detection, and real-time detection.

15. The method of claim 1, wherein the target nucleic acid is single-stranded.

16. The method of claim 1, wherein the target nucleic acid is double-stranded, and wherein prior to, or during, the amplification reaction the double-stranded target nucleic acid is rendered single-stranded.

17. The method of claim 1, wherein the target nucleic acid is DNA.

18. The method of claim 1, wherein the target nucleic acid is RNA, or wherein at least one DNA copy of the RNA is synthesized using a reverse transcriptase prior to amplifying the amplifiable target DNA sequence.

19. The method of claim 1, wherein at least two of the ND-primers incorporate different nick-directing modifications, and the reaction mixture comprises respective nick-directing endonucleases providing for cleavage of ND-primer extension products comprising the different nick directing modifications.

20. The method of claim 1, wherein the reaction mixture comprises a plurality of target nucleic acids, and wherein a respective plurality of amplifiable target sequences is amplified by use of respective sets of ND-primers.

21. The method of claim 20, wherein the amplification comprises whole genome amplification.

22. The method of claim 1, wherein at least one of the ND-primers contains at least one structural modification other than a nick-directing modification.

23. The method of claim 22, wherein the structural modification comprises at least one duplex-stabilizing modification selected from one or more modified nucleotides, and a tail conjugated to the 5'-end of the ND-primer.

24. The method of claim 23, wherein the tail is at least one of an intercalator and a minor groove binder.

25. The method of claim 1, wherein detection of the signal is indicative of at least one of the presence, and the amount of the target nucleic acid in the reaction mixture.

26. The method of claim 1, wherein the cleavable FRET probe changes its fluorescent properties upon forming a complementary complex with the amplification products.

27. The method of claim 1, wherein detecting further comprises use of a hybridization-triggered FRET probe.

28. The method of claim 1, wherein the cleavable FRET probe comprises an Endonuclease IV-cleavable probe and the reaction mixture additionally incorporates Endonuclease IV.

29. The method of claim 1, wherein the strand-displacing DNA polymerase has no 3'→5' nuclease activity.

30. The method of claim 1, wherein the nick-directing endonuclease comprises a nuclease with cleavage cycling capability, providing for cleavage of greater than 1, greater than 5, or greater than 10 ND-primer extension products per minute under the reaction conditions.

31. The method of claim 1, wherein the Endonuclease V is that of *Thermotoga maritima* (SEQ ID NO:19), a variant thereof, or a mutant thereof selected from a group consisting of Y80A (SEQ ID NO:20), H116A (SEQ ID NO:21), R88A (SEQ ID NO:22) and K139A (SEQ ID NO:23).

32. The method of claim 1, wherein at least one ND-primer is immobilized on a solid support.

33. The method of claim 1, wherein at least one of the ND-primers is designed using specialty computer software.

34. A method for detection of a nucleic acid sequence in a sample, comprising:
obtaining a sample comprising at least one target nucleic acid sequence having an amplifiable target sequence;
amplifying the amplifiable target sequence according the method of any one of claims 1 and 2; and
detecting the amplified target sequence by at least one of post-amplification detection, and real-time detection.

* * * * *